(12) United States Patent
Brandolini et al.

(10) Patent No.: US 11,819,386 B2
(45) Date of Patent: Nov. 21, 2023

(54) APPARATUSES AND METHODS FOR NEGATIVE PRESSURE WOUND THERAPY

(71) Applicant: T.J.Smith and Nephew, Limited, Hull (GB)

(72) Inventors: Nicola Brandolini, Ravenna (IT); Felix Clarence Quintanar, Hull (GB)

(73) Assignee: T.J.Smith and Nephew, Limited, Hull (GB)

( * ) Notice: Subject to any disclaimer, the term of this patent is extended or adjusted under 35 U.S.C. 154(b) by 33 days.

(21) Appl. No.: 17/259,891

(22) PCT Filed: Jul. 8, 2019

(86) PCT No.: PCT/EP2019/068201
§ 371 (c)(1),
(2) Date: Jan. 12, 2021

(87) PCT Pub. No.: WO2020/011691
PCT Pub. Date: Jan. 16, 2020

(65) Prior Publication Data
US 2021/0290837 A1 Sep. 23, 2021

(30) Foreign Application Priority Data
Jul. 12, 2018 (GB) .................................... 1811449

(51) Int. Cl.
*A61F 13/00* (2006.01)
*A61M 1/00* (2006.01)

(52) U.S. Cl.
CPC ....... *A61F 13/00068* (2013.01); *A61M 1/913* (2021.05); *A61M 1/915* (2021.05);
(Continued)

(58) Field of Classification Search
CPC ...... A61M 1/915; A61M 1/913; A61M 1/985; A61M 2205/75; A61M 1/90; A61M 1/964; A61M 2205/3334; A61F 13/00068
See application file for complete search history.

(56) References Cited

U.S. PATENT DOCUMENTS 1,585,104 A 5/1926 Montgomery
2,736,317 A 2/1956 Alexander
(Continued)

FOREIGN PATENT DOCUMENTS

DE 3443101 A1 5/1986
DE 3907007 A1 9/1990
(Continued)

OTHER PUBLICATIONS

Bevan D., et al., "Diverse and potent activities of HGF/SF in skin wound repair," Journal of Pathology, vol. 203, 2004, pp. 831-838.
(Continued)

*Primary Examiner* — Sarah Al Hashimi
*Assistant Examiner* — Nhu Q. Tran
(74) *Attorney, Agent, or Firm* — Knobbe, Martens, Olson & Bear, LLP

(57) ABSTRACT

Disclosed herein are several embodiments of a negative pressure appliance and methods of using the same in the treatment of wounds. Some embodiments are directed to improved fluidic connectors or suction adapters for connecting to a wound site, having an air leak channel separated from a suction channel.

20 Claims, 24 Drawing Sheets

(52) U.S. Cl.
CPC .............. *A61M 1/964* (2021.05); *A61M 1/966* (2021.05); *A61M 1/985* (2021.05); *A61M 2205/75* (2013.01)

(56) References Cited

U.S. PATENT DOCUMENTS

| | | |
|---|---|---|
| 3,042,041 A | 7/1962 | Jascalevich |
| 3,255,749 A | 6/1966 | Smithers |
| 3,568,675 A | 3/1971 | Harvey |
| 3,572,340 A | 3/1971 | Lloyd et al. |
| 3,874,387 A | 4/1975 | Barbieri |
| 3,880,164 A | 4/1975 | Stepno |
| 3,927,443 A | 12/1975 | Brumlik |
| 3,943,734 A | 3/1976 | Fleissner |
| 3,972,328 A | 8/1976 | Chen |
| 4,029,598 A | 6/1977 | Neisius et al. |
| 4,080,970 A | 3/1978 | Miller |
| 4,117,551 A | 9/1978 | Brooks et al. |
| 4,164,027 A | 8/1979 | Bonnie et al. |
| 4,169,303 A | 10/1979 | Lemelson |
| 4,231,357 A | 11/1980 | Hessner |
| 4,261,363 A | 4/1981 | Russo |
| 4,360,015 A | 11/1982 | Mayer |
| 4,382,441 A | 5/1983 | Svedman |
| 4,392,853 A | 7/1983 | Muto |
| 4,468,219 A | 8/1984 | George et al. |
| 4,487,606 A | 12/1984 | Leviton et al. |
| 4,538,920 A | 9/1985 | Drake |
| 4,540,412 A | 9/1985 | Van Overloop |
| 4,553,967 A | 11/1985 | Ferguson et al. |
| 4,561,435 A | 12/1985 | McKnight et al. |
| 4,569,674 A | 2/1986 | Phillips et al. |
| 4,579,120 A | 4/1986 | MacGregor |
| 4,605,399 A | 8/1986 | Weston et al. |
| 4,614,183 A | 9/1986 | McCracken et al. |
| 4,665,909 A | 5/1987 | Trainor |
| 4,728,499 A | 3/1988 | Fehder |
| 4,753,536 A | 6/1988 | Spehar et al. |
| 4,767,026 A | 8/1988 | Keller et al. |
| 4,771,919 A | 9/1988 | Ernst |
| 4,813,942 A | 3/1989 | Alvarez |
| 4,872,450 A | 10/1989 | Austad |
| 4,906,240 A | 3/1990 | Reed et al. |
| 4,921,492 A | 5/1990 | Schultz et al. |
| 4,941,882 A | 7/1990 | Ward et al. |
| 4,969,880 A | 11/1990 | Zamierowski |
| 4,980,226 A | 12/1990 | Hellgren et al. |
| 5,009,224 A | 4/1991 | Cole |
| 5,056,510 A | 10/1991 | Gilman |
| 5,060,642 A | 10/1991 | Gilman |
| 5,064,653 A | 11/1991 | Sessions et al. |
| 5,080,493 A | 1/1992 | McKown et al. |
| 5,088,483 A | 2/1992 | Heinecke |
| 5,100,396 A | 3/1992 | Zamierowski |
| 5,106,362 A | 4/1992 | Gilman |
| 5,112,323 A | 5/1992 | Winkler et al. |
| 5,134,007 A | 7/1992 | Reising et al. |
| 5,139,023 A | 8/1992 | Stanley et al. |
| 5,149,331 A | 9/1992 | Ferdman et al. |
| 5,152,757 A | 10/1992 | Eriksson |
| 5,160,315 A | 11/1992 | Heinecke et al. |
| 5,160,334 A | 11/1992 | Billings et al. |
| 5,176,663 A | 1/1993 | Svedman et al. |
| 5,180,375 A | 1/1993 | Feibus |
| 5,181,905 A | 1/1993 | Flam |
| 5,218,973 A | 6/1993 | Weaver et al. |
| 5,230,496 A | 7/1993 | Shillington et al. |
| 5,238,732 A | 8/1993 | Krishnan |
| 5,244,457 A | 9/1993 | Karami et al. |
| 5,249,709 A | 10/1993 | Duckworth et al. |
| 5,261,893 A | 11/1993 | Zamierowski |
| 5,263,922 A | 11/1993 | Sova et al. |
| 5,300,054 A | 4/1994 | Feist et al. |
| 5,304,161 A | 4/1994 | Noel et al. |
| 5,308,313 A | 5/1994 | Karami et al. |
| 5,333,760 A | 8/1994 | Simmen |
| 5,358,492 A | 10/1994 | Feibus |
| 5,366,451 A | 11/1994 | Levesque |
| 5,391,161 A | 2/1995 | Hellgren et al. |
| 5,437,651 A | 8/1995 | Todd et al. |
| 5,447,492 A | 9/1995 | Cartmell et al. |
| 5,486,167 A | 1/1996 | Dragoo et al. |
| 5,525,407 A | 6/1996 | Yang |
| 5,527,293 A | 6/1996 | Zamierowski |
| 5,527,923 A | 6/1996 | Klingler et al. |
| 5,531,855 A | 7/1996 | Heinecke et al. |
| 5,549,584 A | 8/1996 | Gross |
| 5,582,596 A | 12/1996 | Fukunaga et al. |
| 5,593,750 A | 1/1997 | Rothrum et al. |
| 5,599,289 A | 2/1997 | Castellana |
| 5,603,145 A | 2/1997 | Arakawa et al. |
| 5,609,271 A | 3/1997 | Keller et al. |
| 5,613,942 A | 3/1997 | Lucast et al. |
| 5,618,278 A | 4/1997 | Rothrum |
| 5,618,556 A | 4/1997 | Johns et al. |
| 5,624,423 A | 4/1997 | Anjur et al. |
| 5,636,643 A | 6/1997 | Argenta et al. |
| 5,637,093 A | 6/1997 | Hyman et al. |
| 5,645,081 A | 7/1997 | Argenta et al. |
| 5,678,564 A | 10/1997 | Lawrence et al. |
| 5,695,846 A | 12/1997 | Lange et al. |
| 5,701,917 A | 12/1997 | Khouri |
| 5,707,499 A | 1/1998 | Joshi et al. |
| 5,738,656 A | 4/1998 | Wagner |
| 5,759,570 A | 6/1998 | Arnold |
| 5,795,584 A | 8/1998 | Totakura et al. |
| 5,797,844 A | 8/1998 | Yoshioka et al. |
| 5,797,894 A | 8/1998 | Cadieux et al. |
| 5,852,126 A | 12/1998 | Barnard et al. |
| 5,885,237 A | 3/1999 | Kadash et al. |
| 5,894,608 A | 4/1999 | Birbara |
| 5,910,150 A | 6/1999 | Saadat |
| 5,914,282 A | 6/1999 | Dunshee et al. |
| 5,928,265 A | 7/1999 | Fleischmann |
| 5,964,723 A | 10/1999 | Augustine |
| 6,071,267 A | 6/2000 | Zamierowski |
| 6,117,111 A | 9/2000 | Fleischmann |
| 6,121,508 A | 9/2000 | Bischof et al. |
| 6,142,982 A | 11/2000 | Hunt et al. |
| 6,149,614 A | 11/2000 | Dunshee et al. |
| 6,252,129 B1 | 6/2001 | Coffee |
| 6,264,976 B1 | 7/2001 | Heinecke et al. |
| 6,291,050 B1 | 9/2001 | Cree et al. |
| 6,345,623 B1 | 2/2002 | Heaton et al. |
| 6,391,294 B1 | 5/2002 | Dettmar et al. |
| 6,398,761 B1 | 6/2002 | Bills et al. |
| 6,406,447 B1 | 6/2002 | Thrash et al. |
| 6,420,622 B1 | 7/2002 | Johnston et al. |
| 6,458,109 B1 | 10/2002 | Henley et al. |
| 6,461,467 B2 | 10/2002 | Blatchford et al. |
| 6,471,685 B1 | 10/2002 | Johnson |
| 6,479,073 B1 | 11/2002 | Lucast et al. |
| 6,486,285 B2 | 11/2002 | Fujita |
| 6,566,575 B1 | 5/2003 | Stickels et al. |
| 6,607,799 B1 | 8/2003 | Heinecke et al. |
| 6,626,891 B2 | 9/2003 | Ohmstede |
| 6,629,774 B1 | 10/2003 | Gruendeman |
| 6,648,862 B2 | 11/2003 | Watson |
| 6,685,681 B2 | 2/2004 | Lockwood et al. |
| 6,752,794 B2 | 6/2004 | Lockwood et al. |
| 6,755,807 B2 | 6/2004 | Risk, Jr. et al. |
| 6,800,074 B2 | 10/2004 | Henley et al. |
| 6,824,533 B2 | 11/2004 | Risk, Jr. et al. |
| 6,838,589 B2 | 1/2005 | Liedtke et al. |
| 6,855,135 B2 | 2/2005 | Lockwood et al. |
| 6,878,857 B1 | 4/2005 | Chihani et al. |
| 6,903,243 B1 | 6/2005 | Burton |
| 6,936,037 B2 | 8/2005 | Bubb et al. |
| 6,951,553 B2 | 10/2005 | Bubb et al. |
| D515,701 S | 2/2006 | Horhota et al. |
| 6,994,702 B1 | 2/2006 | Johnson |
| 6,994,904 B2 | 2/2006 | Joseph et al. |
| 7,004,915 B2 | 2/2006 | Boynton et al. |
| 7,005,143 B2 | 2/2006 | Abuelyaman et al. |

(56) References Cited

U.S. PATENT DOCUMENTS

| | | |
|---|---|---|
| 7,048,818 B2 | 5/2006 | Krantz et al. |
| 7,070,580 B2 | 7/2006 | Nielsen |
| 7,070,584 B2 | 7/2006 | Johnson et al. |
| 7,108,683 B2 | 9/2006 | Zamierowski |
| 7,128,735 B2 | 10/2006 | Weston |
| 7,183,454 B1 | 2/2007 | Rosenberg |
| 7,195,624 B2 | 3/2007 | Lockwood et al. |
| 7,198,046 B1 | 4/2007 | Argenta et al. |
| 7,273,054 B2 | 9/2007 | Heaton et al. |
| 7,276,247 B2 | 10/2007 | Fansler et al. |
| 7,279,612 B1 | 10/2007 | Heaton et al. |
| 7,285,576 B2 | 10/2007 | Hyde et al. |
| 7,338,482 B2 | 3/2008 | Lockwood et al. |
| 7,381,859 B2 | 6/2008 | Hunt et al. |
| 7,442,849 B2 | 10/2008 | Heinecke |
| 7,485,112 B2 | 2/2009 | Karpowicz et al. |
| 7,503,910 B2 | 3/2009 | Adahan |
| 7,520,872 B2 | 4/2009 | Biggie et al. |
| 7,524,315 B2 | 4/2009 | Blott et al. |
| 7,531,711 B2 | 5/2009 | Sigurjonsson et al. |
| 7,534,927 B2 | 5/2009 | Lockwood et al. |
| 7,569,742 B2 | 8/2009 | Haggstrom et al. |
| 7,585,554 B2 | 9/2009 | Johnson et al. |
| 7,586,019 B2 | 9/2009 | Oelund et al. |
| 7,605,298 B2 | 10/2009 | Bechert et al. |
| 7,611,500 B1 | 11/2009 | Lina et al. |
| 7,615,036 B2 | 11/2009 | Joshi et al. |
| 7,622,629 B2 | 11/2009 | Aali |
| 7,625,362 B2 | 12/2009 | Boehringer et al. |
| 7,645,269 B2 | 1/2010 | Zamierowski |
| 7,651,484 B2 | 1/2010 | Heaton et al. |
| 7,678,102 B1 | 3/2010 | Heaton |
| 7,686,785 B2 | 3/2010 | Boehringer et al. |
| 7,699,831 B2 | 4/2010 | Bengtson et al. |
| 7,700,819 B2 | 4/2010 | Ambrosio et al. |
| 7,717,313 B2 | 5/2010 | Criscuolo et al. |
| 7,718,249 B2 | 5/2010 | Russell et al. |
| 7,723,560 B2 | 5/2010 | Lockwood et al. |
| 7,745,681 B1 | 6/2010 | Ferguson |
| 7,749,531 B2 | 7/2010 | Booher |
| 7,754,937 B2 | 7/2010 | Boehringer et al. |
| 7,758,554 B2 | 7/2010 | Lina et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,775,998 B2 | 8/2010 | Riesinger |
| 7,776,028 B2 | 8/2010 | Miller et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,803,980 B2 | 9/2010 | Griffiths et al. |
| 7,815,616 B2 | 10/2010 | Boehringer et al. |
| 7,846,141 B2 | 12/2010 | Weston |
| 7,857,806 B2 | 12/2010 | Karpowicz et al. |
| 7,862,718 B2 | 1/2011 | Doyen et al. |
| 7,880,050 B2 | 2/2011 | Robinson et al. |
| 7,896,823 B2 | 3/2011 | Mangrum et al. |
| 7,896,856 B2 | 3/2011 | Petrosenko et al. |
| 7,910,791 B2 | 3/2011 | Coffey |
| 7,922,703 B2 | 4/2011 | Riesinger |
| 7,942,866 B2 | 5/2011 | Radl et al. |
| 7,951,124 B2 | 5/2011 | Boehringer et al. |
| 7,959,624 B2 | 6/2011 | Riesinger |
| 7,976,519 B2 | 7/2011 | Bubb et al. |
| 7,976,533 B2 | 7/2011 | Larsson |
| 7,981,098 B2 | 7/2011 | Boehringer et al. |
| 8,002,313 B2 | 8/2011 | Singh et al. |
| 8,008,538 B2 | 8/2011 | Ugander et al. |
| 8,021,347 B2 | 9/2011 | Vitaris et al. |
| 8,057,449 B2 | 11/2011 | Sanders et al. |
| 8,061,360 B2 | 11/2011 | Locke et al. |
| 8,062,331 B2 | 11/2011 | Zamierowski |
| 8,083,712 B2 | 12/2011 | Biggie et al. |
| 8,097,272 B2 | 1/2012 | Addison |
| 8,100,887 B2 | 1/2012 | Weston et al. |
| 8,105,295 B2 | 1/2012 | Blott et al. |
| 8,128,607 B2 | 3/2012 | Hu et al. |
| 8,129,580 B2 | 3/2012 | Wilkes et al. |
| 8,133,211 B2 | 3/2012 | Cavanaugh, II et al. |
| 8,147,468 B2 | 4/2012 | Barta et al. |
| 8,148,596 B2 | 4/2012 | Miau et al. |
| 8,152,785 B2 | 4/2012 | Vitaris |
| 8,158,844 B2 | 4/2012 | McNeil |
| 8,162,907 B2 | 4/2012 | Heagle |
| 8,168,848 B2 | 5/2012 | Lockwood et al. |
| 8,187,237 B2 | 5/2012 | Seegert |
| 8,188,331 B2 | 5/2012 | Barta et al. |
| 8,192,409 B2 | 6/2012 | Hardman et al. |
| 8,197,467 B2 | 6/2012 | Heaton et al. |
| 8,202,261 B2 | 6/2012 | Kazala, Jr. et al. |
| 8,231,580 B2 | 7/2012 | Hansen et al. |
| 8,235,939 B2 | 8/2012 | Johnson et al. |
| 8,241,261 B2 | 8/2012 | Randolph et al. |
| 8,246,606 B2 | 8/2012 | Stevenson et al. |
| 8,267,908 B2 | 9/2012 | Coulthard |
| 8,282,611 B2 | 10/2012 | Weston |
| 8,298,200 B2 | 10/2012 | Vess et al. |
| 8,350,115 B2 | 1/2013 | Heaton et al. |
| 8,361,043 B2 | 1/2013 | Hu et al. |
| 8,372,049 B2 | 2/2013 | Jaeb et al. |
| 8,376,972 B2 | 2/2013 | Fleischmann |
| 8,382,731 B2 | 2/2013 | Johannison |
| 8,399,730 B2 | 3/2013 | Kazala, Jr. et al. |
| 8,409,170 B2 | 4/2013 | Locke et al. |
| 8,439,893 B2 | 5/2013 | Wakabayashi |
| 8,506,554 B2 | 8/2013 | Adahan |
| 8,513,481 B2 | 8/2013 | Gergely et al. |
| 8,545,466 B2 | 10/2013 | Andresen et al. |
| 8,568,386 B2 | 10/2013 | Malhi |
| 8,608,776 B2 | 12/2013 | Coward et al. |
| 8,623,047 B2 | 1/2014 | Cornet et al. |
| 8,663,198 B2 | 3/2014 | Buan et al. |
| 8,690,845 B2 | 4/2014 | Long et al. |
| 8,721,629 B2 | 5/2014 | Hardman et al. |
| 8,734,410 B2 | 5/2014 | Hall et al. |
| 8,771,244 B2 | 7/2014 | Eckstein et al. |
| 8,795,800 B2 | 8/2014 | Evans |
| 8,801,684 B2 | 8/2014 | Walti et al. |
| 8,814,842 B2 | 8/2014 | Coulthard et al. |
| 8,843,327 B2 | 9/2014 | Vernon-Harcourt et al. |
| 8,870,837 B2 | 10/2014 | Locke et al. |
| 8,926,593 B2 | 1/2015 | Croizat et al. |
| 8,951,235 B2 | 2/2015 | Allen et al. |
| 8,961,481 B2 | 2/2015 | Hu et al. |
| 9,033,942 B2 | 5/2015 | Vess |
| 9,050,398 B2 | 6/2015 | Armstrong et al. |
| 9,061,095 B2 | 6/2015 | Adie et al. |
| RE45,864 E | 1/2016 | Peron |
| 9,227,000 B2 | 1/2016 | Fink et al. |
| D755,980 S | 5/2016 | Jakobsen et al. |
| 9,375,521 B2 | 6/2016 | Hudspeth et al. |
| 9,381,283 B2 | 7/2016 | Adams et al. |
| 9,421,309 B2 | 8/2016 | Robinson et al. |
| 9,474,654 B2 | 10/2016 | Heagle et al. |
| RE46,289 E | 1/2017 | Peron |
| 9,539,373 B2 | 1/2017 | Jones et al. |
| 9,642,750 B2 | 5/2017 | Albert et al. |
| 9,681,993 B2 | 6/2017 | Wu et al. |
| 9,877,872 B2 | 1/2018 | Mumby et al. |
| 9,907,703 B2 | 3/2018 | Allen et al. |
| RE46,825 E | 5/2018 | Heagle |
| 10,065,030 B2 | 9/2018 | Kantrowitz et al. |
| 10,076,594 B2 | 9/2018 | Collinson et al. |
| 10,105,471 B2 | 10/2018 | Weston |
| 10,532,137 B2 | 1/2020 | Pratt et al. |
| 10,548,777 B2 | 2/2020 | Locke et al. |
| 11,596,555 B2 | 3/2023 | Dutta et al. |
| 2001/0034223 A1 | 10/2001 | Rieser et al. |
| 2002/0002209 A1 | 1/2002 | Mork |
| 2003/0125646 A1 | 7/2003 | Whitlock |
| 2003/0171675 A1 | 9/2003 | Rosenberg |
| 2003/0225347 A1 | 12/2003 | Argenta et al. |
| 2004/0039415 A1 | 2/2004 | Zamierowski |
| 2004/0054338 A1 | 3/2004 | Bybordi et al. |

(56) References Cited

U.S. PATENT DOCUMENTS

| | | |
|---|---|---|
| 2004/0057855 A1 | 3/2004 | Gerlach et al. |
| 2005/0020955 A1 | 1/2005 | Sanders et al. |
| 2005/0065484 A1 | 3/2005 | Watson, Jr. |
| 2005/0273066 A1 | 12/2005 | Wittmann |
| 2006/0009744 A1 | 1/2006 | Erdman et al. |
| 2006/0036221 A1 | 2/2006 | Watson, Jr. |
| 2007/0032763 A1 | 2/2007 | Vogel |
| 2007/0040454 A1 | 2/2007 | Freudenberger et al. |
| 2007/0255194 A1 | 11/2007 | Gudnason et al. |
| 2008/0031748 A1 | 2/2008 | Ihle et al. |
| 2008/0033325 A1 | 2/2008 | Van der Hulst |
| 2008/0103489 A1 | 5/2008 | Dahners |
| 2008/0132821 A1 | 6/2008 | Propp et al. |
| 2008/0161778 A1 | 7/2008 | Steward |
| 2008/0208147 A1 | 8/2008 | Argenta et al. |
| 2008/0243096 A1 | 10/2008 | Svedman |
| 2008/0275409 A1 | 11/2008 | Kane et al. |
| 2008/0281281 A1 | 11/2008 | Meyer et al. |
| 2008/0287892 A1 | 11/2008 | Khan et al. |
| 2008/0300578 A1 | 12/2008 | Freedman |
| 2008/0306456 A1 | 12/2008 | Riesinger |
| 2009/0099519 A1 | 4/2009 | Kaplan |
| 2009/0125004 A1 | 5/2009 | Shen et al. |
| 2009/0137973 A1 | 5/2009 | Karpowicz et al. |
| 2009/0157016 A1 | 6/2009 | Adahan |
| 2009/0157024 A1 | 6/2009 | Song |
| 2009/0171288 A1 | 7/2009 | Wheeler |
| 2009/0234306 A1 | 9/2009 | Vitaris |
| 2009/0264838 A1 | 10/2009 | Livne et al. |
| 2009/0281526 A1 | 11/2009 | Kenny et al. |
| 2009/0287133 A1 | 11/2009 | LaGreca, Sr. |
| 2009/0287181 A1 | 11/2009 | Kagan |
| 2009/0293887 A1 | 12/2009 | Wilkes et al. |
| 2009/0299251 A1 | 12/2009 | Buan |
| 2009/0299257 A1 | 12/2009 | Long et al. |
| 2009/0299306 A1 | 12/2009 | Buan |
| 2009/0299308 A1 | 12/2009 | Kazala, Jr. et al. |
| 2009/0299340 A1 | 12/2009 | Kazala, Jr. et al. |
| 2010/0000524 A1 | 1/2010 | Ohbi |
| 2010/0030178 A1 | 2/2010 | MacMeccan et al. |
| 2010/0069850 A1 | 3/2010 | Fabo |
| 2010/0069858 A1 | 3/2010 | Olson |
| 2010/0069863 A1 | 3/2010 | Olson |
| 2010/0069886 A1 | 3/2010 | Wilkes |
| 2010/0094234 A1 | 4/2010 | Ramella et al. |
| 2010/0106106 A1 | 4/2010 | Heaton et al. |
| 2010/0106108 A1 | 4/2010 | Hirsch |
| 2010/0106121 A1 | 4/2010 | Holm |
| 2010/0106188 A1 | 4/2010 | Heaton et al. |
| 2010/0125258 A1 | 5/2010 | Coulthard et al. |
| 2010/0160901 A1 | 6/2010 | Hu et al. |
| 2010/0168692 A1 | 7/2010 | Collins |
| 2010/0191197 A1 | 7/2010 | Braga et al. |
| 2010/0191198 A1 | 7/2010 | Heagle |
| 2010/0210986 A1 | 8/2010 | Sanders et al. |
| 2010/0249733 A9 | 9/2010 | Blott et al. |
| 2010/0256545 A1 | 10/2010 | Aali et al. |
| 2010/0259406 A1 | 10/2010 | Caso et al. |
| 2010/0262091 A1 | 10/2010 | Larsson |
| 2010/0268128 A1 | 10/2010 | Randolph |
| 2010/0318052 A1 | 12/2010 | Ha et al. |
| 2010/0324516 A1 | 12/2010 | Braga et al. |
| 2011/0004172 A1 | 1/2011 | Eckstein et al. |
| 2011/0028919 A1 | 2/2011 | Johnnison et al. |
| 2011/0092927 A1 | 4/2011 | Wilkes et al. |
| 2011/0125110 A1 | 5/2011 | Cotton |
| 2011/0130712 A1 | 6/2011 | Topaz |
| 2011/0172582 A1 | 7/2011 | Darian |
| 2011/0172615 A2 | 7/2011 | Greener |
| 2011/0224631 A1 | 9/2011 | Simmons et al. |
| 2011/0245682 A1 | 10/2011 | Robinson et al. |
| 2012/0051945 A1 | 3/2012 | Orndorff et al. |
| 2012/0302976 A1 | 11/2012 | Locke et al. |
| 2012/0310189 A1 | 12/2012 | Wang et al. |
| 2013/0030395 A1 | 1/2013 | Croizat et al. |
| 2013/0066365 A1 | 3/2013 | Belson et al. |
| 2013/0253453 A1 | 9/2013 | Olson |
| 2013/0296762 A1 | 11/2013 | Toth |
| 2013/0310809 A1* | 11/2013 | Armstrong ........ A61F 13/00068 285/260 |
| 2014/0121615 A1 | 5/2014 | Locke et al. |
| 2014/0194835 A1 | 7/2014 | Ehlert |
| 2014/0236108 A1 | 8/2014 | Heaton |
| 2014/0343520 A1 | 11/2014 | Bennett et al. |
| 2015/0018785 A1 | 1/2015 | Vess et al. |
| 2015/0141941 A1* | 5/2015 | Allen ................. A61M 1/79 604/319 |
| 2015/0190286 A1 | 7/2015 | Allen et al. |
| 2015/0231021 A1 | 8/2015 | Smith et al. |
| 2015/0343194 A1 | 12/2015 | Armstrong et al. |
| 2015/0359951 A1 | 12/2015 | Andersen et al. |
| 2016/0106892 A1* | 4/2016 | Hartwell ............ A61M 3/0279 604/304 |
| 2016/0144084 A1 | 5/2016 | Collinson et al. |
| 2016/0339158 A1* | 11/2016 | Collinson .......... A61F 13/0206 |
| 2017/0035617 A1 | 2/2017 | Albert et al. |
| 2019/0343687 A1 | 11/2019 | Locke et al. |

FOREIGN PATENT DOCUMENTS

| | | |
|---|---|---|
| DE | 202010009148 U1 | 9/2010 |
| EP | 0340018 A2 | 11/1989 |
| EP | 0325771 B1 | 9/1993 |
| EP | 0692987 B1 | 10/1997 |
| EP | 0853950 A1 | 7/1998 |
| EP | 0777504 B1 | 10/1998 |
| EP | 1018967 A1 | 7/2000 |
| EP | 1088569 A2 | 4/2001 |
| EP | 1129734 A2 | 9/2001 |
| EP | 0880953 B1 | 10/2003 |
| EP | 1219311 B1 | 7/2004 |
| EP | 1440667 A1 | 7/2004 |
| EP | 1448261 A1 | 8/2004 |
| EP | 1565219 A2 | 8/2005 |
| EP | 1637088 A2 | 3/2006 |
| EP | 0982015 B1 | 8/2006 |
| EP | 0620720 B2 | 11/2006 |
| EP | 1906903 A2 | 4/2008 |
| EP | 1920791 A2 | 5/2008 |
| EP | 1955887 A2 | 8/2008 |
| EP | 1993491 A2 | 11/2008 |
| EP | 2052750 A1 | 4/2009 |
| EP | 2138139 A2 | 12/2009 |
| EP | 1652549 B1 | 1/2010 |
| EP | 2172164 A1 | 4/2010 |
| EP | 2203137 A1 | 7/2010 |
| EP | 2218431 A2 | 8/2010 |
| EP | 2244217 A1 | 10/2010 |
| EP | 2244746 A2 | 11/2010 |
| EP | 2252247 A2 | 11/2010 |
| EP | 1578477 B1 | 9/2011 |
| EP | 2462908 A1 | 6/2012 |
| EP | 2628500 B1 | 5/2014 |
| FR | 1163907 A | 10/1958 |
| GB | 1255395 A | 12/1971 |
| GB | 2307180 A | 5/1997 |
| GB | 2336546 A | 10/1999 |
| GB | 2344531 B | 7/2000 |
| GB | 2356148 A | 5/2001 |
| GB | 2431351 A | 4/2007 |
| GB | 2468905 A | 9/2010 |
| JP | H04503625 A | 7/1992 |
| JP | 2001314479 A | 11/2001 |
| WO | WO-8300742 A1 | 3/1983 |
| WO | WO-9216245 A1 | 10/1992 |
| WO | WO-9421207 A2 | 9/1994 |
| WO | WO-9423678 A1 | 10/1994 |
| WO | WO-0007653 A1 | 2/2000 |
| WO | WO-0061206 A1 | 10/2000 |
| WO | WO-0185228 A2 | 11/2001 |
| WO | WO-02070040 A1 | 9/2002 |
| WO | WO-02092783 A2 | 11/2002 |
| WO | WO-03101508 A2 | 12/2003 |
| WO | WO-2004041064 A2 | 5/2004 |

(56) References Cited

FOREIGN PATENT DOCUMENTS

| | | |
|---|---|---|
| WO | WO-2004077387 A1 | 9/2004 |
| WO | WO-2005016179 A2 | 2/2005 |
| WO | WO-2005025447 A2 | 3/2005 |
| WO | WO-2005046760 A1 | 5/2005 |
| WO | WO-2005046761 A1 | 5/2005 |
| WO | WO-2005046762 A1 | 5/2005 |
| WO | WO-2005051461 A1 | 6/2005 |
| WO | WO-2005072789 A2 | 8/2005 |
| WO | WO-2005105174 A1 | 11/2005 |
| WO | WO-2005105175 A1 | 11/2005 |
| WO | WO-2005105176 A1 | 11/2005 |
| WO | WO-2005105179 A1 | 11/2005 |
| WO | WO-2005105180 A1 | 11/2005 |
| WO | WO-2005107842 A1 | 11/2005 |
| WO | WO-2005115497 A1 | 12/2005 |
| WO | WO-2005115523 A1 | 12/2005 |
| WO | WO-2005123170 A1 | 12/2005 |
| WO | WO-2006046060 A2 | 5/2006 |
| WO | WO-2006056408 A1 | 6/2006 |
| WO | WO-2006114637 A2 | 11/2006 |
| WO | WO-2006114638 A2 | 11/2006 |
| WO | WO-2006114648 A2 | 11/2006 |
| WO | WO-2007015964 A1 | 2/2007 |
| WO | WO-2007016590 A2 | 2/2007 |
| WO | WO-2007030598 A2 | 3/2007 |
| WO | WO-2007030599 A2 | 3/2007 |
| WO | WO-2007031757 A1 | 3/2007 |
| WO | WO-2007031762 A1 | 3/2007 |
| WO | WO-2007062024 A1 | 5/2007 |
| WO | WO-2007067685 A2 | 6/2007 |
| WO | WO-2007084792 A2 | 7/2007 |
| WO | WO-2007085396 A1 | 8/2007 |
| WO | WO-2007087808 A1 | 8/2007 |
| WO | WO-2007087809 A1 | 8/2007 |
| WO | WO-2007087811 A1 | 8/2007 |
| WO | WO-2007092397 A2 | 8/2007 |
| WO | WO-2007095180 A2 | 8/2007 |
| WO | WO-2007106590 A2 | 9/2007 |
| WO | WO-2007106591 A2 | 9/2007 |
| WO | WO-2007113597 A2 | 10/2007 |
| WO | WO-2007143060 A2 | 12/2007 |
| WO | WO-2008008032 A1 | 1/2008 |
| WO | WO-2008011774 A1 | 1/2008 |
| WO | WO-2008012278 A1 | 1/2008 |
| WO | WO-2008013896 A2 | 1/2008 |
| WO | WO-2008014358 A2 | 1/2008 |
| WO | WO-2008040020 A2 | 4/2008 |
| WO | WO-2008048527 A2 | 4/2008 |
| WO | WO-2008064502 A1 | 6/2008 |
| WO | WO-2008112304 A1 | 9/2008 |
| WO | WO-2008131895 A1 | 11/2008 |
| WO | WO-2008132215 A1 | 11/2008 |
| WO | WO-2008135997 A2 | 11/2008 |
| WO | WO-2008154158 A2 | 12/2008 |
| WO | WO-2009004370 A1 | 1/2009 |
| WO | WO-2009016603 A2 | 2/2009 |
| WO | WO-2009016605 A2 | 2/2009 |
| WO | WO-2009019229 A2 | 2/2009 |
| WO | WO-2009021047 A2 | 2/2009 |
| WO | WO-2009021353 A1 | 2/2009 |
| WO | WO-2009034322 A2 | 3/2009 |
| WO | WO-2009066105 A1 | 5/2009 |
| WO | WO-2009066106 A1 | 5/2009 |
| WO | WO-2009067711 A2 | 5/2009 |
| WO | WO-2009068665 A1 | 6/2009 |
| WO | WO-2009071926 A1 | 6/2009 |
| WO | WO-2009071929 A1 | 6/2009 |
| WO | WO-2009071932 A2 | 6/2009 |
| WO | WO-2009071935 A1 | 6/2009 |
| WO | WO-2009071948 A1 | 6/2009 |
| WO | WO-2009078790 A1 | 6/2009 |
| WO | WO-2009086580 A1 | 7/2009 |
| WO | WO-2009088925 A1 | 7/2009 |
| WO | WO-2009114624 A2 | 9/2009 |
| WO | WO-2009114760 A1 | 9/2009 |
| WO | WO-2009124100 A1 | 10/2009 |
| WO | WO-2009124473 A1 | 10/2009 |
| WO | WO-2009124548 A1 | 10/2009 |
| WO | WO-2009137194 A2 | 11/2009 |
| WO | WO-2009145703 A1 | 12/2009 |
| WO | WO-2009147402 A2 | 12/2009 |
| WO | WO-2010033271 A1 | 3/2010 |
| WO | WO-2010033272 A1 | 3/2010 |
| WO | WO-2010035017 A1 | 4/2010 |
| WO | WO-2010051073 A1 | 5/2010 |
| WO | WO-2010072395 A1 | 7/2010 |
| WO | WO-2010094957 A1 | 8/2010 |
| WO | WO-2010142959 A2 | 12/2010 |
| WO | WO 2011/087871 | 7/2011 |
| WO | WO-2011091052 A1 | 7/2011 |
| WO | WO-2011091952 A1 | 8/2011 |
| WO | WO-2011135285 A1 | 11/2011 |
| WO | WO-2011135286 A1 | 11/2011 |
| WO | WO-2011135287 A1 | 11/2011 |
| WO | WO-2011144888 A1 | 11/2011 |
| WO | WO-2012028842 A1 | 3/2012 |
| WO | WO 2012/087376 | 6/2012 |
| WO | WO-2012142002 A1 | 10/2012 |
| WO | WO-2013013938 A1 | 1/2013 |
| WO | WO-2013016239 A1 | 1/2013 |
| WO | WO-2013019438 A1 | 2/2013 |
| WO | WO-2013043972 A1 | 3/2013 |
| WO | WO-2013123005 A1 | 8/2013 |
| WO | WO-2014043238 A3 | 9/2014 |
| WO | WO-2017068364 A1 | 4/2017 |
| WO | WO 2017/087163 | 5/2017 |
| WO | WO-2017097834 A1 | 6/2017 |
| WO | WO 2018/167199 | 9/2018 |

OTHER PUBLICATIONS

Fleischmann W., et al., "Vacuum Sealing: Indication, Technique, And Results," Eur J Orthop Surg Traumatol, vol. 5, 1995, pp. 37-40.

Greer S.E., et al., "Techniques for Applying Subatmospheric Pressure Dressing to Wounds in Difficult Regions of Anatomy," JWOCN, vol. 26(5), Sep. 1999, pp. 250-253.

Info V.A.C. User Manual, KCI on Dec. 1, 2006 in 76 pages.

International Preliminary Report on Patentability for Application No. PCT/EP2019/068201, dated Jan. 21, 2021, 9 pages.

Jeter K F., et al., "Managing Draining Wounds and Fistulae: New and Established Methods," Chronic Wound Care, Chapter 27, 1990, pp. 240-246.

KCI, "V.A.C. therapy, GranuFoam Bridge Dressing Product," Brochure, 2009, 2 pages.

Landis E.M., et al., "The Effects of Alternate Suction and Pressure on Blood Flow to the Lower Extremities," Alternate Suction and Pressure, J Clin Invest, Sep. 1993, vol. 12 (5), pp. 925-961.

Mitchell R.N., et al., "Role of Stem Cells in Tissue Homeostasis," Pocket Companion to Robbins and Cotran Pathologic Basis of Disease, 7th Edition, 2006, p. 55 (3 pages).

Morykwas M.J., et al., "Nonsurgical Modalities to Enhance Healing and Care of Soft Tissue Wounds," Journal of the Southern Orthopaedic Association, vol. 6, No. 4, 1997, pp. 279-288.

International Search Report and Written Opinion, re PCT Application No. PCT/EP2019/068201, dated Sep. 24, 2019.

510K Filing K062227 by KCI USA, Inc. with the Food and Drug Administration on Sep. 27, 2006, 5 pages.

Expert Declaration by Carianne Nilsson for Post Grant Review of U.S. Pat. No. 9,642,750, dated Feb. 8, 2018, 13 pages.

Expert Declaration by Dr. Michael Helmus for Post Grant Review of U.S. Pat. No. 9,642,750, dated Feb. 9, 2018, 184 pages.

Images of SensaT.R.A.C. produced in 2016, filed in Post Grant Review of U.S. Pat. No. 9,642,750 on Feb. 9, 2018, in 5 pages.

"KCI—The Clinical Advantage", Presentation by KCI with English translation, 61 pages. (publication date unknown).

Kinetic Concepts, Inc., "510K filing K022011 by KCI with the Food and Drug Administration," Jun. 19, 2002, 5 pages.

News., "KCI Launches Next Generation Wound Care Therapy Systems", Imaging Technology News, Aug. 30, 2007, Retrieved

(56) References Cited

OTHER PUBLICATIONS from Internet URL: https://www.itnonline.com/content/kci-launches-next-generation-wound-car-etherapy-systems, 2 pages.

"SensaT.R.A.C.TM Technology—An Essential Component of V.A.C.® Therapy", KCI user's manual, Mar. 5, 2010, 2 pages.

The Wayback Machine, "Comfort advantages with AirX™," retrieved from http://web.archive.org/web/20090121000205/http://www.airx.eu:80/content/view/2/3/lang,en/, on Jan. 21, 2009, 1 page.

The Wayback Machine, "Moisture-Transporting Material," retrieved from http://web.archive.org/web/20090121001036/http://www.airx.eu/content/view/1/14/lang,en/, on Jan. 21, 2009, 1 page.

Trademark Prosecution History for SENSAT.R.A.C. filed in Post Grant Review of U.S. Pat. No. 9,642,750 on Feb. 9, 2018, in 112 pages.

"V.A.C. Freedom® and V.A.C. ATS® Therapy Systems—Active Healing by Designs", KCI product catalog, 2009, LIT 29-A-194, 4 pages.

Advantec MFS, Inc., "Membrane Filters" (catalog), retrieved from http://www.advantecmfs.com/catalog/filt/membrane.pdf, on Jan. 29, 2016, Copyright 2001-2011, 17 pages.

Hersle K., et al., "Uses of Dextranomer Absorbent Pads After Cryosurgery of Cutaneous Malignancies," The Journal of Dermatologic Surgery and Oncology, vol. 8, Jan. 1982, pp. 35-37.

Kendall ULTEC Hydrocolloid Dressing (4x4"), Product Ordering Page, web page downloaded on Jul. 13, 2014, 1 page.

Protz K., "Modern Wound Dressings Support the Healing Process," Wound care: Indications and Application, Geriatrie Journal, Apr. 2005, pp. 3333-3339 (17 pages with English translation).

Smith & Nephew, "PICO Single Use Negative Pressure Wound Therapy System," Spiral Booklet, Mar. 2011, 7 pages.

Technology Watch, May 1989, 1 page.

The Wayback Machine, "Comfort advantages with AirX™," Retrieved from the Internet: https://web.archive.org/web/20070714011844/http://www.air-x.net/content/view/2/3/lang/, on Jul. 14, 2007, 1 page.

The Wayback Machine, "Moisture-Transporting Material," Retrieved from the Internet: https://web.archive.org/web/20070714011837/http://www.air-x.net/content/view/1/2/lang/, on Jul. 14, 2007, 1 page.

* cited by examiner

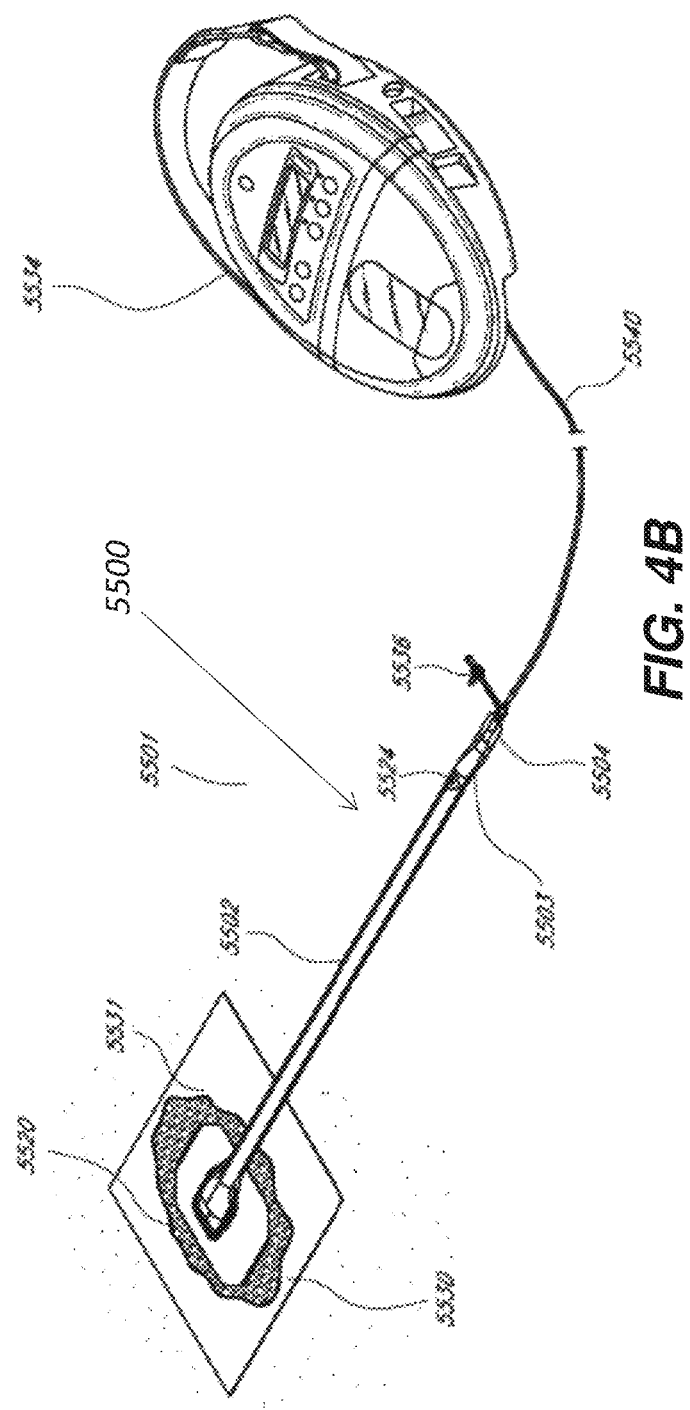

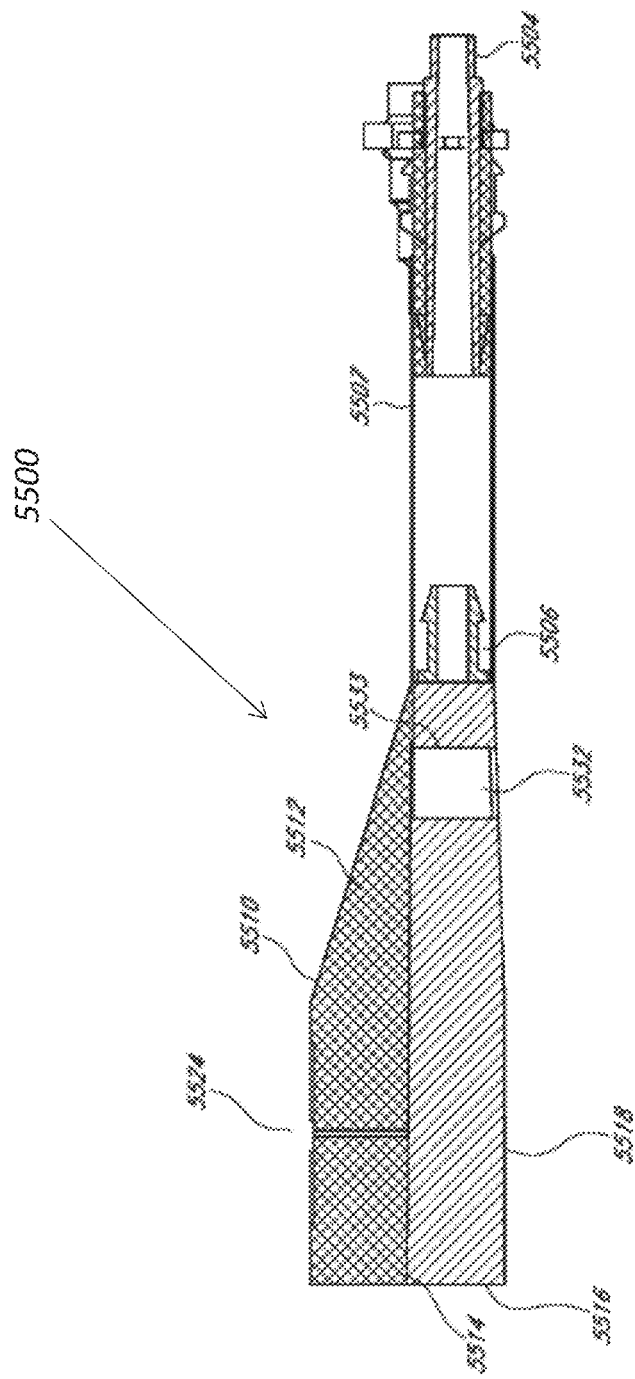

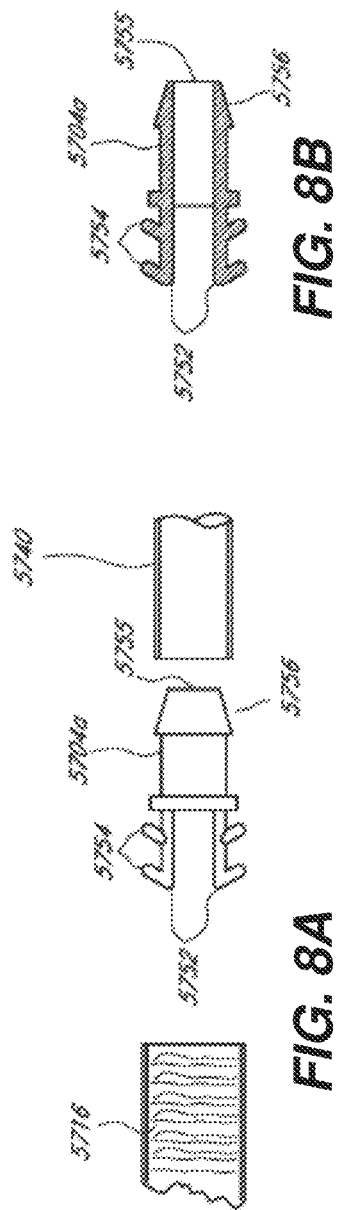

APPARATUSES AND METHODS FOR NEGATIVE PRESSURE WOUND THERAPY

INCORPORATION BY REFERENCE TO ANY PRIORITY APPLICATIONS

Any and all applications for which a foreign or domestic priority claim is identified in the Application Data Sheet as filed with the present application are hereby incorporated by reference and made a part of the present disclosure.

BACKGROUND

Field

Embodiments of the present disclosure relate to methods and apparatuses for dressing and treating a wound with reduced pressure therapy or topical negative pressure (TNP) therapy. In particular, but without limitation, embodiments disclosed herein relate to negative pressure therapy devices, methods for controlling the operation of TNP systems, and methods of using TNP systems.

Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure (TNP) therapy, sometimes referred to as vacuum assisted closure, negative pressure wound therapy (NPWT), or reduced pressure wound therapy, is widely recognized as a beneficial mechanism for improving the healing rate of a wound. Such therapy is applicable to a broad range of wounds such as incisional wounds, open wounds and abdominal wounds or the like.

TNP therapy assists in the closure and healing of wounds by reducing tissue oedema, encouraging blood flow, stimulating the formation of granulation tissue, removing excess exudates and may reduce bacterial load and, thus, infection to the wound. Furthermore, TNP therapy permits less outside disturbance of the wound and promotes more rapid healing.

SUMMARY

Embodiments of the invention disclosed herein are directed to apparatuses, systems, devices and methods for use in negative pressure wound therapy.

According to some embodiments, there is provided an apparatus to provide negative pressure to a wound site, the apparatus comprising:
  a top layer, a bottom layer and an intermediate layer, wherein each layer is constructed from a flexible, liquid impermeable material and is adhered to one another, wherein each of the layers has a proximal end and a distal end and an elongate portion extending therebetween;
  an upper fluid passage at least partially defined between the top layer and the intermediate layer, the upper fluid passage having a proximal end and a distal end, wherein the upper fluid passage comprises an upper channel spacer layer positioned between the upper and intermediate layers, and wherein the upper fluid passage is configured to provide air from an air leak toward the distal end of the upper fluid passage;
  a lower fluid passage at least partially defined between the intermediate and bottom layers, the lower fluid passage configured to be in fluid communication with a source of negative pressure, the lower fluid passage comprising a lower channel spacer layer positioned between the intermediate and lower film layers; and
  a first opening and a second opening in the distal end of the bottom layer, wherein the first opening is spaced apart from the second opening, wherein the first opening is fluidically connected to the upper fluid passage and the second opening is fluidically connected to the lower fluid passage.

The apparatus of the preceding paragraph or in other embodiments can include one or more of the following features. In some embodiments, the upper channel spacer layer may comprise foam and/or the lower channel spacer layer may comprise a 3D knitted or 3D fabric material. In some embodiments, each of the top layer and the bottom layer may have an enlarged distal end. The enlarged ends of the top and bottom layers may be rectangular and/or form a teardrop shape. In some embodiments, the bottom layer may be attached to an applicator and/or configured to be attached to a drape. The applicator may comprise two apertures placed directly beneath the first opening and the second opening. In some embodiments, the air leak may be disposed adjacent the proximal end of the upper fluid passage and/or the air leak may comprise a filter. In some embodiments, the upper fluid passage and the lower fluid passage may be fluidically separated from each other. The first opening may be closer to the distal end of the bottom layer than the second opening. The distal end of the intermediate layer may be proximal to the distal ends of the top and bottom layers. In some embodiments, the apparatus may further comprise a connector in fluid communication with the proximal end of the lower channel spacer layer.

According to some embodiments, there is provided an apparatus to provide negative pressure to a wound site, the apparatus comprising:
  an elongate bridge having a proximal end and a distal end, the elongate body comprising a first fluid passage configured to provide negative pressure to the wound site and a second fluid passage configured to provide an air leak toward the wound site; and
  an applicator at the distal end of the elongate bridge, the applicator comprising a first opening and a second opening spaced apart from the first opening;
  wherein the first fluid passage is fluidically connected to the first opening and the second fluid passage is fluidically connected to the second opening.

The apparatus of the preceding paragraph or in other embodiments can include one or more of the following features. In some embodiments, each of the first fluid passage and the second fluid passage may comprise a deformable spacer. The deformable spacer of the first fluid passage may comprise a 3D knitted or 3D fabric material and/or the deformable spacer layer of the second fluid passage comprises foam. In some embodiments, the second fluid passage may be placed above the first fluid passage. Alternatively, the first fluid passage and the second fluid passage may be placed side-by-side. In some embodiments, the first fluid passage and the second fluid passage may be fluidically separated from each other within the elongate bridge. The first fluid passage and the second fluid passage may be separated by a fluid impermeable layer. In some embodiments, the applicator may be configured to be attached to a drape. The first opening may be closer to the distal end of the applicator than the second opening. The apparatus may further comprise an adhesive disposed on a wound-facing side of the applicator. In some embodiments, air leak may be provided via an opening disposed adjacent the proximal end of the elongate bridge. The air leak may comprise a filter.

According to some embodiments, there is provided a method of operating a negative pressure wound therapy apparatus, the method comprising:

determining a total rate of flow in a fluid flow path fluidically coupling a negative pressure source to a wound dressing placed over a wound, wherein the wound dressing is fluidically connected to an air leak path configured to provide gas from a controlled air leak to the wound dressing, wherein the air leak path extends along the fluid flow path but is fluidically separated from the fluid flow path;

in response to monitoring the total rate of flow, providing an indication of at least one operating condition by:

providing an indication that a blockage condition exists in the fluid flow path in response to determining that the total rate of flow does not satisfy a flow threshold;

providing an indication that a normal operation condition exists in response to determining that the total rate of flow satisfies the flow threshold, wherein the method is performed by a controller of the negative pressure wound therapy apparatus.

The method of the preceding paragraph or in other embodiments can include one or more of the following features. In some embodiments, the flow threshold may correspond to an expected rate of flow in the fluid flow path. The expected rate of flow may correspond to the rate of flow in the fluid path under the normal operation condition. In some embodiments, determining the total rate of flow may comprise measuring a speed of a motor operating the negative pressure source. In some embodiments, the method may further comprise measuring a first plurality of motor speeds during a first period of time and averaging the first plurality of motor speeds, the average being indicative of the rate of flow.

According to some embodiments, there is provided a method of treating a wound, the method comprising:

providing a suction adapter comprising:

an elongate bridge portion having a proximal end and a distal end, the elongate bridge comprising a first fluid passage configured to provide negative pressure to a wound site and a second fluid passage configured to provide an air leak toward the wound site;

an applicator at the distal end of the elongate bridge, the applicator comprising a first opening and a second opening spaced apart from the first opening;

wherein the first fluid passage is fluidically connected to the first opening and the second fluid passage is fluidically connected to the second opening;

situating the first opening and the second opening of the applicator over one or more apertures in a drape covering the wound;

sealing the suction adapter to the drape; and applying negative pressure to the wound through the suction adapter, wherein air is drawn through the air leak toward the wound site, through the second opening, under the drape, and through the first opening to the first fluid passage.

The method of the preceding paragraph or in other embodiments can include one or more of the following features. In some embodiments, the one or more apertures in the drape may include a first aperture and a second aperture, and situating may comprise aligning the first opening of the applicator with the first aperture of the drape and the second opening of the applicator with the second aperture of the drape.

Other embodiments of an apparatus to provide negative pressure to a wound site, devices, kits and associated methods are described below.

BRIEF DESCRIPTION OF THE DRAWINGS

FIG. 4B illustrates the embodiment of FIG. 4A, with the flexible suction adapter having been placed over a wound.

FIG. 5D illustrates a close-up cutaway view of the proximal end of the flexible suction adapter of FIG. 2A.

FIGS. 8A-B illustrate an embodiment of a connector with two or more projections and that may be connected to a suction adapter illustrated in FIG. 5A.

DETAILED DESCRIPTION

Overview

Embodiments disclosed herein relate to apparatuses, systems, devices and methods of treating a wound with reduced pressure. As is used herein, reduced or negative pressure levels, such as −X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of −X mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (e.g., −40 mmHg is less than −60 mmHg). Negative pressure that is "more" or "greater" than −X mmHg corresponds to pressure that is further from atmospheric pressure (e.g., −80 mmHg is more than −60 mmHg). In some embodiments, local ambient atmospheric pressure is used as a reference point, and such local atmospheric pressure may not necessarily be, for example, 760 mmHg.

Embodiments of the present disclosure are generally applicable to use in topical negative pressure (TNP) or reduced pressure therapy systems. Briefly, negative pressure wound therapy assists in the closure and healing of many forms of "hard to heal" wounds by reducing tissue oedema, encouraging blood flow and granular tissue formation, or removing excess exudate and can reduce bacterial load (and thus infection risk). In addition, the therapy allows for less disturbance of a wound leading to more rapid healing. TNP therapy systems can also assist in the healing of surgically closed wounds by removing fluid. In some embodiments, TNP therapy helps to stabilize the tissue in the apposed position of closure. A further beneficial use of TNP therapy can be found in grafts and flaps where removal of excess fluid is important and close proximity of the graft to tissue is required in order to ensure tissue viability.

Negative Pressure System

Figure 1:
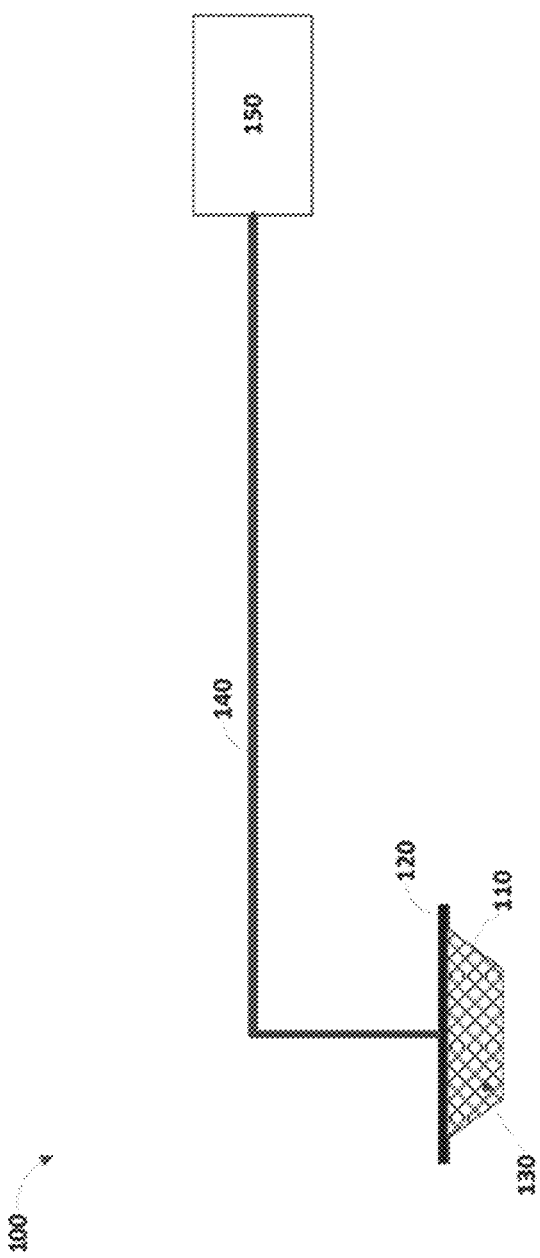
FIG. 1 illustrates a reduced pressure wound therapy system according to some embodiments.

FIG. 1 illustrates an embodiment of a negative or reduced pressure wound treatment (or TNP) system 100 including a wound filler 130 placed inside a wound cavity 110, the wound cavity sealed by a wound cover 120. The wound filler 130 in combination with the wound cover 120 can be referred to as wound dressing. A flow path 140, such as a single or multi lumen tube or conduit, is connected to the wound cover 120 with a negative pressure wound therapy device, for example pump assembly 150, configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing. The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110. The wound cover 120 and the wound filler 130 can be provided as a single article or an integrated single unit. In some embodiments, no wound filler is provided and the wound cover by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate. It will be appreciated that throughout this specification reference is made to a wound. In this sense it is to be understood that the term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, subacute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Some embodiments of the system are designed to operate without the use of an exudate canister. Some embodiments can be configured to support an exudate canister. In some embodiments, configuring the pump assembly 150 and tubing 140 so that the tubing 140 can be quickly and easily removed from the pump assembly 150 can facilitate or improve the process of dressing or pump changes, if necessary. Any of the pump embodiments disclosed herein can be configured to have any suitable connection between the tubing and the pump.

In some embodiments, the pump assembly 150 can be configured to deliver negative pressure of approximately −80 mmHg, or between about −20 mmHg and −200 mmHg.

Note that these pressures are relative to normal ambient atmospheric pressure thus, −200 mmHg would be about 560 mmHg in practical terms. The pressure range can be between about −40 mmHg and −150 mmHg. Alternatively a pressure range of up to −75 mmHg, up to −80 mmHg or over −80 mmHg can be used. Also a pressure range of below −75 mmHg can be used. Alternatively a pressure range of over approximately −100 mmHg, or even 150 mmHg, can be supplied by the pump assembly 150. In some embodiments, the pump assembly 150 is configured to provide continuous or intermittent negative pressure therapy. Continuous therapy can be delivered at above −25 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. Intermittent therapy can be delivered between low and high negative pressure setpoints. Low setpoint can be set at above 0 mmHg, 0 mmHg, −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, or below −180 mmHg. High setpoint can be set at above −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg, or below −200 mmHg. During intermittent therapy, negative pressure at low setpoint can be delivered for a first-time duration, and upon expiration of the first-time duration, negative pressure at high setpoint can be delivered for a second-time duration. Upon expiration of the second-time duration, negative pressure at low setpoint can be delivered. The first and second time durations can be same or different values. The first and second durations can be selected from the following range: less than 2 minutes, 2 minutes, 3 minutes, 4 minutes, 6 minutes, 8 minutes, 10 minutes, or greater than 10 minutes. In some embodiments, switching between low and high setpoints and vice versa can be performed according to a step waveform, square waveform, sinusoidal waveform, and the like.

In some embodiments, the TNP system 100 can include multiple wound dressings connected to the pump assembly 150. The performance and wound healing capabilities (such as, fluid management) of the TNP system with multiple wound dressings with the pump assembly 150 can be equivalent to or exceed that of a standard single wound dressing with single pump set-up.

In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (e.g., wound exudate) is drawn through the conduit 140, and can be stored in a canister. In some embodiments, fluid is absorbed by the wound filler 130 or one or more absorbent layers (not shown).

Wound dressings that may be utilized with the pump assembly and other embodiments of the present application include Renasys-F, Renasys-G, Renasys AB, and Pico Dressings available from Smith & Nephew. Any of the dressings described herein can be used with Smith and Nephew's Renasys Soft Port connector or interface between the dressing and the pump assembly. For example, the Renasys Soft Port connector can be positioned in the flow path 140 and serve as a port for the wound dressing. In other embodiments, other suitable wound dressings can be utilized.

Pump Assembly and Canister

Figure 2:
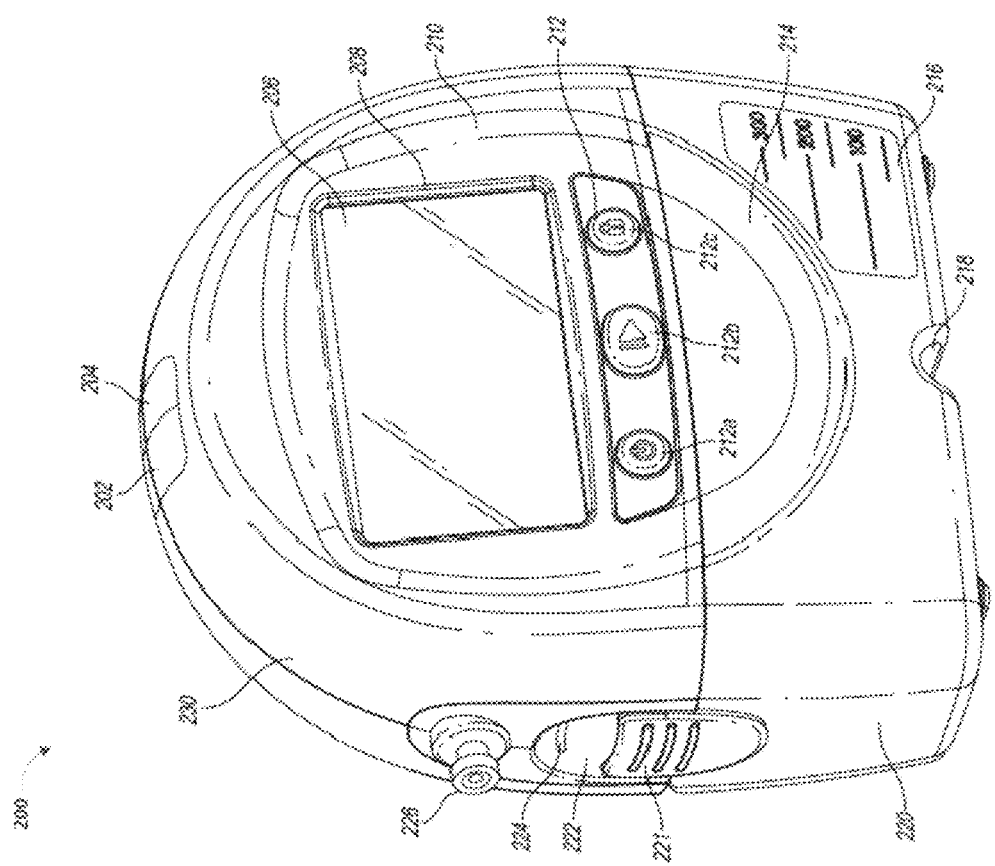
FIG. 2 illustrates a pump assembly and canister according to some embodiments.

FIG. 2 illustrates a front view 200 of a pump assembly 230 and canister 220 according to some embodiments. As is illustrated, the pump assembly 230 and the canister are connected, thereby forming a TNP device or system. The pump assembly 230 includes one or more indicators, such as visual indicator 202 configured to indicate alarms and visual indicator 204 configured to indicate status of the TNP system. The indicators 202 and 204 can be configured to alert a user, such as patient or medical care provider, to a variety of operating or failure conditions of the system, including alerting the user to normal or proper operating conditions, pump failure, power supplied to the pump or power failure, detection of a leak within the wound cover or flow pathway, suction blockage, no flow condition, canister full condition, or any other similar or suitable conditions or combinations thereof. The pump assembly 230 can include additional indicators. The pump assembly can use a single indicator or multiple indicators. Any suitable indicator can be used such as visual, audio, tactile indicator, and so on. The indicator 202 can be configured to signal alarm conditions, such as canister full, power low, conduit 140 disconnected, seal broken in the wound seal 120, and so on. The indicator 202 can be configured to display red flashing light to draw user's attention. The indicator 204 can be configured to signal status of the TNP system, such as therapy delivery is ok, leak detected, and so on. The indicator 204 can be configured to display one or more different colors of light, such as green, yellow, etc. For example, green light can be emitted when the TNP system is operating properly and yellow light can be emitted to indicate a warning.

The pump assembly 230 includes a display or screen 206 mounted in a recess 208 formed in a case of the pump assembly. The display 206 can be a touch screen display. The display 206 can support playback of audiovisual (AV) content, such as instructional videos. As explained herein, the display 206 can be configured to render a number of screens or graphical user interfaces (GUIs) for configuring, controlling, and monitoring the operation of the TNP system. The pump assembly 230 includes a gripping portion 210 formed in the case of the pump assembly. The gripping portion 210 can be configured to assist the user to hold the pump assembly 230, such as during removal of the canister 220. The canister 220 can be replaced with another canister, such as when the canister 220 has been filled with fluid.

The pump assembly 230 includes one or more keys or buttons 212 configured to allow the user to operate and monitor the operation of the TNP system. As is illustrated, there buttons 212a, 212b, and 212c are included. Button 212a can be configured as a power button to turn on/off the pump assembly 230. Button 212b can be configured as a play/pause button for the delivery of negative pressure therapy. For example, pressing the button 212b can cause therapy to start, and pressing the button 212b afterward can cause therapy to pause or end. Button 212c can be configured to lock the display 206 or the buttons 212. For instance, button 212c can be pressed so that the user does not unintentionally alter the delivery of the therapy. Button 212c can be depressed to unlock the controls. In other embodiments, additional buttons can be used or one or more of the illustrated buttons 212a, 212b, or 212c can be omitted. Multiple key presses or sequences of key presses can be used to operate the pump assembly 230.

The pump assembly 230 includes one or more latch recesses 222 formed in the cover. In the illustrated embodiment, two latch recesses 222 can be formed on the sides of the pump assembly 230. The latch recesses 222 can be configured to allow attachment and detachment of the canister 220 using one or more canister latches 221. The pump assembly 230 includes an air outlet 224 for allowing air removed from the wound cavity 110 to escape. Air entering the pump assembly can be passed through one or more suitable filters, such as antibacterial filters. This can maintain reusability of the pump assembly. The pump assembly 230 includes one or more strap mounts 226 for connecting a carry strap to the pump assembly 230 or for attaching a cradle. In the illustrated embodiment, two strap mounts 226 can be formed on the sides of the pump assembly 230. In some embodiments, various features are omitted or various additional features are added to the pump assembly 230.

The canister 220 is configured to hold fluid (e.g., exudate) removed from the wound cavity 110. The canister 220 includes one or more latches 221 for attaching the canister to the pump assembly 230. In the illustrated embodiment, the canister 220 includes two latches 221 on the sides of the canister. The exterior of the canister 220 can formed from frosted plastic so that the canister is substantially opaque and the contents of the canister and substantially hidden from plain view. The canister 220 includes a gripping portion 214 formed in a case of the canister. The gripping portion 214 can be configured to allow the user to hold the pump assembly 220, such as during removal of the canister from the apparatus 230. The canister 220 includes a substantially transparent window 216, which can also include graduations of volume. For example, the illustrated 300 mL canister 220 includes graduations of 50 mL, 100 mL, 150 mL, 200 mL, 250 mL, and 300 mL. Other embodiments of the canister can hold different volume of fluid and can include different graduation scale. For example, the canister can be an 800 mL canister. The canister 220 includes a tubing channel 218 for connecting to the conduit 140. In some embodiments, one or more of these features, such as the gripping portion 214, are omitted or various additional features are added to the canister 220. Any of the disclosed canisters may include or may omit a solidifier.

Electronics and Software

Figure 3:
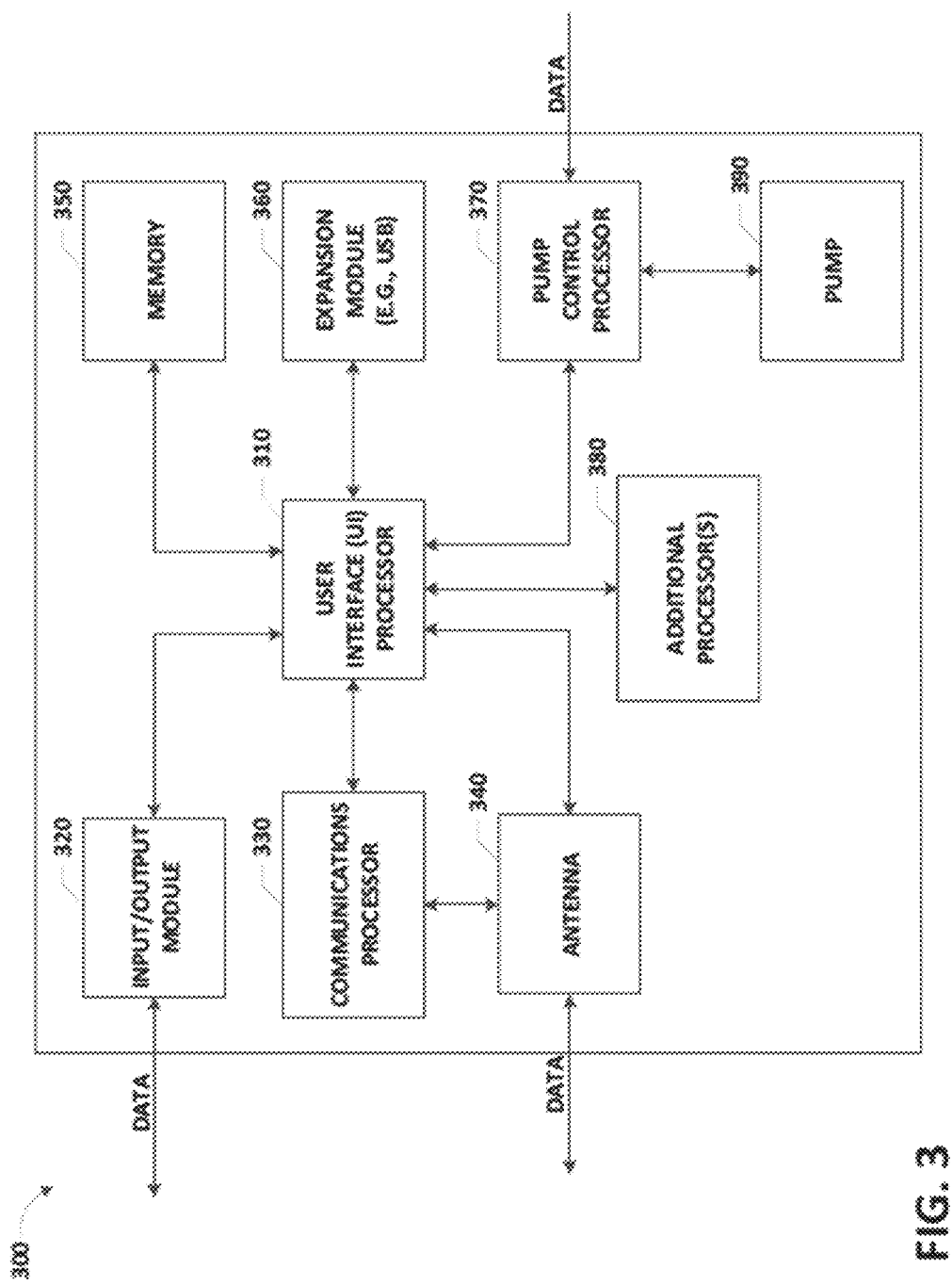
FIG. 3 illustrates an electrical component schematic of a pump assembly according to some embodiments.

FIG. 3 illustrates an electrical component schematic 300 of a pump assembly, such as the pump assembly 230, according to some embodiments. Electrical components can operate to accept user input, provide output to the user, operate the pump assembly and the TNP system, provide network connectivity, and so on. Electrical components can be mounted on one or more printed circuit boards (PCBs). As is illustrated, the pump assembly can include multiple processors. It may be advantageous to utilize multiple processors in order to allocate or assign various tasks to different processors. A first processor can be responsible for user activity and a second processor can be responsible for controlling the pump. This way, the activity of controlling the pump, which may necessitate a higher level of responsiveness (corresponding to higher risk level), can be offloaded to a dedicated processor and, thereby, will not be interrupted by user interface tasks, which may take longer to complete because of interactions with the user.

The pump assembly can include a user interface processor or controller 310 configured to operate one or more components for accepting user input and providing output to the user, such as the display 206, buttons 212, etc. Input to the pump assembly and output from the pump assembly can controlled by an input/output (I/O) module 320. For example, the I/O module can receive data from one or more ports, such as serial, parallel, hybrid ports, and the like. The processor 310 also receives data from and provides data to one or more expansion modules 360, such as one or more USB ports, SD ports, Compact Disc (CD) drives, DVD drives, FireWire ports, Thunderbolt ports, PCI Express ports, and the like. The processor 310, along with other controllers or processors, stores data in one or more memory modules 350, which can be internal or external to the processor 310. Any suitable type of memory can be used, including volatile or non-volatile memory, such as RAM, ROM, magnetic memory, solid-state memory, Magnetoresistive random-access memory (MRAM), and the like.

In some embodiments, the processor 310 can be a general-purpose controller, such as a low-power processor. In other embodiments, the processor 310 can be an application specific processor. The processor 310 can be configured as a "central" processor in the electronic architecture of the pump assembly, and the processor 310 can coordinate the activity of other processors, such as a pump control processor 370, communications processor 330, and one or more additional processors 380 (e.g., processor for controlling the display 206, processor for controlling the buttons 212, etc.). The processor 310 can run a suitable operating system, such as a Linux, Windows CE, VxWorks, etc.

The pump control processor 370 can be configured to control the operation of a negative pressure source or pump 390. The pump 390 can be a suitable pump, such as a diaphragm pump, peristaltic pump, rotary pump, rotary vane pump, scroll pump, screw pump, liquid ring pump, pump (for example, diaphragm pump) operated by a piezoelectric transducer, voice coil pump, and the like. The pump control processor 370 can measure pressure in a fluid flow path, using data received from one or more pressure sensors, calculate the rate of fluid flow, and control the pump. The pump control processor 370 can control an actuator, such as a pump motor, so that a desired level of negative pressure is achieved in the wound cavity 110. The desired level of negative pressure can be pressure set or selected by the user. In various embodiments, the pump control processor 370 controls the pump actuator (e.g., pump motor) using pulse-width modulation (PWM). A control signal for driving the pump actuator can be a 0-100% duty cycle PWM signal. The pump control processor 370 can perform flow rate calculations and detect various conditions in a flow path. The pump control processor 370 can communicate information to the processor 310. The pump control processor 370 can include internal memory or can utilize memory 350. The pump control processor 370 can be a low-power processor.

A communications processor 330 can be configured to provide wired or wireless connectivity. The communications processor 330 can utilize one or more antennas 340 for sending and receiving data. The communications processor 330 can provide one or more of the following types of connections: Global Positioning System (GPS) technology, cellular connectivity (e.g., 2G, 3G, LTE, 4G), Wi-Fi connectivity, Internet connectivity, and the like. Connectivity can be used for various activities, such as pump assembly location tracking, asset tracking, compliance monitoring, remote selection, uploading of logs, alarms, and other operational data, and adjustment of therapy settings, upgrading of software or firmware, and the like. The communications processor 330 can provide dual GPS/cellular functionality. Cellular functionality can, for example, be 3G functionality. In such cases, if the GPS module is not able to establish satellite connection due to various factors including atmospheric conditions, building or terrain interference, satellite geometry, and so on, the device location can be determined using the 3G network connection, such as by using cell identification, triangulation, forward link timing, and the like. The pump assembly can include a SIM card, and SIM-based positional information can be obtained.

The communications processor 330 can communicate information to the processor 310. The communications processor 330 can include internal memory or can utilize memory 350. The communications processor 330 can be a low-power processor.

In some embodiments, the pump assembly can track and store various data, such as one or more of positioning data, therapy parameters, logs, device data, and so on. The pump assembly can track and log therapy and other operational data. Data can be stored, for example, in the memory 350.

In some embodiments, using the connectivity provided by the communications processor 330, the device can upload any of the data stored, maintained, or tracked by the pump assembly. For example, the following information can be uploaded to a remote computer or server: activity log(s), which includes therapy delivery information, such as therapy duration, alarm log(s), which includes alarm type and time of occurrence; error log, which includes internal error information, transmission errors, and the like; therapy duration information, which can be computed hourly, daily, and the like; total therapy time, which includes therapy duration from first applying a particular therapy program or programs; lifetime therapy information; device information, such as the serial number, software version, battery level, etc.; device location information; patient information; and so on. The device can also download various operational data, such as therapy selection and parameters, firmware and software patches and upgrades, and the like. The pump assembly can provide Internet browsing functionality using one or more browser programs, mail programs, application software (e.g., apps), etc.

In some embodiments, the communications processor 330 can use the antenna 340 to communicate a location of the pump assembly, such as a location of a housing of the pump assembly, to other devices in the proximity (for example, within 10, 20, or 50 meters and the like) of the pump assembly. The communications processor 330 can perform one-way or two-way communication with the other devices depending on the implementation. The communications transmitted by the communications processor 330 can include identifying information to uniquely identify the pump assembly relative to one or more other pump assemblies also in the proximity of the pump assembly. For example, identifying information can include a serial number or a value derived from the serial number. The signal strength of the transmitted communications by the communications processor 330 can be controlled (for example, maintained at a constant or substantially constant level) to enable another device to determine a distance to the pump assembly, such as a distance between the device and the pump assembly.

In some embodiments, the communications processor 330 can communicate with other devices in the proximity of the pump assembly so that the communications processor 330 can itself determine a distance from the pump assembly to the other devices. The communications processor 330, in such embodiments, can track and store the distance from the pump assembly to the other devices or indications of change in the distance over time, and the communications processor 330 can later provide this information to the other devices. For instance, the communications processor 330 can determine a duration of time during which the pump assembly has been removed from a coverage area of a device and subsequently report this time to the device upon being returned to the coverage area.

Flexible Suction Adapter

FIGS. 4A-6 illustrate embodiments of a negative pressure wound treatment system 5501 similar to the embodiment illustrated in FIG. 1. Here, the system 5501 may comprise a flexible suction adapter 5500 having a bridge portion 5502 with a proximal end 5503 and a distal end 5505, and an applicator 5520 at the distal end 5505 of the bridge portion 5502 forming the flexible suction adapter 5500. A connector 5504 is preferably disposed at the proximal end 5503 of the bridge portion 5502, so as to connect to at least one of the channels 5512 and/or 5516, as shown in FIG. 4B. A cap 5536 may be provided with the system 5501 (and can in some cases, as illustrated, be attached to the connector 5504). The cap 5536 can be useful in preventing fluids from leaking out of the proximal end 5503. The system 5501 may include a source of negative pressure such as a pump or negative pressure unit 5534 capable of supplying negative pressure. The pump also preferably comprises a canister or other container for the storage of wound exudates and other fluids that may be removed from the wound. In some embodiments, this pump 5534 may be the pump 200 described in relation to FIG. 2. In some embodiments, this pump 5534 can be a RENASYS GO pump, as sold by Smith & Nephew. The pump 5534 may be connected to the connector 5504 via a tube 5540. In use, the applicator 5520 is placed over an aperture 5535 formed in a drape 5531 that is placed over a suitably-prepared wound 5530, which may in some cases be filled with a wound packing material such as foam or gauze. Subsequently, with the pump 5534 connected via the tube 5540 to the connector 5504, the pump is activated, thereby supplying negative pressure to the wound. Application of negative pressure may be applied until a desired level of healing of the wound 5530 is achieved.

In some embodiments, the bridge portion 5502 may comprise an upper channel layer 5512 positioned between an upper layer 5510 and an intermediate layer 5514, with a lower channel layer 5516 positioned between the intermediate layer 5514 and a bottom layer 5518. Preferably, the layers 5510, 5514, and 5518 have elongate portions extending between proximal and distal ends and may be comprised of a material that is fluid-impermeable, for example polymers such as polyurethane. It will of course be appreciated that the layers 5510, 5514, and 5518 may each be constructed from different materials, including semi-permeable materials. In some embodiments, one or more of the layers 5510, 5514, and 5518 may be at least partially transparent. As illustrated in FIG. 5B, the upper and lower layers 5510 and 5518 may be curved, rounded or outwardly convex over a majority of their lengths. During assembly, for example, the layers 5510, 5514, and 5518 may be pinched together to weld or adhere the layers together. In doing so, the proximal ends of the channels 5512 and 5516 may be sandwiched between these layers, thus partially compressing the proximal ends of the channels 5512, 5516 and stretching the layers 5510, 5514, 5518 over these aforementioned proximal ends. Of course, the proximal ends of the materials used in the bridge portion 5502 may not necessarily be rounded or curved; as shown in FIG. 6, they can remain substantially squared off and straight.

The upper and lower channel layers 5512 and 5516 are preferably elongate layers extending from the proximal end 5503 to the distal end 5505 and may each preferably comprise a porous material, including for example open-celled foams such as polyethylene or polyurethane. In some embodiments, one or more of the upper and lower channel layers 5512 and 5516 may be comprised of a fabric, for example a knitted or woven spacer fabric (such as a knitted polyester 3D fabric, Baltex 7970®, or Gehring 879®) or a nonwoven material. Suitable materials may also include terry-woven or loop-pile materials. The fibers may not necessarily be woven, and can include felted and flocked (including materials such as Flotex®) fibrous materials. The materials selected are preferably suited to channeling wound exudate away from the wound and for transmitting negative pressure and/or vented air to the wound site, and may also confer a degree of kinking or occlusion resistance to the channel layers 5512 and 5516 as described below. In one embodiment, the upper channel layer 5512 may comprise an open-celled foam such as polyurethane, and the lower channel layer may comprise a fabric as described herein. In another embodiment, the upper channel layer is optional, and the system may instead be provided with an open upper channel. In the embodiment illustrated in FIG. 5B, the upper channel layer 5512 may have a curved, rounded or upwardly convex upper surface and a substantially flat lower surface, and the lower channel layer 5516 may have a curved, rounded or downwardly convex lower surface and a substantially flat upper surface.

In some embodiments, the fabric may have a three-dimensional (3D) structure, where one or more types of fibers form a structure where the fibers extend in all three dimensions. Such a fabric may in some cases aid in wicking, transporting fluid, and/or transmitting negative pressure. To prevent the channels 5512 and/or 5516 from being displaced or twisted while encased in the system 5501—which may impair performance of the respective channels under negative pressure—it may in some embodiments be preferable to adhere or otherwise secure the channels 5512 and/or 5516 to one or more of the layers 5510, 5514, and 5518. In certain embodiments, these materials remain open and capable of communicating negative pressure to a wound area under the typical pressures used in negative pressure therapy, for example between 40 to 150 mmHg, although higher and lower values are possible. In some embodiments, the fabric may comprise several layers of material stacked or layered over each other, which may in some cases be useful in preventing the channel 5516 from collapsing under the application of negative pressure. In other embodiments, the fabric used in channel 5516 may be between 1.5 mm and 6 mm; more preferably, the fabric may be between 3 mm and 6 mm thick, and may be comprised of either one or several individual layers of fabric. In other embodiments, the channel 5512 may be between 1.2-3 mm thick, and preferably thicker than 1.5 mm. Additionally, and as described previously, the materials used in the system 5501 are preferably conformable and soft, which may help to avoid pressure ulcers and other complications which may result from a wound treatment system being pressed against the skin of a patient. Further examples of 3D fabrics are discussed below in FIGS. 7A-C.

Preferably, the distal ends of the layers 5510, 5514, and 5518 and the channel layers 5512 and 5516 are enlarged at their distal ends (to be placed over a wound site), and may form a "teardrop" or other enlarged shape. The distal ends of at least the layers 5512, 5514, 5516, and 5518 may also be provided with at least one through aperture. This aperture may be useful not only for the drainage of wound exudate and for applying negative pressure to the wound, but also during manufacturing of the device, as these apertures may be used to align these respective layers appropriately.

Figure 5A:
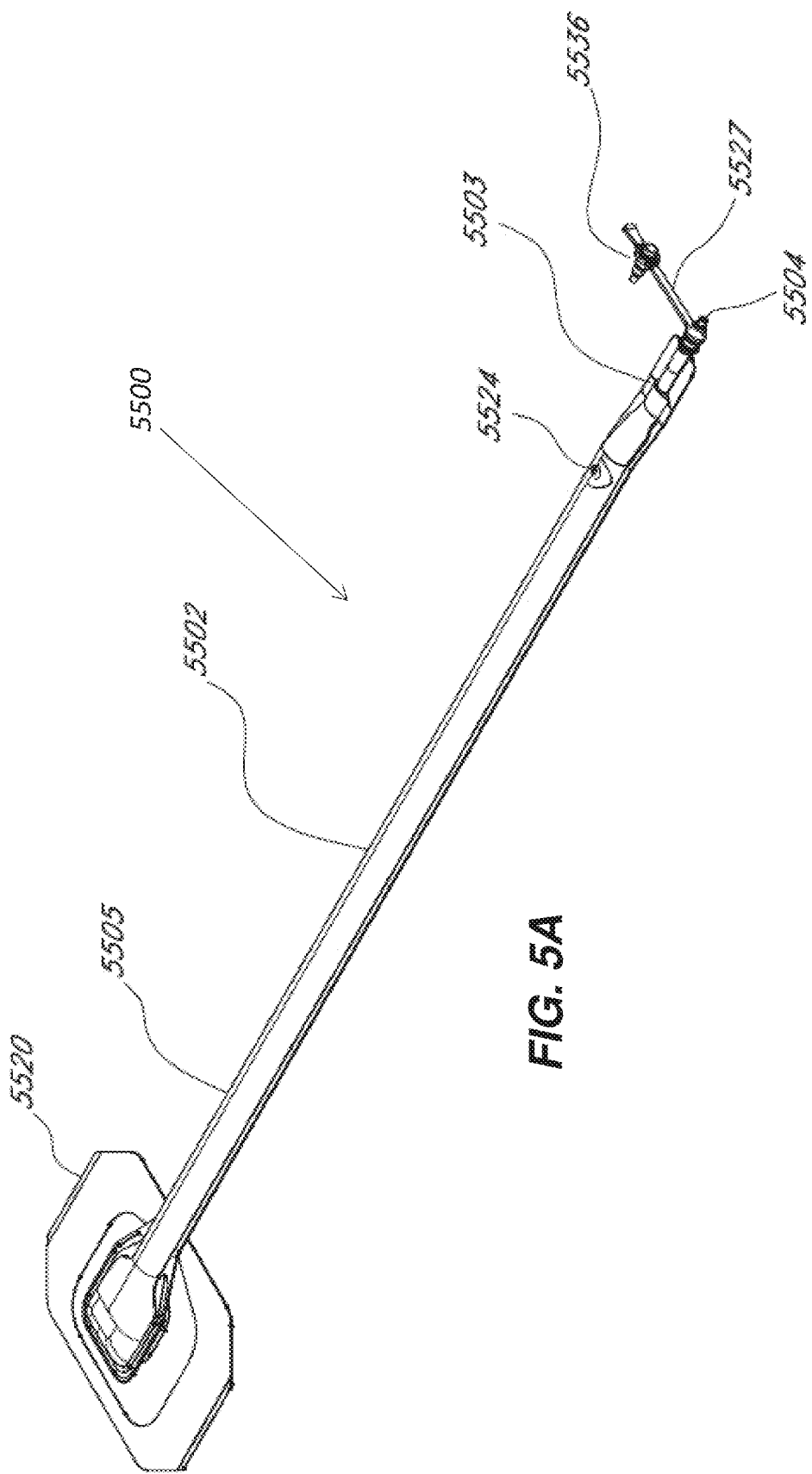
FIG. 5A illustrates an isometric view of a flexible suction adapter that may be used in a negative pressure wound treatment system.
Figure 5B:
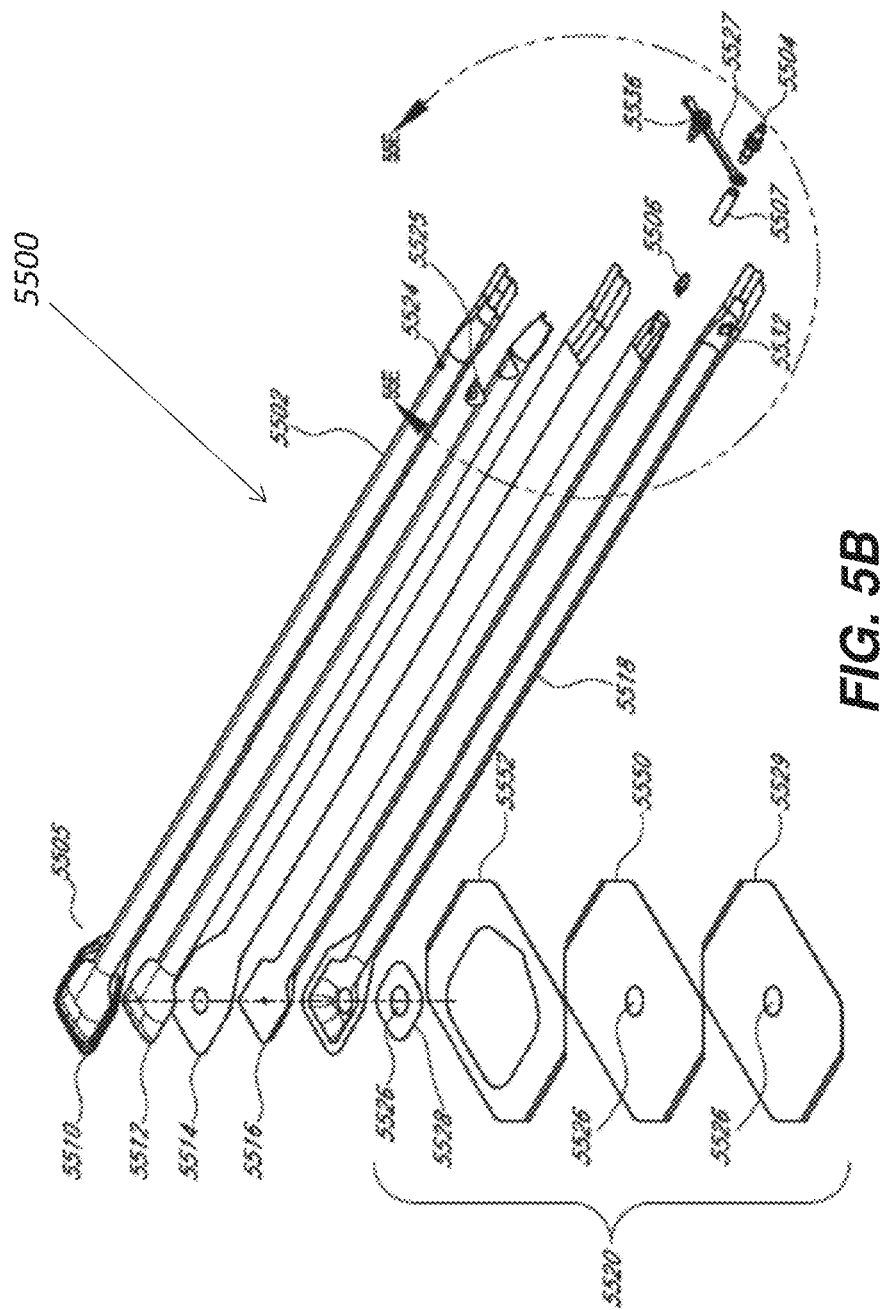
FIG. 5B illustrates an exploded view of the flexible suction adapter of FIG. 5A.
Figure 5C:
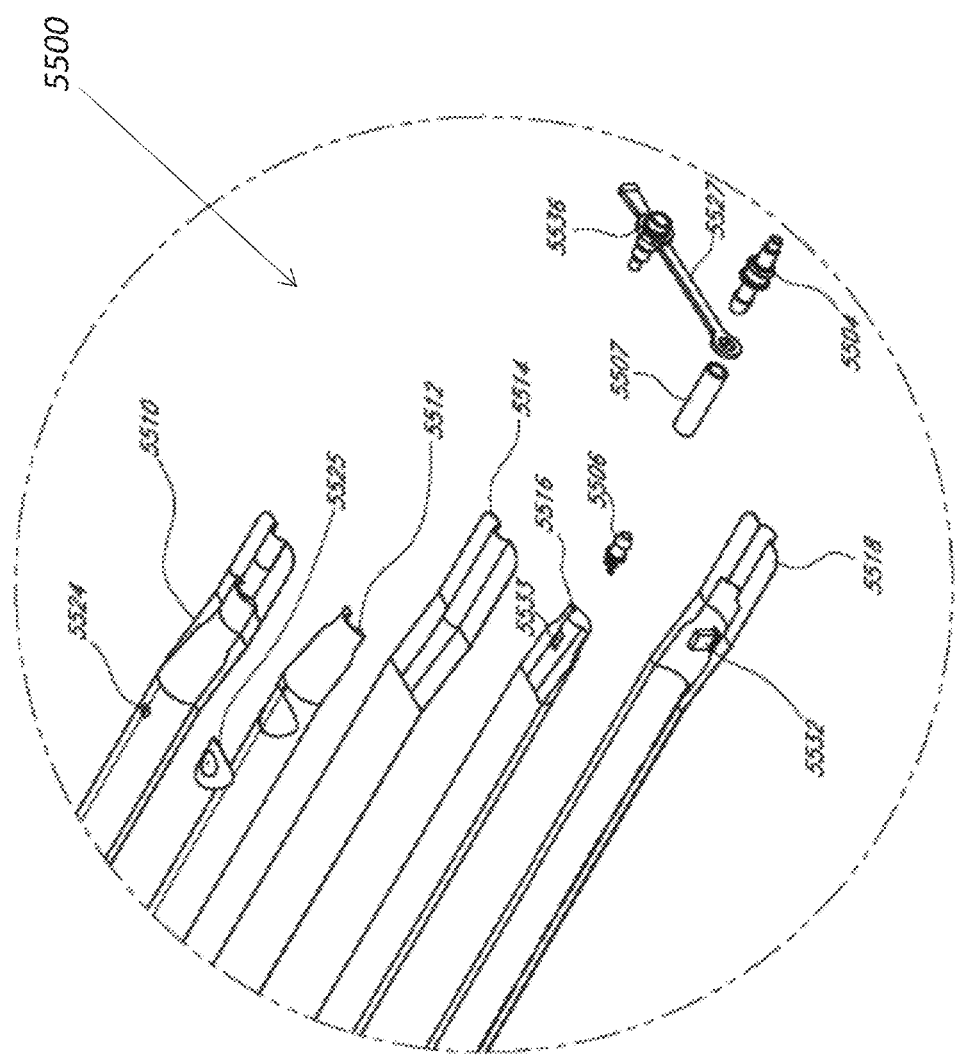
FIG. 5C illustrates a close-up view of the proximal end of the flexible suction adapter of FIG. 5B.
Figure 5E:
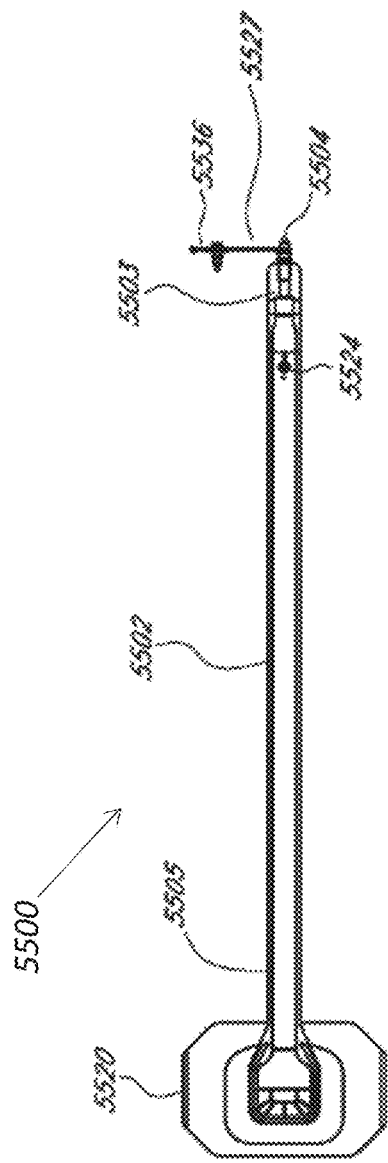
FIG. 5E illustrates a top view of the flexible suction adapter of FIG. 5A.
Figure 5F:
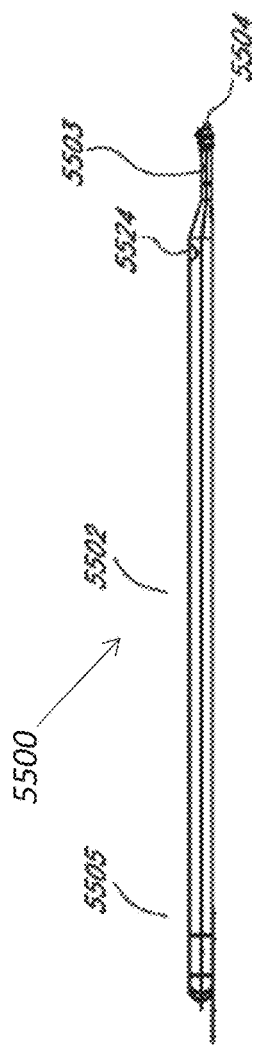
FIG. 5F illustrates a side view of the flexible suction adapter of FIG. 5A.
Figure 5G:
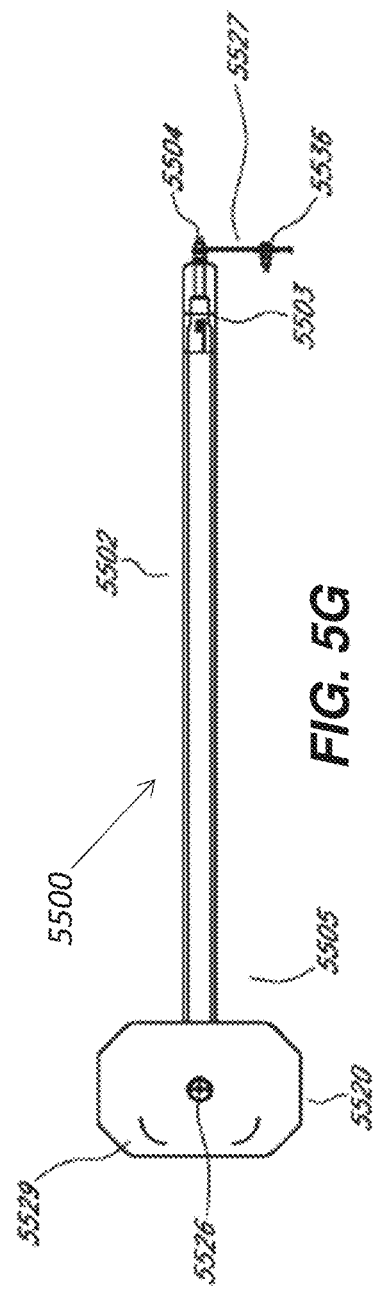
FIG. 5G illustrates a bottom view of the flexible suction adapter of FIG. 5A.
Figure 6:
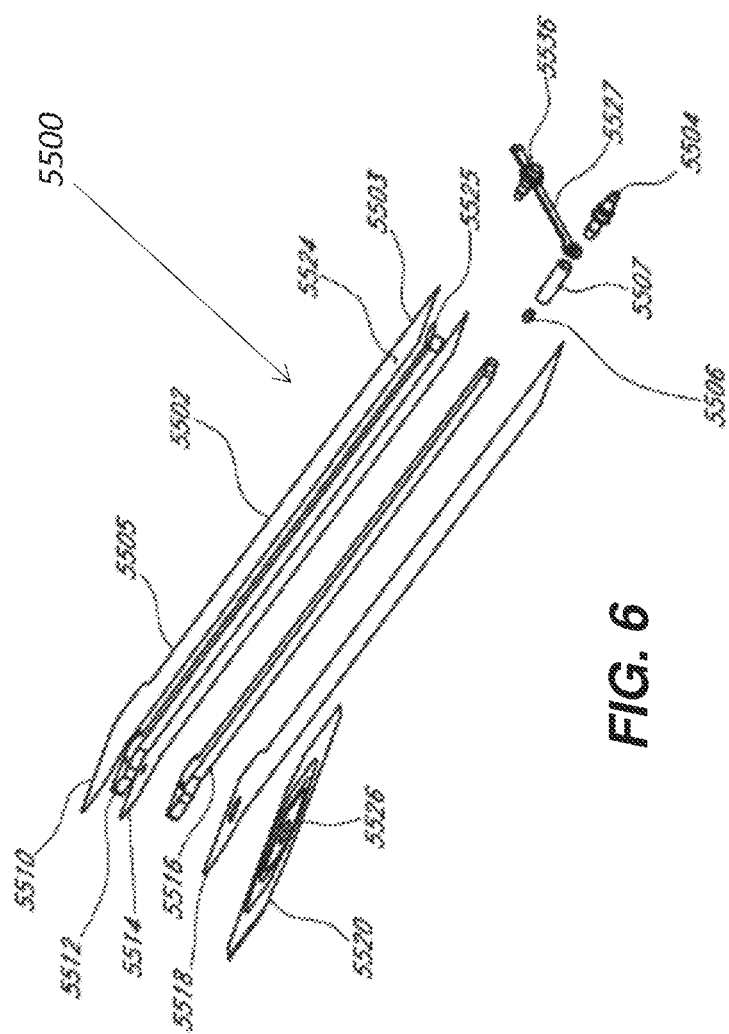
FIG. 6 illustrates an exploded view of an alternative flexible suction adapter.

With additional reference to FIGS. 5B-C and 6, a channel connector 5506 is provided at the proximal end 5503 of the bridge portion 5502, the channel connector 5506 preferably being configured so as to be embedded into the lower channel layer 5516 so as to create a secure fluidic connection. The channel connector 5506 may in some embodiments be inserted into a pre-made cavity formed into the channel 5516; as illustrated in FIG. 6, this cavity can be cut out or can be in the form of a rabbet joint. In some embodiments, the channel connector 5506 may be one of the connectors described in FIGS. 8A-B below. With one end of the channel connector 5506 being embedded into the lower channel layer 5516, the other end of the channel connector 5506 may be connected or in communication with, in one embodiment, a connector tube 5507, although in some embodiments the channel connector 5506 may be connected directly to the connector 5504, or else connected directly to a tube 5540 connected to a source of negative pressure. When using a connector tube 5507, the resulting assembly can permit a connector 5504 to be attached thereto. A cap 5536, which may be secured to the suction adapter for example via a cap leash 5527 secured with a ring disposed on the outer surface of the connector tube 5507. The cap 5536 may be used to cover the end of the suction adapter, for example at the connector 5504, so as to prevent exudate and other wound fluids from leaking out. The connector 5504 is preferably configured to connect with a tube 5540 connected to a source of negative pressure. The connector 5504 may for example comprise a lip or other such structure to aid in securing the connector 5504 to a tube 5540 and/or cap 5536, although it will be understood that other connector types are possible, including quick-disconnect couplings, luer locks, Christmas-tree, and other such connectors.

The upper layer 5510 may comprise additional material extending downward, preferably at least of the thickness of the bridge portion 5502; this material may then be used to bond or weld to the other layers so to form a fluid-tight seal. More specifically, during assembly, the upper layer 5510 may be attached, for example by melting, welding, or with adhesives, to the lower layer 5518 so as to form a fluid-tight seal (with the exception of the apertures at the distal and proximal ends). Preferably, the middle layer 5514 is attached to the top layer 5510 and the bottom layer 5518. In some embodiments, it may be preferable to attach or bond the connectors 5504 and/or 5506, as well as the tube 5507 to at least one of the layers 5510, 5514, 5518 so as to create a fluid-tight connection. To provide for a more secure connection, some embodiments may also be provided with a weld 5532 made onto the lower layer 5518. The lower channel 5516 may have a hole or aperture made through it, which may be used to weld it, via the weld 5532, to the lower layer 5518. This welding of the lower channel 5516 to the lower layer 5518 via the weld 5532 made through the hole 5533 may thus aid in preventing the various layers and channels from shifting or being displaced. Obviously, it will be understood that other securement means may be used, for example adhesives and the like, and that such arrangements may be also be used in the upper channel 5512.

In certain embodiments, for example as illustrated in FIGS. 5A-6, a controlled air leak 5524 may be disposed on the bridge portion 5502, for example at the proximal end thereof. This air leak 5524 may comprise an opening or channel extending through upper layer 5510, such that the air leak 5524 is in fluidic communication with the upper channel 5512. Upon the application of suction to the suction adapter 5500, air will enter through the air leak 5524 and move from the proximal end 5503 to the distal end 5505 along the upper channel 5512. The air will then be suctioned into the lower channel 5516 by passing through the apertures through the distal ends of the layers 5512, 5514, 5516 and 5518. The air leak 5524 preferably comprises a filter 5525. Preferably, the air leak 5524 is located at the proximal end of the bridge portion 5502 so as to minimize the likelihood of wound exudate or other fluids coming into contact and possibly occluding or interfering with the air leak 5524 or its filter 5525. In some embodiments, this filter 5525 is a microporous membrane capable of excluding microorganisms and bacteria, and which may be able to filter out particles larger than 45 µm. Preferably, the filter 5525 can exclude particles larger than 1.0 µm, and more preferably, particles larger than 0.2 µm. Advantageously, some embodiments may provide for a filter 5525 that is at least partially chemically-resistant, for example to water, common household liquids such as shampoos, and other surfactants. In some embodiments, reapplication of vacuum to the suction adapter 5500 and/or wiping of the exposed outer portion of the filter 5525 may be sufficient to clear any foreign substance occluding the filter 5525. The filter 5525 may be composed of a suitably-resistant polymer such as acrylic, polyethersulfone, or polytetrafluoroethylene, and may be oleophobic and/or hydrophobic. In some embodiments, the filter 5525 may also comprise a supporting backing layer, for example a nonwoven polyester support. Preferably, the air leak 5524 will supply a relatively constant air flow that does not appreciably increase as additional negative pressure is applied to the system 5501. In embodiments of the suction adapter 5500 where the air flow through the air leak 5524 increases as additional negative pressure is applied, preferably this increased air flow will be minimized and not increase in proportion to the negative pressure applied thereto.

The filter 5525 provided in the controlled air leak 5524 in certain embodiments may be useful in a system 5501 for use with more ambulatory and active patients. For example, a chemically-resistant filter may permit a patient to bathe or shower without damaging the filter's functionality when reconnected to a source of negative pressure. Any occlusion or fluid blocking the air leak 5524 could then be cleared by, for example, wiping off the filter 5525 or re-applying negative pressure to the suction adapter 5500. Such a system would also have the advantage that the system 5501 and any assorted wound dressing materials, if present, would not need to be removed and then re-applied should a patient need to be disconnected from the source of negative pressure, for example incidental to bathing. This would entail significant advantages in improving the cost-effectiveness and ease of use of the present treatment system.

The suction adapter 5500 is preferably constructed so as to provide a consistent fluid flow even if the suction adapter 5500 is kinked or weighted down. For example, in use on a patient, the bridge portion 5502 may become folded over itself, or else the patient may roll over, thus placing his or her weight over at least a portion of the suction adapter 5500. Typically, prior art dressings and fluidic connectors become blocked or ineffective in such situations and in some cases may contribute to complications such as pressure ulcers. Here, however, certain embodiments provide for improved blockage resistance if kinked or weighed down. Preferably, by employing channel layers 5512 and 5516 as described above, and more preferably by employing a foam channel layer 5512 and a fabric channel layer 5516, the suction adapter 5500 is able to maintain a flow rate through the air leak 5524 of at least 0.08 L/min, and preferably 0.12 L/min while negative pressure is applied through a source of negative pressure. Further embodiments also provide for the suction adapter 5500 to be able to handle fluid exudate drainage from the wound site through the lower channel 5516 of at least 10 L/day, or 6.9 ml/min. Certain embodiments provide for the suction adapter 5500 to maintain these flow rates with a weight, for example a 12 kg weight, pressing down on the bridge portion through a rod with a 1 in. diameter. In some embodiments, these flow rates are also maintained while the bridge portion 5502 is kinked over itself with the same weight, or for example with a 4.75 kg weight placed directly on the folded region. It is preferable that the suction adapter 5500 be able to withstand being folded or kinked over even during an extended period of time, for example over 40 hours, and not show any degradation in performance (e.g., flow rates) compared to its performance prior to being folded or kinked over. Preferably, embodiments of the suction adapter 5500 are also able to transmit and maintain a negative pressure at the wound that is close to the negative pressure level at the source of negative pressure. For example, an acceptable level of pressure maintained at the wound may be within +−0.25 mmHg of the negative pressure set at the source of negative pressure, with this pressure being preferably maintained at this level within 95% of the time that the suction adapter 5500 has negative pressure applied to it. Acceptable pressure levels may include pressure ranges between 40-120 mmHg, although levels of 200 mmHg have successfully been used.

With additional reference to FIGS. 4A-5B and 6, the suction adapter 5500 also comprises an applicator 5520 designed for placement over a wound site. Preferably, the applicator 5520 comprises a flexible layer 5550, for example polyethylene or polyurethane, with a layer of adhesive on its lower (wound-facing) side. Optionally, a protective release layer 5529 may be placed on the adhesive layer, which is removable before use. In some embodiments, a more rigid removable backing layer 5552 may be provided on the upper side of the applicator 5520 to facilitate handling of the applicator 5520 due to the flexibility of the layer 5550. The applicator 5520 preferably comprises an attachment point for the bridge 5502 at the distal end 5505, for example using a section of double-sided adhesive tape 5528. The double-sided adhesive tape 5528 may be protected by an additional protective release layer, which is removed prior to adhering the bridge 5502 to the applicator 5520. It will be understood that different attachment methods are also contemplated, for example heat sealing, welding, or suitable adhesives. Some embodiments may also permit the manufacture of the bridge 5502 and the applicator 5520 as a single unit that does not require separate attachment means. The applicator 5520 preferably comprises at least one aperture 5526 through itself and designed to be placed over a wound site, and which can serve to fluidically connect the wound site to the source of negative pressure and to the air leak while also serving as a conduit to draw out wound exudate from the wound site.

Figure 4A:
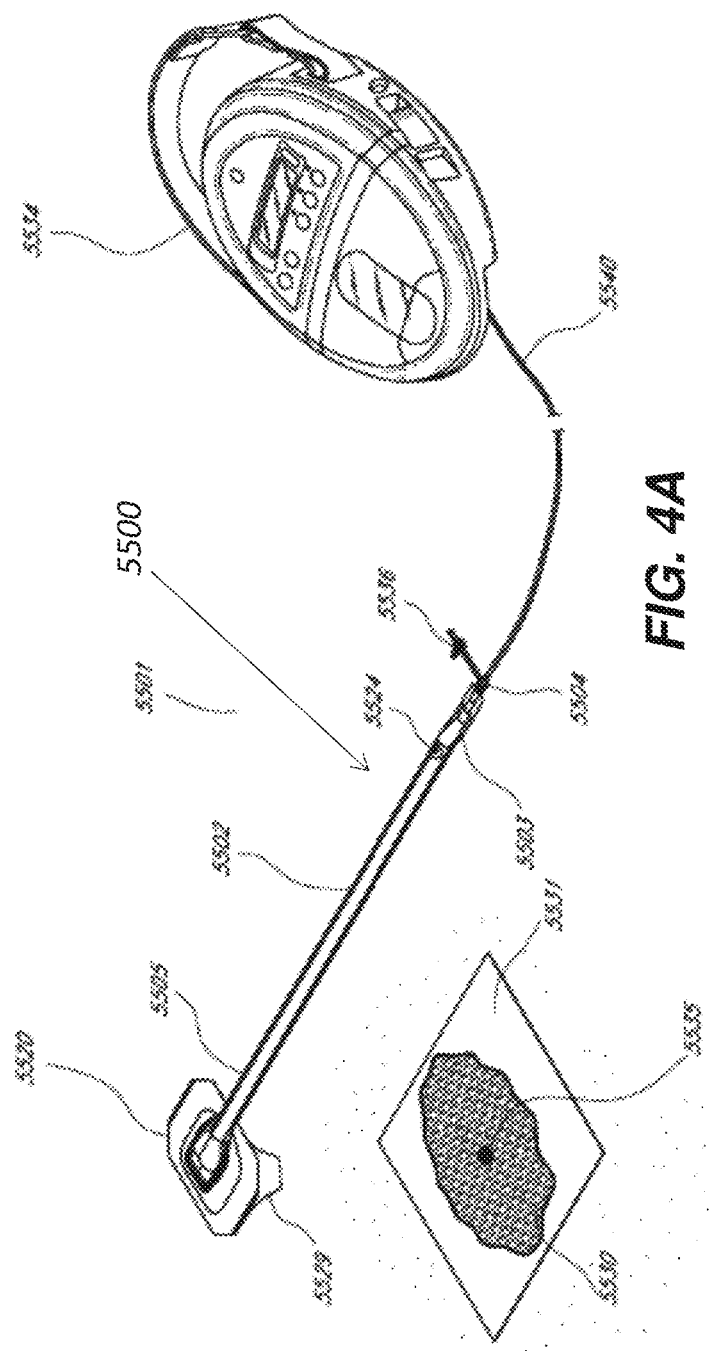
FIG. 4A illustrates an embodiment of a negative pressure wound treatment system comprising a pump, and illustrating a flexible suction adapter being applied to a wound.

In use, and with reference to FIGS. 4A-B, the system 5501 may be used in a similar fashion to the other embodiments previously disclosed herein, such as the system 100 described in relation to FIG. 1. A wound site 5530 is preferably cleaned and prepared in a suitable fashion, and a wound packing material, if necessary, placed into the wound site, followed by a drape 5531. An aperture 5535 through the drape to the wound site is then created, although some embodiments may have a pre-made aperture 5535. Subsequently, an operator may situate the applicator portion 5520 over the aperture 5535. After removing the backing layer 5529 (if present) from the adhesive layer on the underside of the applicator portion 5520, the applicator is sealed to the drape 5531, and the backing layer 5552 (if present) is also removed from the applicator portion 5520. A fluidic conduit such as a tube 5540 may then be connected to the connector 5504. The tube 5540 may also be connected to connector 5504 prior to applying the applicator to the wound site. The fluidic conduit is connected to a source of negative pressure 5534, preferably with a container suitable for containing wound exudate interposed therebetween. The application of negative pressure may then be effectuated to the wound site 5530 until the wound site progresses to a desired level of healing.

During use of the system 5501, wound exudate from the wound site 5530 is drawn by the negative pressure through the lower channel layer 5516. The air leak 5524 allows air to pass through the upper channel layer 5512 into the apertures through the distal ends of the layers 5512, 5514, 5516 and 5518. The negative pressure draws air passing through the upper channel layer into the lower channel layer 5516 back toward the source of negative pressure or pump. In some embodiments, the controlled air leak 5524 provides a constant flow of air through the suction adapter 5500, which then may be used to determine whether blockage or leakage is present. Causes of blockage can include, for example, situations where the lower channel 5516 becomes occluded with wound debris. Leakage causes can include, for example, improper sealing of the drape over the wound site, or physical damage to the suction adapter 5500 leading to excess air leaking into the system. The blockage or leakage may be determined, in certain embodiments, by measuring the speed of the pump while the pump works to maintain a constant negative pressure. Pump speed may also be measured indirectly by measuring the amount of voltage or signal sent to the pump.

Figure 7A:
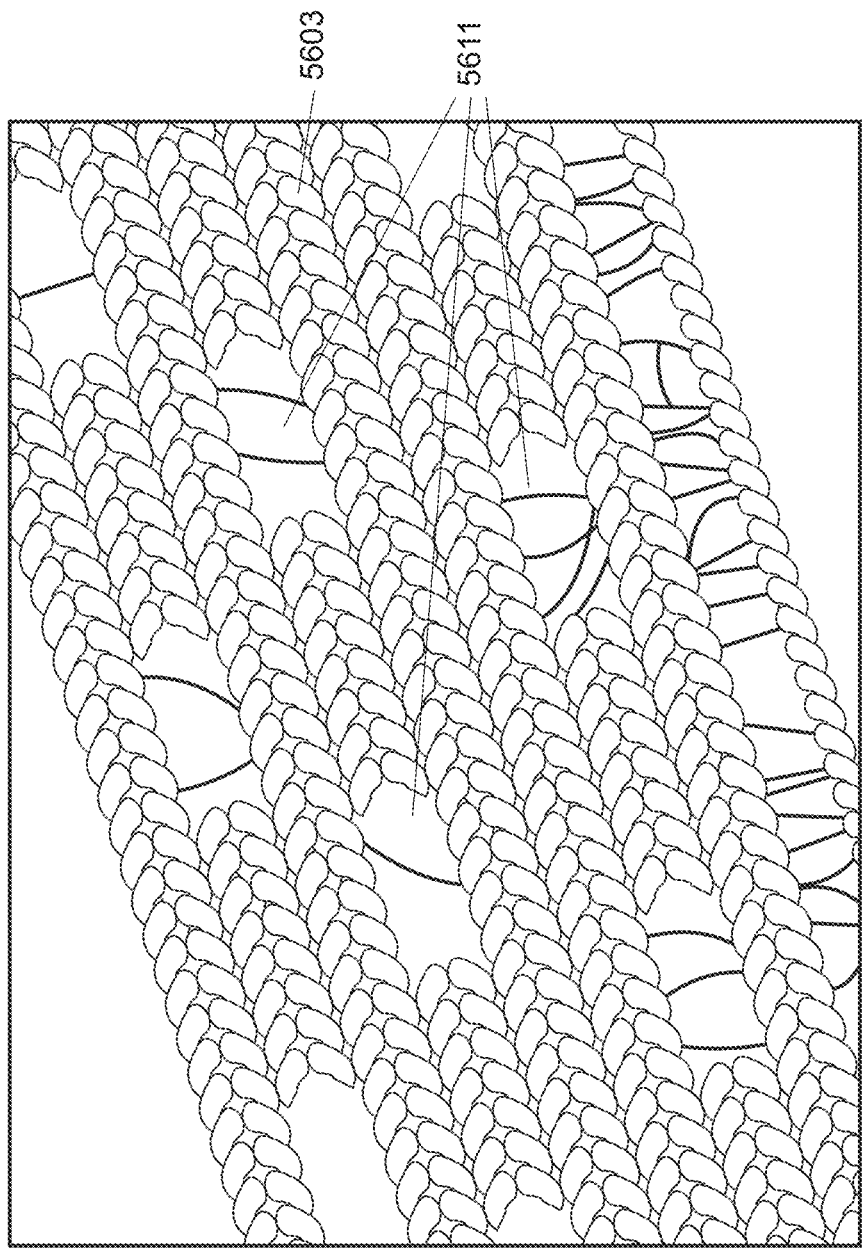
FIG. 7A illustrates a top view of a 3D fabric that may be used in a negative pressure wound treatment device.
Figure 7B:
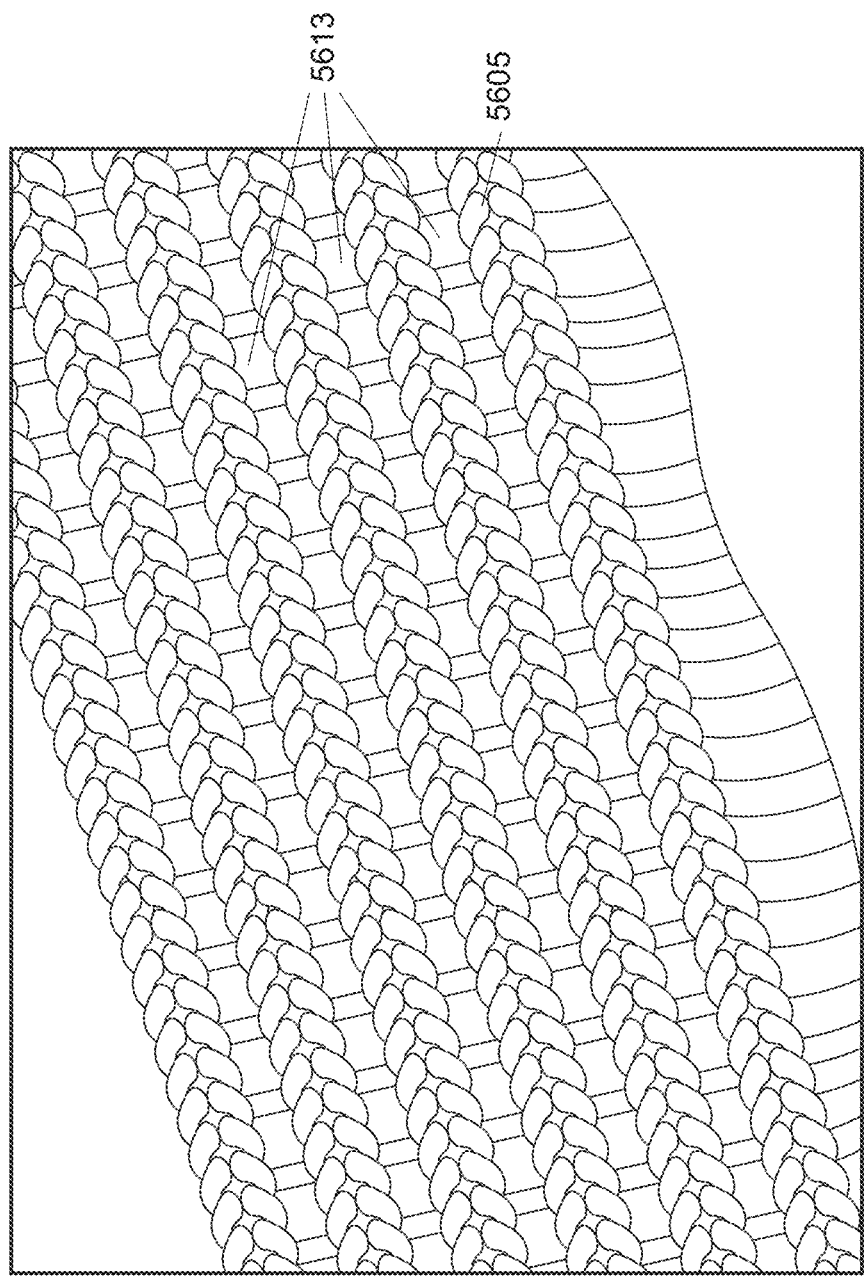
FIG. 7B illustrates a bottom view of the 3D fabric of FIG. 7A.
Figure 7C:
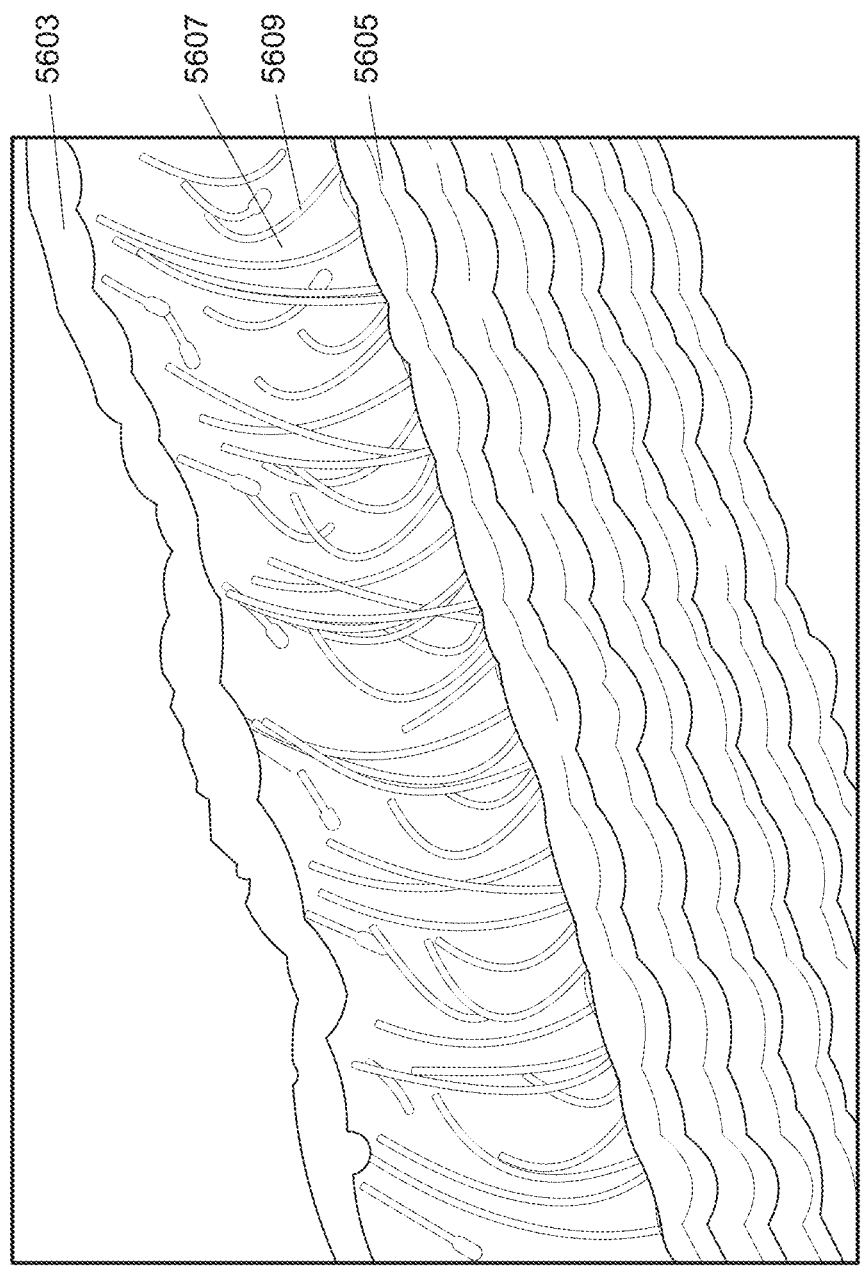
FIG. 7C illustrates a side cutaway view of the 3D fabric of FIG. 7A.

FIGS. 7A-C illustrate views of a 3D fabric that may be used in various embodiments described herein, for example the bridge portion 5502 of the suction adapter illustrated in FIGS. 4A-6. Although other porous materials such as foam may be used in the embodiments described herein, for example in the upper and lower channels 5512 and/or 5516 illustrated in FIGS. 5B-C, the use of 3D fabrics may be advantageous in some circumstances. Certain 3D fabrics have been found to perform well in conveying negative pressure to and wound exudate from a fluidic suction adapter, even while under compression—for example when a patient's weight is placed directly upon the suction adapter, or when negative pressure is applied and/or when the fluidic suction adapter is kinked or folded. Some 3D fabrics that have been found to perform acceptably include knitted polyester 3D fabric, Baltex 7970®, Gehring 879®, or Coolmax®. Of course, other fibers and fabric types may be used in part or in whole to make 3D fabrics, and include without limitation polyamides such as nylon, viscose, cotton, as well as other synthetic microfibers. 3D fabrics may also be constructed at least in part from fibers such as Nomex® and Kevlar®. Other types of fabrics and materials disclosed elsewhere herein may also be used.

In one embodiment, as illustrated in FIGS. 7A-C, the 3D fabric may comprise a bottom side 5603, a top side 5605, and an open middle area 5607. FIG. 7A illustrates the bottom (wound-facing) side 5603 of a 3D fabric, which may be woven so as to create oblong or ovoid openings 5611 extending lengthwise across the fabric. In one embodiment, the oblong or ovoid openings 5611 represent or provide an open area of between 10 and 45% (or about 10% to about 45%) of the surface area of the bottom layer, more preferably 10% to 30% (or about 10% to about 30%). Here, fibers are knitted (for example by warp knitting) so as to also include these larger openings or pores that permit bulk transport of wound fluids in addition to wound fluids carried along the fibers by capillary action of the fibers. Apertures that are optionally formed in the distal end of the 3D fabric (as illustrated in FIGS. 5B and 6) may also aid in the bulk evacuation of wound debris and fluids.

FIG. 7B illustrates the top side 5605 of a 3D fabric that may be used as described herein. This top side 5605 in one embodiment does not have the larger ovoid apertures 5611 of the bottom side 5603, but may have openings 5613 defined by fibers extending lengthwise and generally transversely or at an angle across the width of the fabric. As illustrated, these openings are generally rhombus-shaped. In one embodiment, these openings 5613 may represent or provide an open area greater than that of the bottom layer, for example between 30% and 50% (or about 30% and about 50%). Of course, it will be understood that the fabric presented here is a non-limiting example, and different fabric configurations and orientations are possible, for example with the top side 5605 being placed downward so as to face the wound and with the bottom side 5603 facing upward.

FIG. 7C illustrates a cross-section of a 3D fabric (the bulb-like projections on the vertical fibers in the fabric are an artifact of the cutting process). The vertically extending fibers 5609 may be woven so as to extend through the middle open area 5607 while also being connected to the bottom and top layers 5603 and 5605. Preferably, the fibers 5609 present in the open middle layer 5607 will have sufficient stiffness so as to help prevent compression of the fabric. As illustrated in this figure, and without wishing to be bound by theory, 3D fabrics that have been found to perform well will often include a larger open area 5607 in the middle portion that may permit exudates and other fluids to be effectively transported away from a wound site while under the application of negative pressure, while more denselywoven outer layers 5603, 5605 may aid in providing additional tensile strength and capillary wicking action. For example, the middle layer may include an open volume of greater than 50% (or greater than about 50%). Obviously, the resulting fabric cannot be too thick or composed of fibers that are too stiff, as the resulting suction adapter and system may not remain sufficiently flexible for comfortable usage with a patient.

It will often be advantageous to tailor the performance characteristics of the 3D fabric while in use to account for various requirements of the suction adapter. In particular, the flow rate of exudate through the fabric, for example when under compression, may be simplified by considering the porosity of the fabric. In such situations, and again without wishing to be bound by theory, the porosity of the fabric, and thus the space that will be available for fluids to travel through, may be determined in part by the knit pattern of the fibers used in creating the 3D fabric, the thickness of the fibers used therein, and their respective stiffness and hardness (especially when under compression). Fibers may also be modified by surface properties (the fibers can be flat or textured) and the number of fibers or filaments used in the resulting fabric. Compression resistance may be affected by the choice of fiber or monofilament used in the vertical axis of the fabric, and generally, a stiffer material will improve compression resistance on this axis. Other materials properties, such as hydrophobicity, may play a role. In some cases, it may be beneficial to treat the fabric to be hydrophilic, for example with a hydrophilic polymer, so as to improve wicking of fluids. Preferred embodiments of the 3D fabric used with certain suction adapters have been found to work well when Baltex® fabric is treated in such a fashion. Other possible treatments may include lipophilic coatings to prevent proteins from adhering and building up during use, which may cause clogging and loss of pressure to the wound site.

The flow rate through the 3D fabric while under the application of negative pressure may be approximated by considering each opening as a separate orifice plate subject to Bernoulli's principle while under laminar flow. To simplify calculations, the area of openings for a given area of 3D fabric may be used. Thus, the 3D fabric may be optimized to achieve a good balance between factors such as the compression resistance required and the resulting flow rate under the application of negative pressure. Further optimization will also take place with the stiffness and flow rate of the 3D fabric being tailored to application in the embodiments described herein. Optimization of the properties and dimensions of the 3D fabric will also preferably take into account a balancing between the flow rate and stiffness required and the conformability of the fabric, as a fabric that is too stiff may not bend appropriately and may also be uncomfortable on the patient. The 3D fabric should preferably be designed so as to yield when compressed against tissue, thereby preventing tissue compression (for example against bony prominences in the patient) and the discomfort and damage, such as pressure ulcers, that may follow. For example, the dimensions of the fabric may be tailored for the ultimate use of the suction adapter—smaller in the case of distal extremities such as fingers, and larger for abdominal and burn wounds. A fabric that is too stiff may also cause pressure ulcers and other such complications, although it may function acceptably in larger dimensions.

In practice, and as also described previously herein, flow rates through embodiments of the suction adapter using 3D fabrics are at least 0.08 L/min, preferably up to 10 L/min during the application of negative pressure, and should be able to handle fluid exudate drainage of at least 10 L/day. Some embodiments of the suction adapter may be configured to handle much larger wounds, including abdominal wounds, and which in some cases may exude at least 0.5 L/hr, or 12 L/day. In more extreme cases, the pump used (for example, the RENASYS EZ) may be able to evacuate up to 16 L/min, thereby evacuating a large wound to a negative pressure level of 120 mmHg in less than a minute. The pressure drop calculated due to the 3D fabric should be minimal, and the level of negative pressure measured at a wound site is preferably within 25 mmHg of the pressure level measured at the source of negative pressure. Although the pressure drop increases as the negative pressure applied increases (thus rendering the 25 mmHg target more difficult to reach), embodiments of the wound treatment system are preferably able to maintain this target pressure to at least a negative pressure of 200 mmHg. The suction adapter and system are preferably able to function within pressure ranges required for negative pressure, which are estimated to be from around 40 mmHg to 200 mmHg. Pressure ranges greater than 200 mmHg are possible, but these may in some circumstances cause patient discomfort. The apparatus may also function at lower pressure ranges, such as 20 mmHg, although at such low pressure levels the therapeutic effects resulting from negative pressure may be diminished, with the device acting more as a drainage device. Preferably, embodiments of a negative pressure treatment system are able to maintain these target pressures at the wound site within 95% of the time that negative pressure is being applied to the wound. In some embodiments, the fabric may comprise several layers of material stacked or layered over each other, which may in some cases be useful in preventing the channel 5516 from collapsing under the application of negative pressure. In other embodiments, the fabric used in channel 5516 may be between 1.5 mm and 6 mm; more preferably, the fabric may be between 3 mm and 6 mm thick, and may be comprised of either one or several individual layers of fabric. In other embodiments, the channel 5512 may be between 1.2-3 mm thick, and preferably thicker than 1.5 mm. Preferably, the 3D fabric is able to withstand a load of at least 5.3 psi with a compression of not more than 10% of the fabric's original thickness. Further, the 3D fabric may also be able to resist compression to less than half of its original thickness when subjected to a load of 15 psi.

In a preferred embodiment, a 3D fabric may be woven from 100% polyester using yarns of 150 and 225 Denier, to yield a fabric weighing approximately 23 to 25 oz per square yard. In these cases, the fabric may be approximately 5.8-6.8 mm thick. The bottom portion of the fabric may also have several openings or pores 5611 similar to those illustrated in FIG. 7A, which may be elongated, rectangular or ovoid in shape and oriented with their long axis lengthwise along the fabric. The openings 5611 may be arranged in a plurality of rows extending lengthwise across the fabric, for example 2 to 5 rows, or more preferably 3 rows as illustrated in FIG. 7A. The openings 5611 may be spaced equidistantly from each other in each of the rows, and may form a staggered pattern from one row to another. In one embodiment, each row may have approximately 6-10 openings, more preferably 8 openings, per 2 inches (or about 50 mm). Along a given width or transverse dimension of the fabric, the transverse rows formed by the openings may have a spacing of approximately 6-10 openings, more preferably 8 openings, per 2⅛ inches (or about 54 mm). In one embodiment, the openings may have a length of between about ¹⁄₁₆" to about 1" lengthwise, and a width of between about ¹⁄₃₂" and ½ "widthwise. In one example, the openings measure approximately ⅛" (or about 3.2 mm) lengthwise and ¹⁄₃₂" (or about 0.79 mm) across. The 3D fabric in one embodiment may have an overall length of between about 50 and 100 mm, more preferably about 60 mm, a width between about 5 and 15 mm, more preferably about 9 mm, and a thickness of about 6 mm.

Embodiments of the systems described herein have been tested and found to perform satisfactorily. Such testing was performed by constructing suction adapters from embodiments described herein. The distal ends of the suction adapters were then placed over an aperture made onto a drape placed over a simulated wound cavity provided with a source of simulated wound fluid, which was controllable and which can vary the flow rate of the wound fluid. The simulated wound cavity was also in some cases packed with foam or some other wound packing material. In some tests, the simulated wound fluid was a 5:1 water to glycerol mix, and in others filtered horse serum (available from Oxoid, United Kingdom) was used. The proximal end of the suction adapter was then connected to a source of negative pressure, in this case a pump. Flow rate tests and other measurements were then conducted at various negative pressure ranges and simulated exudate flow rates and air leak rates.

FIG. 8A illustrates an embodiment of a connector 5704, similar to the connector 5506 described previously, and which may be used to securely connect a source of negative pressure to a channel 5716 of a suction adapter such as the ones described herein. For example, this channel 5716 may be the upper channel 5512 or, more preferably the lower channel 5516 in FIGS. 55-56. Generally, such connectors 5704 may be useful in providing a more secure connection from the source of negative pressure to a negative pressure treatment system. The use of these connectors 5704 is optional, and may not be necessary in all embodiments described herein. In use, a tube 5740 connected to the connector 5704 may pull, or other external forces may somehow disengage the connector 5704 away from the channel 5716 to which it is attached. In such situations, application of negative pressure to the wound may be reduced or stopped. Further means to secure the connector 5704 to the remainder of the system may, as described above, include bonding or attaching other layers of the treatment system, if present, to the connector 5704. The connectors 5704 may be designed so as to create a secure connection with a fabric or material used in a channel; when 3D fabrics or 3D knitted materials are used, some embodiments of the connector 5704 are configured to engage with or attach to a portion of the material or fibers of the material to create a more secure connection. Preferably, embodiments of the connector 5704 are able to withstand a pulling force of up to 20 kg before disconnection and/or failure of the connector occurs, preferably such that the connector disengages from the channel it is connected to. It will be understood that other embodiments may be configured to withstand a lower pulling force, and may be tailored to release so to prevent injury to a patient (for example, constriction of the suction adapter and/or drainage tubes around a limb).

FIG. 8B illustrates an embodiment of the connector 5704*a* comprising two or more projections 5752 extending distally lengthwise from the preferably cylindrical main body of the connector 5704*a*. The main body also comprises a central channel 5755 extending lengthwise through the main body of the connector 5704*a*. The projections 5752 may additionally comprise one or more barbs 5754 attached thereto. Preferably, these barbs 5754 are angled proximally so as to act as anchors when pushed or inserted into the channel 5716. When the channel 5716 is a 3D fabric or knitted material, the barbs 5754 are configured to engage to the fibers therein, creating a more secure connection. At the proximal end of the connector 5704*a*, a lip 5756, which may be provided in a frustoconical form, may also be provided for connection to a tube 5740. The tube 5740 may be connected to the connector 5704*a* (as well as the other connectors described herein) for example by press-fitting, although other connections means are possible. The tube 5740 may be the same as tube 5507 in FIG. 6, or it may be any other tube used to provide fluid communication with a source of negative pressure. It will also be appreciated that the features of these connectors, particularly at the distal ends, can be incorporated onto the ends of tubes used to communicate negative pressure, such that those tubes can be directly connected to the suction adapter system. Examples of such applications where additional disclosure relating to the preceding descriptions about the connectors may be found include U.S. Pat. No. 9,050,398, titled "APPARATUSES AND METHODS FOR NEGATIVE PRESSURE WOUND THERAPY" issued Jun. 9, 2015, which is hereby incorporated by reference in its entirety.

Flexible Suction Adapter with Separate Air Leak

Figure 9A:
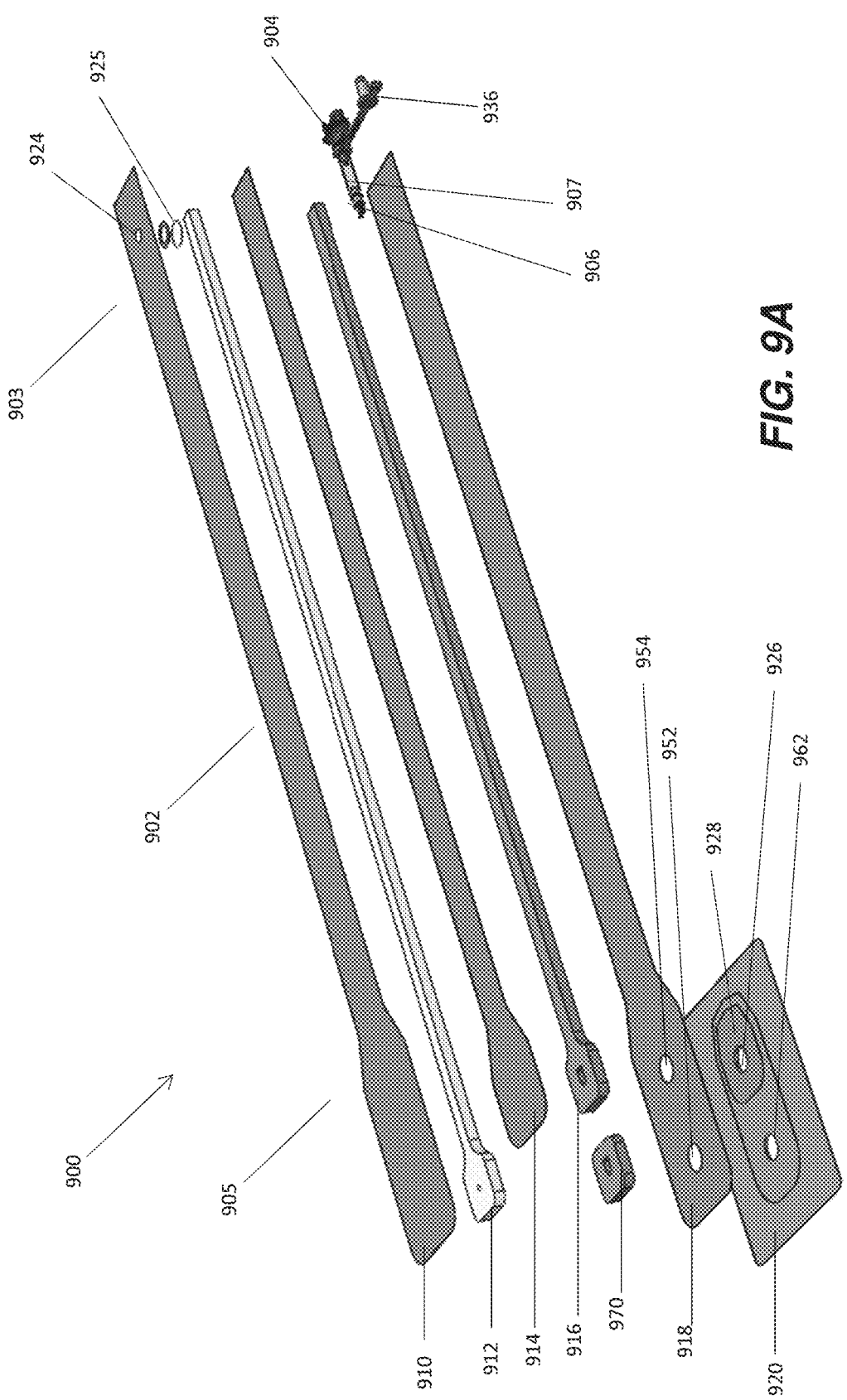
FIG. 9A illustrates an exploded view of the flexible suction adapter that may be used in a negative pressure wound treatment system.
Figure 9B:
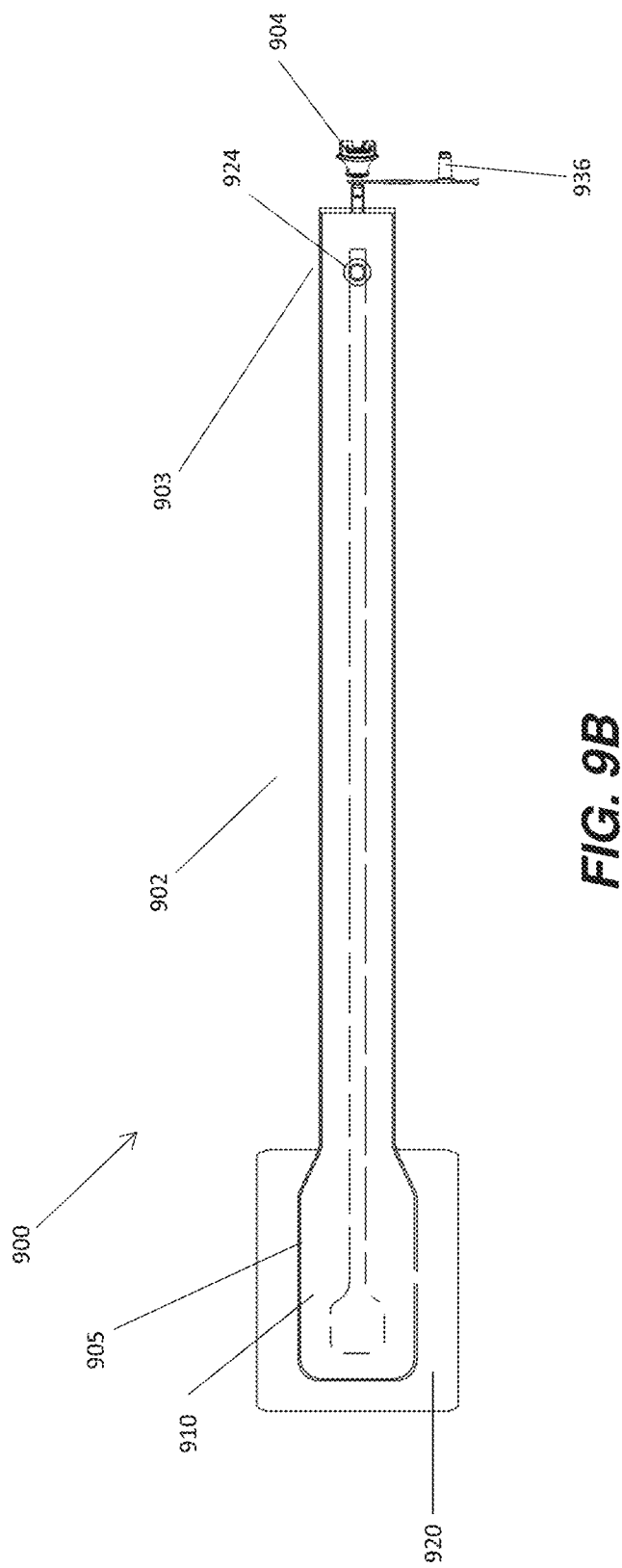
FIG. 9B illustrates a top view of the flexible suction adapter of FIG. 9A.
Figure 9C:
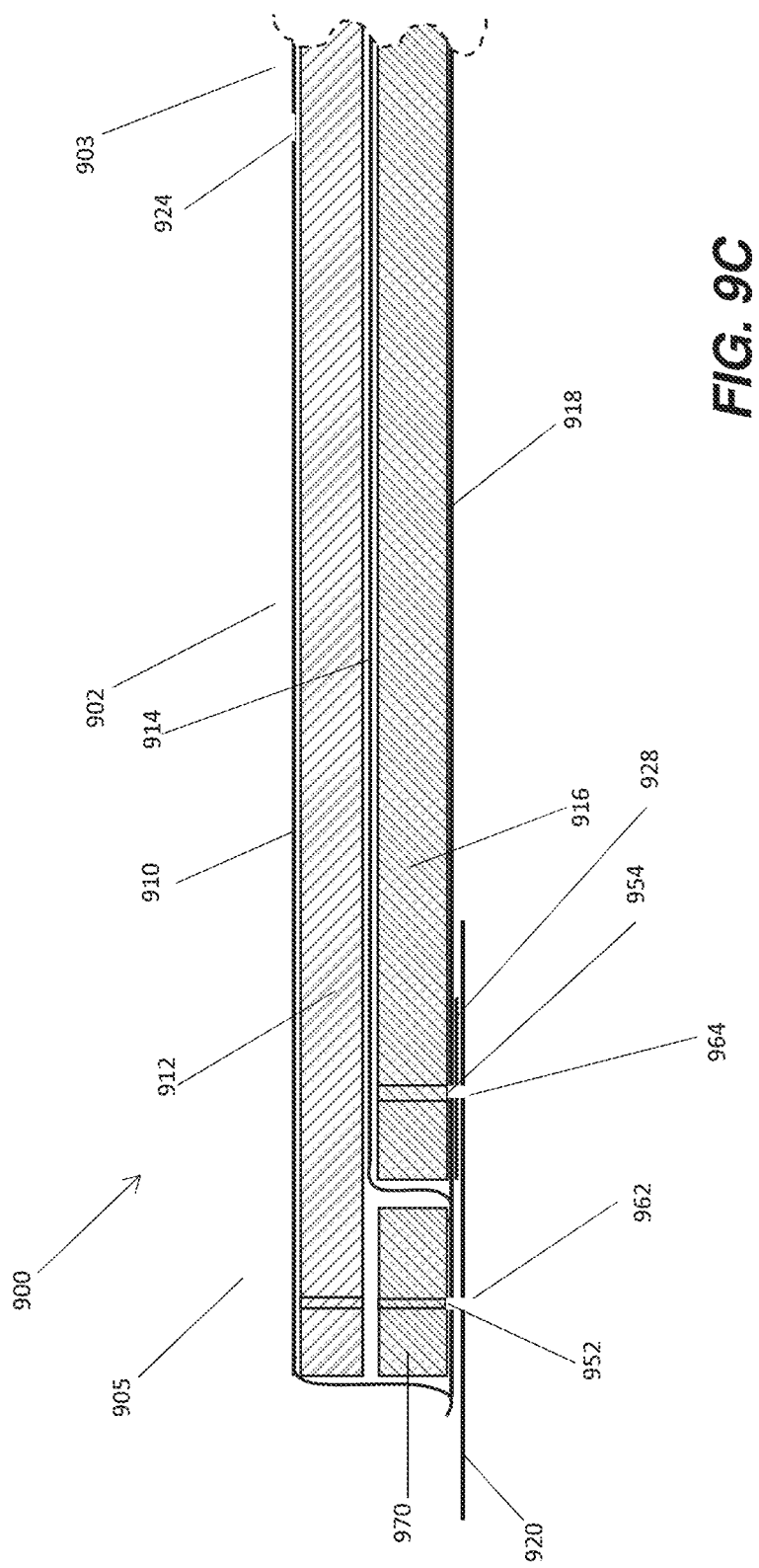
FIG. 9C illustrates a cross-sectional view of the flexible suction adapter of FIG. 9A.

FIGS. 9A-C illustrate an embodiment of a flexible suction adapter 900 similar to the embodiments of the flexible suction adapter 5500 illustrated in and described in relation to FIGS. 4A-8B. FIG. 9A illustrates an exploded view of the suction adapter 900, and FIG. 9B illustrates a top view of the suction adapter 900. Additionally, FIG. 9C illustrates a cross-sectional view of the suction adapter 900. The suction adapter 900 may include a bridge portion 902 having a proximal end 903 and a distal end 905 and an applicator 920 at the distal end 905 of the bridge portion 902, forming the flexible suction adapter 900. Preferably, the flexible suction adapter is constructed in a similar fashion to the flexible suction adapter 5500, and the bridge portion 902 may be constructed from a similar dual layer arrangement as previously described. For example, in some embodiments, the bridge portion 902 may include an upper channel layer 912 positioned between an upper layer 910 and an intermediate layer 914, with a lower channel layer 916 positioned between the intermediate layer 914 and a bottom layer 918.

In certain embodiments, for example as illustrated in FIGS. 9A-C, a controlled air leak 924 may be disposed on the bridge portion 902, for example adjacent the proximal end thereof. This air leak 924 may comprise an opening or channel extending through upper layer 910, such that the air leak 924 is in fluidic communication with the upper channel 912. The air leak 924 may include a filter 925.

The applicator 920 preferably comprises an attachment point for the bridge portion 902 at the distal end 905, for example using a section of double-sided adhesive tape 928. It will be understood that different attachment methods are also contemplated, for example heat sealing, welding, or suitable adhesives.

A connector 904 may be disposed at the proximal end 903 of the bridge portion 902, so as to connect to at least one of the channels 912 and/or 916. A cap 936 may be provided with the suction adapter 900 (and can in some cases, as illustrated, be attached to the connector 904). As illustrated in FIG. 9A, a channel connector 906 may be provided at the proximal end 903 of the bridge portion 902, the channel connector 906 preferably being configured so as to be embedded into the lower channel layer 916 so as to create a secure fluidic connection. With one end of the channel connector 906 being embedded into the lower channel layer 916, the other end of the channel connector 906 may be connected or in communication with, in one embodiment, a connector tube 907, although in some embodiments the channel connector 906 may be connected directly to the connector 904, or directly to a tube connected to a source of negative pressure.

Each of the components of the suction adapter 900 may be similar with each corresponding components of the suction adapter 5500, therefore description of each corresponding components of the suction adapter 5500 previously herein also applies to each components of the suction adapter 900, except as noted below.

In a similar fashion to the suction adapter 5500, an upper fluid passage may be defined by and between the upper layer 910 and the intermediate layer 914. In some embodiments, such as shown in FIG. 9C, the upper layer 910 and the lower layer 918 extends further at the distal end 905 than the intermediate layer 914, such that the upper fluid passage may be also partially defined between the upper layer 910 and the lower layer 918. The upper fluid passage may include the upper channel spacer layer 912. The lower fluid passage may include the lower channel spacer layer 916. In some embodiments where the upper layer 910 extends further at the distal end 905 than the intermediate layer 914, the upper channel spacer layer 912 may also extend further at the distal end 912 than the intermediate layer 914 and the lower channel spacer layer 916 to support the upper layer 910. As shown in FIGS. 9A-C, in some embodiments, the distal ends of the layers 910, 914, and 918 and the channel layers 912 and 916 are enlarged at their distal ends (to be placed over a wound site), and may form a "teardrop" or other enlarged shape. The distal ends of at least the layers 912 and 916 may also be provided with at least one through aperture. This aperture may be useful not only for the drainage of wound exudate and for applying negative pressure to the wound, but also during manufacturing of the device, as these apertures may be used to align these respective layers appropriately. In further embodiments, the upper fluid channel may further include an auxiliary spacer layer 970 placed under the distal end of the upper channel spacer layer 912 and distally of the distal end of the lower channel spacer layer 916, such that the auxiliary spacer layer 970 supports the distal end of the upper channel spacer layer 912. As shown in FIGS. 9A and 9C, the auxiliary spacer layer 970 may include one or more apertures, which may be aligned with the one or more apertures at the distal end of the spacer layer 912.

In some embodiments, as shown in FIGS. 9A and 9C, the suction adapter 900 includes two apertures at the lower layer 918: an air leak channel aperture 952 and the suction aperture 954, both formed at the lower layer 918, for example at the enlarged distal end of the lower layer 918. In some embodiments, the air leak aperture 952 and/or the suction aperture 954 may be formed as multiple smaller holes. As illustrated, the apertures 952 and 954 may be spaced apart, with aperture 954 located proximally of aperture 952. These apertures may both be located on a central longitudinal axis of the lower layer 918, or one or both apertures may not be located on the central longitudinal axis. The applicator 920 may have two openings 962 and 926 configured to be aligned with the air leak channel aperture 952 and the suction aperture 954.

As shown in FIG. 9C, the air leak channel aperture 952 may be fluidically connected to the upper fluid channel having the upper channel spacer layer 912, thereby forming an air leak flow extending distally from the air leak 924 to the air leak channel aperture 952. As shown in FIG. 9C, this air leak flow extends through the auxiliary spacer layer 970. Also, the suction aperture 954 may be fluidically connected to the lower fluid channel having the lower channel spacer layer 916, thereby forming a suction flow extending distally from the connector 904 and/or a source of negative pressure.

In some embodiments, the upper layer 910 may form a fluid tight seal with the intermediate layer 914 and/or the lower layer 918, and the intermediate layer 914 may form a fluid tight seal with the lower layer 918, such that the upper fluid channel extending distally from the air leak 924 to the air leak channel aperture 952 may be fluidically separate with the lower fluid channel extending distally from the connector 904 to the suction aperture 954. As shown in FIG. 9C, in some embodiments, the distal end of the intermediate layer 914 may extend between the auxiliary spacer layer 970 and the lower channel spacer layer 916 and sealed with the lower layer 918, thereby separating the upper fluid channel and the lower fluid channel. The upper layer 910, the intermediate layer 914, and the lower layer 918 may be sealed to one another using any means described previously herein, for example by melting, welding, or with adhesives.

The air leak aperture 952 and the suction aperture 954 may be sufficiently spaced from each other, such that wound exudate pulled to the suction aperture 954 does not enter the air leak aperture 952. In some embodiments, the upper fluid channel may include a filter (not shown) adjacent the air leak aperture 952 to prevent entering of wound exudate into the upper fluid channel and block the upper fluid channel. The filter may be permeable to air to allow the air from the air leak to be provided to the wound dressing, but may be impermeable to liquid or bacteria. The filter disposed at the air leak aperture 952 may be similar to the filter 5525 described herein previously.

In some embodiments, the lower fluid channel may include a filter (not shown) adjacent the suction aperture 954. The filter may be configured to substantially prevent wound exudate from entering the lower fluid channel. Preferably, the filter may be impermeable to liquids, but permeable to gases, and is provided to act as a liquid barrier and to ensure that no liquids are able to escape from the wound dressing, thereby a canister to collect the wound fluid may not be needed between the suction adapter and a source of negative pressure. The filter may be hydrophobic. The filter can be attached or sealed to the suction adapter and/or the cover film over the wound dressing. For example, the filter may be molded into the suction adapter 900, or may be adhered to the lower layer 918 of the suction adapter 900 using an adhesive such as, but not limited to, a UV cured adhesive.

The auxiliary spacer 970 may be constructed from any flexible material suitable for transmitting air from the controlled air leak. The auxiliary spacer 970 may be constructed from any material suitable for the upper channel spacer layers 912, 5512 and the lower channel spacer layers 916, 5516 as described herein previously, for example open-celled foams such as polyethylene or polyurethane, or a fabric such as a knitted or woven spacer fabric (such as a knitted polyester 3D fabric, Baltex 7970®, or Gehring 879®) or a nonwoven material.

In the illustrated embodiment 900 of FIGS. 9A and 9C, the double-sided adhesive tape 928 is adhered around the suction apertures 926 and 954, thereby securing the applicator 920 to the lower layer 918. However, in some embodiments, the double-sided adhesive tape 928 may be sized and shaped to be adhered around the air leak apertures 952 and 962, or both the apertures 962/952 and 926/954. In some embodiments, the suction adapter 900 may include an additional double-sided adhesive tape (not shown) similar to the adhesive tape 928, to be adhered around the air leak apertures 952 and 962. In some embodiments, additionally or alternatively to the double-sided adhesive tape(s), the applicator may be attached to the lower layer 918 with glue and/or welding.

During operation, the embodiment described in FIGS. 9A-C provides for an air leak path extending into the wound dressing that is fluidically separated from the suction flow path extending from the wound dressing to the source of negative pressure. This embodiment differs from the embodiment of FIGS. 5A-6, where the air leak path fluidically connects with the suction flow path above the wound dressing. In the embodiment of FIGS. 5A-6, if the aperture 5526 is blocked, for example is the suction adapter is not properly positioned over an opening formed in a wound cover placed over a wound or if the aperture 5526 is blocked by wound exudate, the negative pressure source may continue to operate and draw air from the suction adapter by drawing air from the air leak. This could make it difficult to detect the blockage of the suction adapter or the misalignment of the suction adapter over the opening in the wound cover. By having an air leak path fluidically separated from the suction flow path as described herein, if the suction aperture 926 is blocked, the negative pressure source may cease to draw air from the suction adapter, since the air leak will only flow through the wound. This therefore enables detection of blockage of the suction adapter. Further, by having separated controlled air leak path, it would be easier to measure flow or pressure through the suction flow path without interference of the air leak.

Even though FIGS. 9A-C illustrates an example of the flexible suction adapter 900 having a fluidically separate or isolated air leak channel (the upper fluid channel) and suction channel (the lower fluid channel), other arrangements for the flexible suction adapter 900 having fluidically separate of isolated air leak and suction channels are possible. For example, the air leak channel and the suction channel may be disposed side-by-side, instead of one channel being placed on top of the other. In some embodiments, two physically separated soft tubes may be connected to the wound bed, wherein one tube would act solely as a means to allow transmission from the source of negative pressure and the other tube solely act as an air leak channel to allow air from the controlled air leak to flow into the wound.

Figure 10:
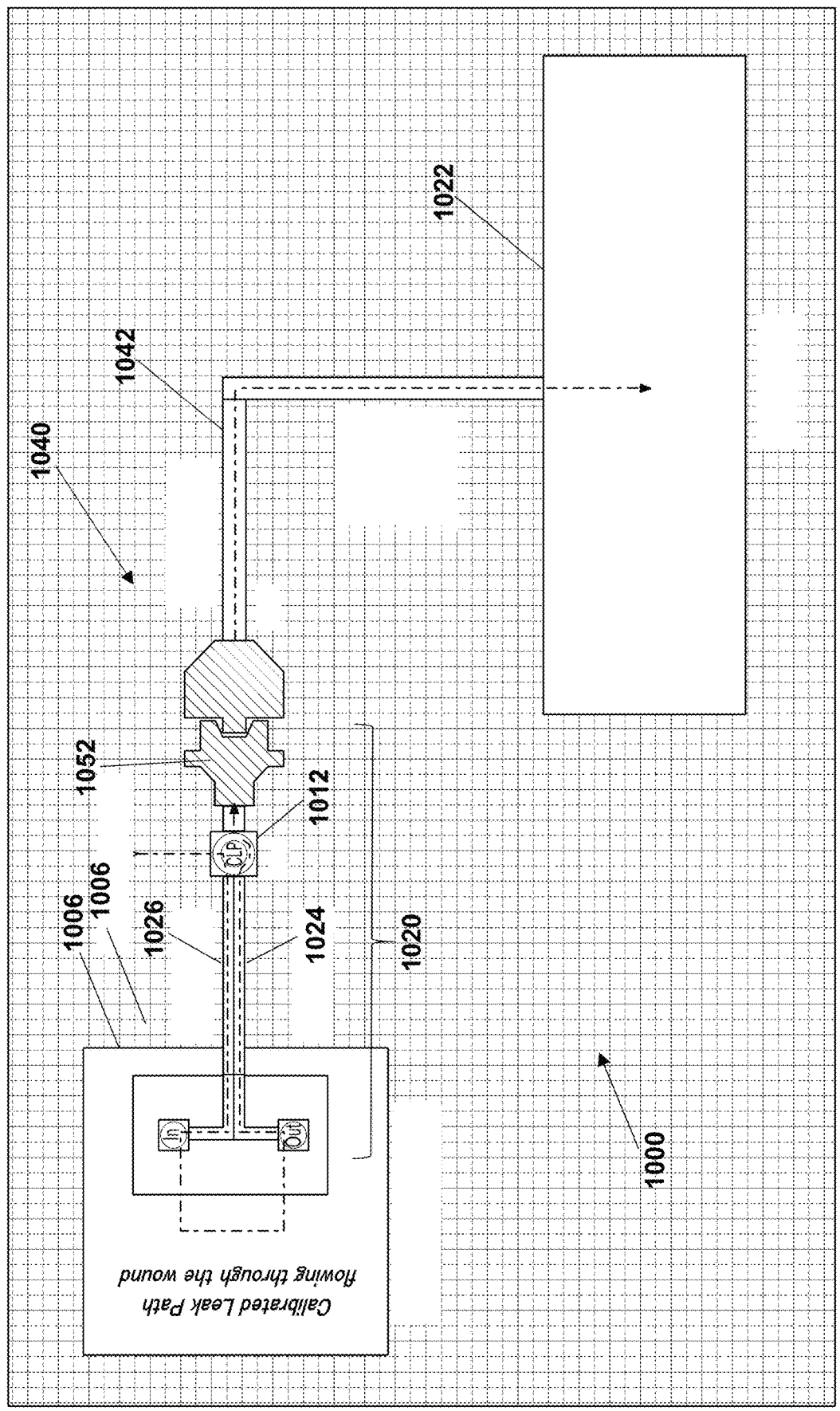
FIG. 10 illustrates a diagram of a system for applying negative pressure according to some embodiments.

FIG. 10 illustrates a diagram of a system 1000 for applying negative pressure according to some embodiments, for example utilizing the suction adapter 900 or any suction adapters having a separated air leak path. As illustrated, the system 1000 includes a source of negative pressure 1022 in fluidic connection with the wound dressing 1006, via fluid flow path 1040, so as to supply negative pressure to one or more wound sites. The fluid flow path 1040 includes a suction adapter 1020 and a tube 1042, which are connected by a connector 1052. The suction adapter 1020 also includes an air leak 1012 configured to admit air into the suction adapter 1020.

As illustrated in FIG. 10, the suction adapter 1020 includes a calibrated leak path 1026 and a suction path 1024. The suction path 1024 is fluidically connected to the fluid flow path 1040 through the connector 1052, so as to supply negative pressure to the wound site through the wound dressing 1006. The calibrated leak path 1026 is fluidically connected to the air leak 1012, so as to supply air from air leak into the wound through the wound dressing 1006. As shown in FIG. 10, the calibrated leak path 1026 and the suction path 1024 may be fluidically connected to each other only through the wound as described herein previously in relation to FIGS. 9A-C. In some embodiments, the air leak 1012 may be disposed at any suitable location in a fluid flow path. For instance, the air leak 1012 can be incorporated into the connector 1052. In some embodiments, the air leaks can be electronically or electromechanically adjusted by a controller of the system to close or widen the leak. For instance, a controller can communicate with the air leaks to open or close each air leak individually or as a unit. For instance, the air leaks can be solenoid valves. The communication between the air leaks and the controller can be wired or wireless.

In some embodiments, the suction adapter 1020 is able to maintain a constant leak rate through the air leak 1012 while negative pressure is applied through a source of negative pressure. Some embodiments may support an air leak of 1, 2, 3, 4, 5, 6, 7, 8, 9 mL/min or more (+/−0.5 mL/min or another suitable deviation). Some embodiments may support an air leak of 10, 20, 30, 40, 50, 60, 70, 80, 90 mL/min, or more (+/−a few mL/min or another suitable deviation). Some embodiments may support an air leak of 0.1, 0.2, 0.3, 0.4, 0.5, 0.6, 0.7, 0.8, 0.9 L/min, or more (+/−a few centiliters/min or another suitable deviation). In some instances, the leak rate can be discussed in terms of controlled leak pathways (CLPs), where CLP is a suitable constant. For instance, an air leak may have a leak rate of 0.25, 0.5, 1, 2, 3, 4, 5, 6, 7, 8, 9, 10, or more. For example, assuming that a leak rate of 0.1 L/min, 1 CLP may correspond to 0.1 L/min, 5 CLPs may correspond to 0.5 L/min, and so on. The negative pressure source must work harder in presence of higher intensity air leak, which can drain the power source faster. Thus, in some embodiments, a relatively low leak rate is chosen.

Multiple Dressing Negative Wound Therapy

Figure 11A:
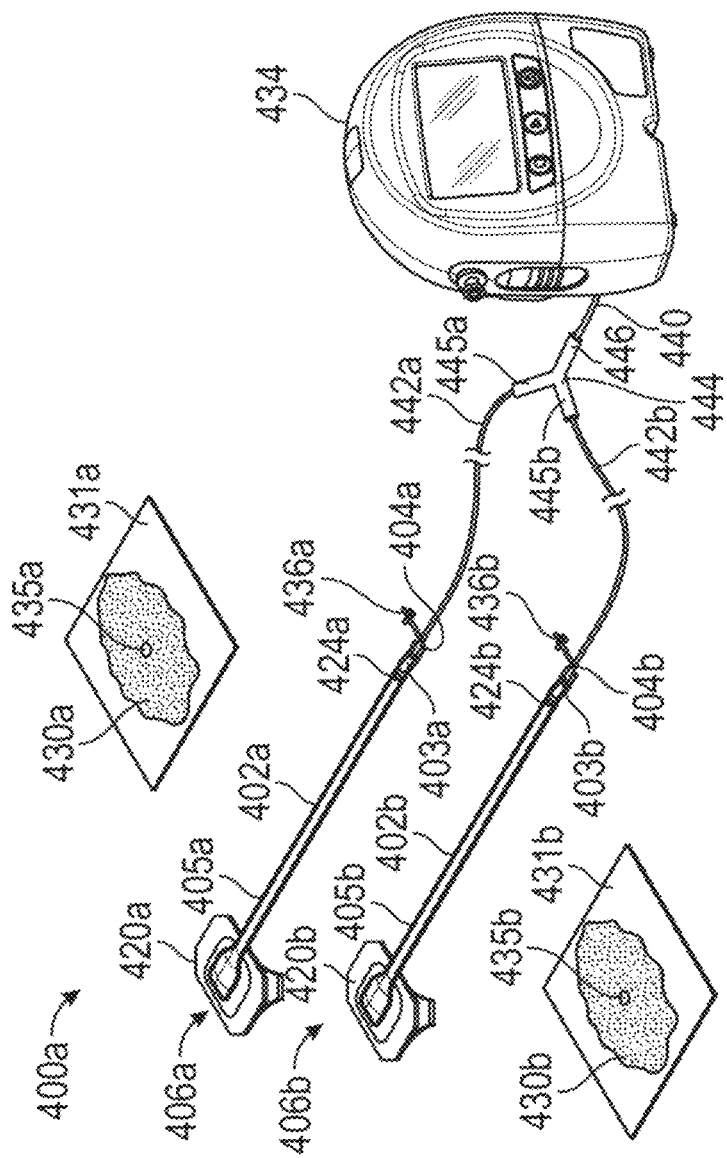
FIG. 11A illustrates a negative pressure wound treatment system including a negative pressure device and illustrating a pair of flexible suction adapters being applied to a wound according to some embodiments.
Figure 11B:
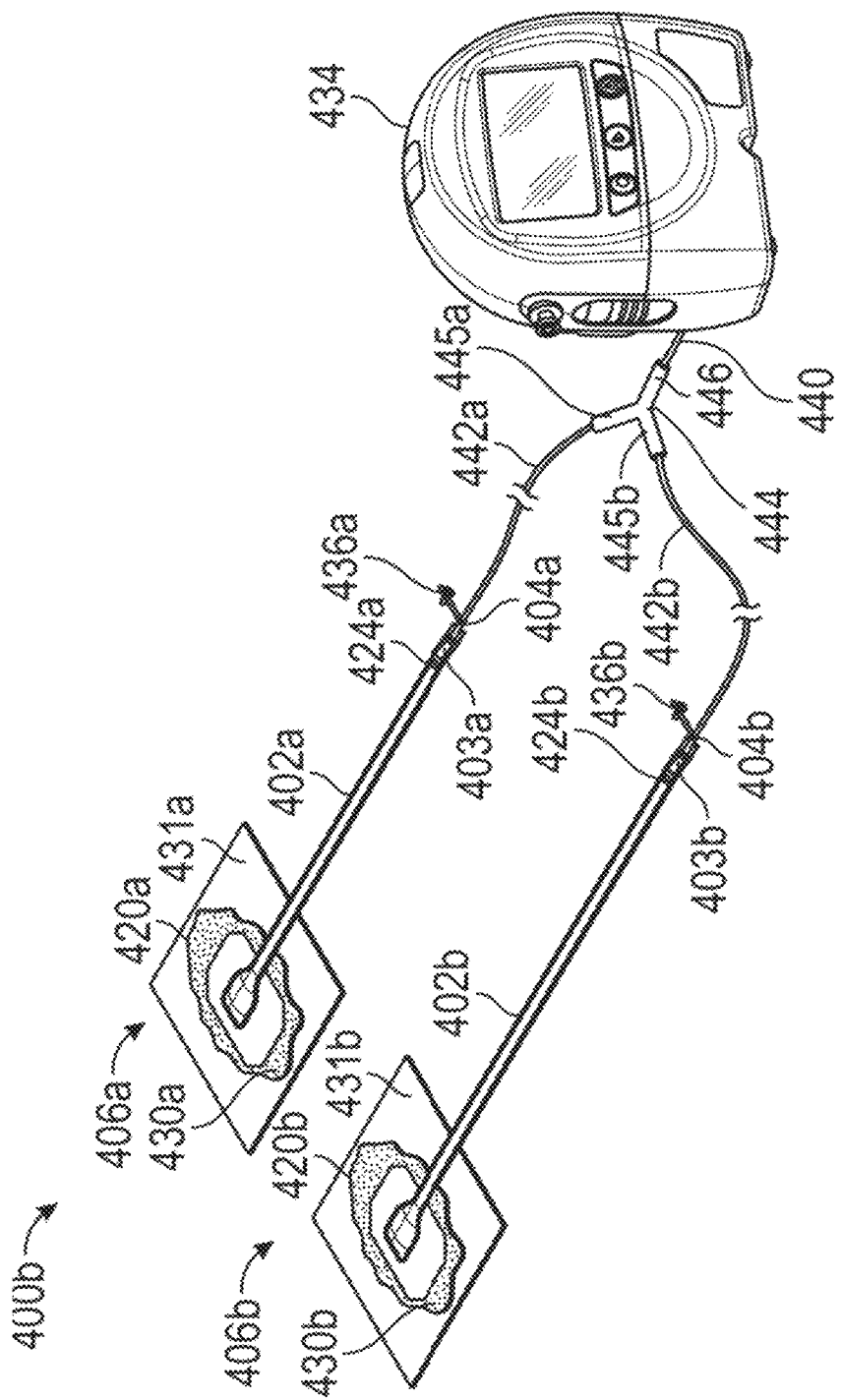
FIG. 11B illustrates an embodiment of FIG. 11A, with the flexible suction adapters having been placed over a wound.

FIGS. 11A-11B illustrate a negative pressure wound treatment system 400 according to some embodiments. The system 400a, 400b (collectively 400) may include a pump assembly or negative pressure unit 434 capable of supplying negative pressure. In some embodiments, the negative pressure unit 434 is the same as that depicted in FIG. 2. The negative pressure unit 434 may be in fluidic connection with one or more wound dressings 406a, 406b (collectively referred to as 406) so as to supply negative pressure to one or more wounds. In some embodiments, the fluidic connection between a wound dressing 406 and a negative pressure unit 434 is referred to as a fluid flow path (e.g., the path through which fluid aspirated from a wound via negative pressure flows). For instance, a first fluid flow path can include components providing fluidic connection from the negative pressure unit 434 to a first wound dressing 406a. As a non-limiting example, the first fluid flow path can include the path from the wound dressing 406a to the negative pressure unit 434 or the path from the first wound dressing 406a to an inlet of a branching attachment 444 in fluidic connection with the negative pressure unit 434. As illustrated, the system 400 can include a plurality of wound dressings (and corresponding fluid flow paths) in fluidic connection with the negative pressure unit 434 via a plurality of suction adapters such as the suction adapters 900 described in relation to FIGS. 9A-C and/or the suction adapters 1020 described in relation to FIG. 10. Accordingly, descriptions for the suction adapter 900 and 1020 and their components herein may also apply to the suction adapters in the systems 400a and 400b and their components. For example, the suction adapters for the systems 400a and 400b may include a controlled leak channel fluidically separate of a suction channel. Each wound dressing and fluid flow path can include a variety of features or elements which match or are similar to features or elements of another wound dressing or fluid flow path within the system. For ease of reference, one or more corresponding features or elements may be collectively referred using a reference number without a corresponding letter. For example, bridge 402a and bridge 402b may be collectively referred to as bridge 402. However, it should be noted that, in some embodiments, elements which have been collectively referred to are not identical and can have different features or attributes.

Referring to FIG. 11A, the system 400a may include a suction adapter such as the suction adapter 900 or 1020, including a bridge 402 having a proximal end 403 and a distal end 405 and an applicator 420 at the distal end 405 of the bridge 402 forming a flexible suction interface or adapter. The negative pressure unit 434 can include a canister or other container for the storage of wound exudates and other fluids that may be removed from the wound. The negative pressure unit 434 may be the negative pressure unit 5534 described in relation to FIG. 2. Alternatively or in addition, the wound dressing 406 may collect the wound exudates and other fluids, and the canister may not be present. In some embodiments, multiple canisters are provided, for instance, one canister per wound dressing. In some embodiments, the negative pressure unit 434 can be a Renasys Touch device, as manufactured by Smith & Nephew. In some embodiments, connectors other than Renasys Soft Port or devices other than Renasys Touch can be used.

FIG. 11B illustrates an embodiment of FIG. 11A, with the flexible suction adaptor having been placed over a wound. In some embodiments, the applicator 420 is placed over an aperture 435 formed in a drape 431 that is placed over a suitably-prepared wound 430, which may in some cases be filled with a wound packing material such as foam or gauze. Subsequently, with the negative pressure unit 434 connected via a tube 440 or an inlet manifold branching attachment or connector 444 to the connector 404, the negative pressure unit 434 is activated, thereby supplying negative pressure via the fluid flow paths to the wounds. Application of negative pressure may be applied until a desired level of healing of the wounds 430 is achieved. Although two wounds and wound dressing are illustrated in FIGS. 11A-11B, the negative pressure unit 434 can provide treatment to more than two wounds in some embodiments. In some implementations, negative pressure wound therapy can be provided to a single wound.

Attachment

The negative pressure unit 434 may be in fluidic connection with the wound dressings 406 via one or more tubes 440, 442, one or more bridges 402, or via an inlet manifold branching attachment 444. For example, the negative pressure unit 434 may be in fluidic connection with a plurality of wound dressings 406 via a tube 440, an inlet manifold branching attachment 444, a tube 442, and a bridge 402. As another example, the manifold branching attachment 444 can be connected directly to the negative pressure unit 434 without using the tube 440. As illustrated in FIGS. 11A-11B, the inlet manifold branching attachment 444 can be configured to connect the negative pressure unit 434 to a plurality of fluid flow paths via a plurality of dressing conduit attachment portions 445a, 445b. The inlet manifold branching attachment 444 can include any number of dressing conduit attachment portions 445 configured to be fluidically connected to a negative pressure attachment portion 446 via a joint. For example, the inlet manifold branching attachment can include two dressing conduit attachment portions 445a, 445b, three dressing conduit attachment portions, or more than three dressing conduit attachment portions.

The plurality of dressing conduit attachment portions 445 can include a first dressing conduit attachment portion 445a and a second dressing attachment portion 445b. However, it will be understood that more or fewer dressing conduit attachment portions can be included in the inlet manifold branching attachment 444. Each of the dressing conduit attachment portions 445 includes a shaft extending away from a joint and including an inlet distal the joint. The inlets are configured to fluidically connect at least a portion of a fluid flow path to the negative pressure unit 434.

The inlet manifold branching attachment 444 can also include one or more negative pressure attachment portions 446. Each of the negative pressure attachment portions 446 can include a shaft extending away from the joint and an inlet distal the joint. The inlet(s) can be configured to fluidically connect to the negative pressure unit 434. For instance, the inlets can include male or female non-luer connectors to attach to a corresponding male or female connector of a conduit or pump. In some embodiments, a negative pressure attachment portion 446 is attached to the negative pressure unit 434 via a tubing 440 or other conduit. A negative pressure attachment portion 446 can also be attached directly (or can be integrated with) a housing of the negative pressure unit 434.

The inlet manifold branching attachment 444 or the conduit can include incorporated one or more valves, clamps, caps, air leaks, or other flow regulator mechanisms which may be configured to admit fluid into a fluid flow path or, alternatively, block or restrict flow or passage of fluid through a fluid flow path. In some embodiments, valves, air leaks, or other flow regulation mechanisms in the inlet manifold branching attachment 444 can be opened or closed electronically. For instance, a controller of the negative pressure unit 434 can communicate with the valves, air leaks, etc. to open or close each one individually or as a unit. This communication can be wired or wireless.

The dressing conduit attachment portions 445 can include shafts forming the top portions of a Y- (two wound), W- (three wound) or other shape of the inlet manifold branching attachment. The proximal ends of dressing conduit shafts and the distal end of the pump conduit shaft can meet at a joint. In some embodiments, the joint can include a hinge that allows rotation of the shafts about the joint. In some embodiments, the inlet manifold branching attachment can be a W-shaped connector (as illustrated in FIG. 6). In embodiments such as these, the inlet manifold branching attachment can include three or more dressing conduit attachment portions and one negative pressure attachment portion.

The inlet manifold branching attachment can include rigid plastic or flexible plastic tubing and can also or alternatively be encased in a soft silicone sleeve to increase patient comfort and prevent the inlet manifold branching attachment 444 from becoming a pressure point.

In some embodiments, utilizing the inlet manifold branching attachment to attach a negative pressure unit to a plurality of wound dressings 406, the negative pressure unit can aspirate fluid from multiple wounds 430 simultaneously. The performance and wound healing capabilities (such as, fluid management) of such system can be equivalent to or exceed that of a standard single wound dressing with single pump set-up.

In some embodiments, an integrated inlet manifold (not shown) can be used in place of an inlet manifold branching attachment 444. In examples such as these, inlet manifolds can be incorporated (e.g., directly attached) into the negative pressure unit 434 or pump housing such that the one or more fluid flow paths can fluidically connect to the pump via one or more inlets of the integrated inlet manifolds. The integrated inlet manifolds can include a splitting attachment (similar to the Y-shaped or W-shaped branching attachment described herein) or can include one or more separately integrated inlets in fluidic connection with the pump.

Determining Operating Conditions

In some embodiments, the system 400 can apply negative pressure to one or more wounds. The level of negative pressure at one or more of the wounds (for example, under one or more wound dressings) can be sufficiently close to the negative pressure level at the source of negative pressure. For example, an acceptable level of pressure maintained at the wound may be within ±1 mmHg, ±5 mmHg, ±10 mmHg, ±25 mmHg, and the like of the negative pressure setpoint. In some embodiments, this pressure can be maintained at this level within 95% (or another suitable percentage) of the time that the system 400 has negative pressure applied to it. In some embodiments, acceptable pressure levels may include pressure ranges between −40 to −120 mmHg. However, other pressure levels may be used as described herein.

As described in more detail herein, one or more air leaks such as the air leaks 424, 5524, 924, or 1012 in one or more of the fluid flow paths may be utilized to determine one or more operating conditions within the system. For example, an air leak can be a controlled air leak that can admit a relatively constant air, gas, or other fluid flow into a fluid flow path. In some embodiments, the flow into the fluid flow path from an air leak does not appreciably increase as additional negative pressure is applied to the system. However, the presence of an air leak in the system may maintain substantially constant baseline flow through the system when steady state has been achieved (for example, when the negative pressure set point has been reached). In turn, presence of the air leak may require the negative pressure source to work harder to maintain the desired level of negative pressure at the wound(s). Accordingly, the system may determine the presence of one or more operating conditions (such as a blockage, leakage, canister full, misalignment of the suction adapter and the like) by monitoring the flow through the fluid flow path(s), which can be measured directly or indirectly based on, for example, monitoring an activity of the negative pressure source.

In some embodiments, each fluid flow path may include an air leak (such as illustrated in FIGS. 11A-11B) and each air leak of a respective fluid flow path can admit a different flow rate of air, gas, or other fluid into the system. In other words, each air leak of the system can have a different leak rate. For example, the leak rate of an air leak can be based at least in part on the size or shape of the air leak, whether the air leak includes a filter, the size or porous level or a filter, a level of occlusion of the air leak or the filter, and the like. The fluid admitted into a fluid flow path increases the flow rate of that fluid flow path.

Accordingly, each fluid flow path of the system 400 can have a different flow rate. The total flow rate (TFR) of the system 400 (e.g., the aggregation of the flow to each of the wound dressings) can be monitored, calculated, or determined and then used to determine an operating condition of the system 400. Operating conditions can, for instance, include a "no flow" condition (e.g., all of the flow paths are blocked), a blockage condition of one or more flow paths (e.g., a blockage condition exists in a first fluid flow path, a blockage condition exists a second fluid flow path, etc.), a canister full condition, normal operation (e.g., no blockages are present in any of the fluid flow paths), and the like.

In some embodiments, the system 400 is capable of providing an indication, such as alarm, to tell the patient or a caregiver an operating status of the system 400 based on a comparison of the determined total flow rate and one or more flow thresholds. In some embodiments, the flow thresholds corresponding to operating conditions of the system 400 are pre-determined. In some embodiments, the flow thresholds are based at least in part on dynamic measurements or calculations of the system 400, such as a flow rate or pressure, during a particular mode of the system (e.g., a calibration mode).

Figure 12:
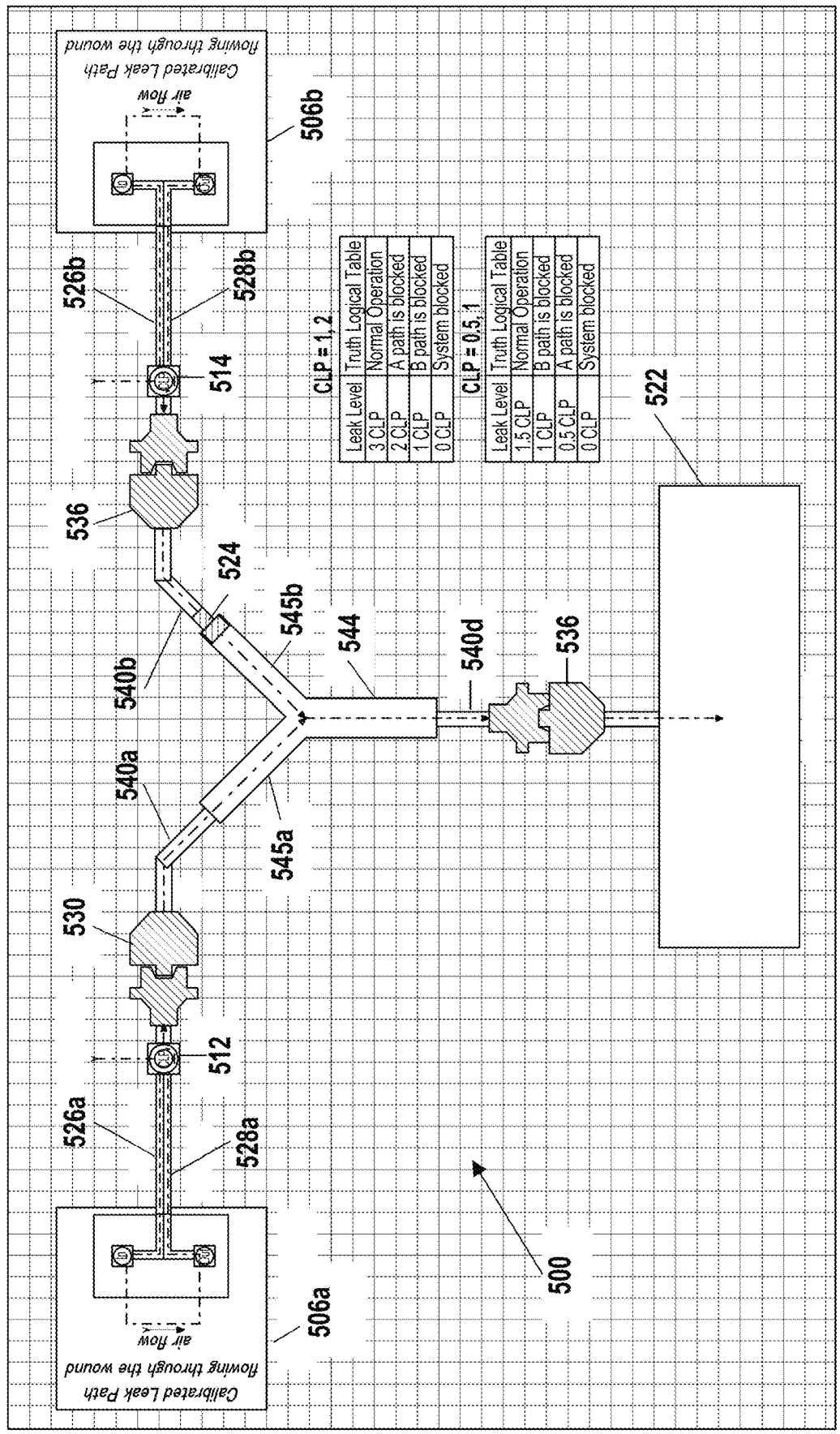
FIG. 12 illustrates a diagram of a system for applying negative pressure according to some embodiments.

FIG. 12 illustrates a diagram of a system for applying negative pressure according to some embodiments. As illustrated, the system 500 includes a source of negative pressure 522 in fluidic connection with wound dressings 506a, 506b via fluid flow path 540d, inlet manifold branching attachment 544, and fluid flow paths 540a, 540b, so as to supply negative pressure to one or more wound sites through suction paths 528a and 528b which are connected with fluid flow paths 540a and 540b respectively. The suction path 528a may be connected with the flow channel 540a with the connector 530, and the suction path 528b may be connected with the flow channel 540b with the connector 530. Each of first fluid flow path 540a and the second fluid flow path 540b include an air leak 512, 514 configured to admit fluid into controlled air leak path 526a and 526b respectively. The controlled air leak path 526a and 526b may be fluidically separated with the suction channel 528a and 528b, such that the controlled air leak paths and the suction paths only fluidically connected through the wound beds.

In some embodiments, the air leaks can be electronically or electromechanically adjusted by a controller of the system to close or widen the leak. For instance, a controller can communicate with the air leaks to open or close each air leak individually or as a unit. For instance, the air leaks can be solenoid valves. The communication between the air leaks and the controller can be wired or wireless.

In some embodiments, the system 500 or 1000 is able to maintain a constant leak rate through an air leak while negative pressure is applied through a source of negative pressure. Some embodiments may support an air leak of 1, 2, 3, 4, 5, 6, 7, 8, 9 mL/min or more (+/−0.5 mL/min or another suitable deviation). Some embodiments may support an air leak of 10, 20, 30, 40, 50, 60, 70, 80, 90 mL/min, or more (+/−a few mL/min or another suitable deviation). Some embodiments may support an air leak of 0.1, 0.2, 0.3, 0.4, 0.5, 0.6, 0.7, 0.8, 0.9 L/min, or more (+/−a few centiliters/min or another suitable deviation). In some instances, the leak rate can be discussed in terms of controlled leak pathways (CLPs), where CLP is a suitable constant. For instance, an air leak may have a leak rate of 0.25, 0.5, 1, 2, 3, 4, 5, 6, 7, 8, 9, 10, or more. For example, assuming that a leak rate of 0.1 L/min, 1 CLP may correspond to 0.1 L/min, 5 CLPs may correspond to 0.5 L/min, and so on. The negative pressure source must work harder in presence of higher intensity air leak, which can drain the power source faster. Thus, in some embodiments, a relatively low leak rate is chosen.

In some embodiments, the first air leak 512 has a different leak rate different than the second air leak 514. For instance, the first air leak can have a leak rate of 1 CLP and the second air leak can have a leak rate of 2 CLP. Alternatively, the first air leak can have a leak rate of 0.5 CLP and the second air leak can have a leak rate of 1 CLP. However, it should be noted that the leak rates of system can be any suitable flow rates. Because of the differing leak rates, the first and second fluid flow paths 520a, 520b can have differing flow rates. Alternatively, the first air leak 512 and the second air leak 514 can be equal or approximately equal (e.g., +/−0.1 L/min or another suitable deviation). For instance, the first air leak 512 and the second air leak 514 can each have a leak rate of 1 CLP. However, it should be noted that the leak rates of system can be any suitable flow rates. Because of the equal leak rates, the first and second fluid flow paths 520a, 520b can have similar flow rates. In some embodiments, the total flow rate (TFR) of the system is an aggregation of the flow coming from the one or more wound dressings of the system. Thus, in some instances, the TFR can be equivalent to the flow rate of fluid flow path 520d.

Flow Rate Monitoring

The system 500 or 1000 can monitor or determine a TFR in the system based, for example, on monitoring the activity of the negative pressure source 522 or 1022. In certain embodiments, flow rate monitoring can be performed by a pump control processor (such as the pump control processor 370 of FIG. 3) alone or in combination with a processor (such as the user interface processor 310 of FIG. 3). Monitoring the flow rate can be used, among other things, to ensure that therapy is properly delivered to one or more wounds, to detect blockages, canister full conditions, no flow conditions, or leaks in one or more fluid flow paths, high pressure, ensure that the flow rate is not unsafe (e.g., dangerously high), etc.

In certain implementations, the system performs flow rate monitoring directly by, for example, using one or more flow meters positioned in the fluid flow path. In some embodiments, the system performs flow rate monitoring indirectly by measuring or monitoring activity of the negative pressure source, such as by monitoring the activity of an actuator. For instance, the system can monitor the activity of a vacuum pump motor, including monitoring the speed of the vacuum pump motor using a tachometer, monitoring current or voltage supplied to the pump (such as, the current or voltage of PWM signal), and the like. The system can continuously monitor one or more of these characteristics to determine activity of the negative pressure source.

In some embodiments, a tachometer (such as a Hall effect sensor) can be used to measure the level of activity of pump motor. The tachometer can be read periodically, such as every 100 msec or another suitable time period, and periodic readings made over a time duration, such as 32 sec or another suitable time duration, can be combined (e.g., averaged). Combined tachometer readings can be used for determining the flow rate, which can in turn be used for leak detection, blockage detection, limiting the maximum flow rate, etc. Combined tachometer readings (e.g., in counts or pulses) can be converted to a flow rate (e.g., in mL/min) using one or more conversion equations or tables so that a TFR of the system (e.g., an aggregation of the flow in each fluid flow path associated with a wound dressing) is determined. In some embodiments, the TFR is determined according to the following equation:

$$TFR=C_1*F*P+C_2$$

where TFR is the total flow rate, F is the frequency of the pump tachometer signal, P is pressure produced by the pump (for example, negative pressure setpoint), and $C_1$ and $C_2$ are suitable constants (determined for given negative pressure source). The determined flow rate can be compared to various flow rate thresholds, such as one or more blockage thresholds, to determine a presence of a particular condition, such as a blockage, leakage, canister full, etc.

In some embodiments, a total flow rate can be determined for the system. TFR can correspond to the sum of the leak rates seen by the negative pressure source. For instance, an expected TFR can be determined, for instance, in a calibration mode, using one or more conversion equations or tables, and the like. The expected TFR can correspond to the TFR of the system in steady state operation (for example, when the negative pressure set point has been reached) if no air leaks are present and the like. The system can then monitor the TFR and compare it to one or more leak or flow rate thresholds to determine a presence of a particular condition, such as a blockage, no flow, normal operation, canister full, etc. In some implementations, the expected TFR can be determined in non-steady state. In certain cases, more than one expected TFR can be utilized.

In some embodiments, a blockage condition is detected when the determined flow rate fails to satisfy one or more flow thresholds. For instance, a blockage alarm can be enabled if the blockage condition is present for a period of time, such as 30 seconds or another suitable period of time. This approach can implement hysteresis so that transient events do not cause the system to erroneously report presence of one or more operating conditions. In embodiments where the system includes more than one wound dressing, a different blockage alarm can be enabled for each wound dressing. The blockage alarm can be disabled when the determined flow rate exceeds the one or more flow thresholds. In some embodiments, the system can differentiate between a blockage in one or more fluid flow paths and canister full conditions.

In some embodiments, blockages and presence of fluid in one or more fluid flow paths are detected by processing data from one or more pressure sensors (not shown), which can be positioned in any suitable location in the flow path. In some embodiments, a pressure sensor is positioned at or near an inlet of the negative pressure source. This detection can be enhanced by changing one or more settings of the pump, such as increasing pressure level delivered by the pump, decreasing the pressure level, stopping the pump, changing the pump speed, changing a cadence of the pump, and the like.

In some embodiments, flow rate can be estimated as the air, gas, or other fluid volume moving in the fluid flow path per unit of time normalized to standard temperature and standard pressure (e.g., 1 atm). Flow rate can be periodically computed, such as every 250 milliseconds or any other suitable time value, according to the following formula:

$$TFR=Slope*Tachometer+Intercept$$

Tachometer is short tachometer average (for example, an average of most recent tachometer readings (e.g., over 2.5 seconds or another suitable period of time), which can be measured in Hz) and Slope and Intercept are constants that are based on the negative pressure setpoint. The values for Slope and Intercept can be determined for possible pressure setpoints (e.g., −25 mmHg, −40 mmHg, −50 mmHg, −60 mmHg, −70 mmHg, −80 mmHg, −90 mmHg, −100 mmHg, −120 mmHg, −140 mmHg, −160 mmHg, −180 mmHg, −200 mmHg) for a given negative pressure source. The flow as a function of the pump speed may not be a best fit as a single line because the pump can be designed to be more efficient at lower flow rates. Because of this, slope and intercept values can be pre-computed for various setpoints and various pumps. As described herein, the determined flow rate can be compared to various flow thresholds to determine a presence of a particular operating condition, such as a blockage condition, no flow condition, canister full condition, abnormal condition, normal condition, etc.

In addition, the system can determine and monitor pressure in a fluid flow path using one or more sensors. For instance, a fluid flow path can include a pressure sensor at or near a wound dressing 406, at or near an inlet manifold branching attachment 444, or anywhere else on the fluid flow path. In some embodiments, the pump assembly includes a pressure sensor in or near the inlet (or canister connection) of the pump assembly. This pressure sensor can measure the pressure in the canister (or in or near the dressing in a canisterless system). The pump assembly can continuously measure pressure in the canister, such as every millisecond or any other suitable duration. A suitable number of latest pressure sensor readings can be averaged to mitigate the effects of one or more errant readings.

Based on the determined total flow rate, the pump assembly can monitor and detect various operating conditions as described herein. One or more of these conditions can be detected by, for instance, flow chart 700 or 800 illustrated in FIGS. 13 and 14. A blockage in one or more fluid flow path can be determined by comparing the total flow rate to one or more flow thresholds. The comparison can implement hysteresis, such as be continuously or substantially continuously performed over or during a period of time, such as 2 minutes or any other suitable duration. The one or more flow thresholds can be selected or determined based on the particular pressure setpoint since the expected TFR may also depend on the setpoint. That is, to detect blockages, the pump assembly can utilize a plurality of flow thresholds corresponding to particular pressure setpoints. Alternatively or in addition, flow thresholds can be selected or determined based on the leak rates of the one or more air leaks. As explained herein, the flow rate can be indirectly determined by detecting and monitoring the pump speed.

If one or more flow thresholds are satisfied or not satisfied (e.g., over a period of time), the system determines that there is a blockage in at least one of the fluid flow paths and provides an indication, which can include activating an alarm (e.g., visual, audio, or tactile), pausing operation of the negative pressure, or the like. For example, to determine presence of a blockage, the pump assembly can determine whether the total flow rate satisfies, exceeds, or falls below a flow threshold during a 2 minute period of time or during any other suitable period of time. Because total flow rate may be updated at periodic time intervals due to periodic sampling of the tachometer, the pump assembly may compare the total flow rate as it is being updated to the flow threshold over the 2 minute period of time. Blockage can be detected provided that each total flow rate determined during the 2 minute interval satisfies, exceeds, or falls below a flow threshold. Alternatively or additionally, blockage can be detected if the majority of calculated total flow rates, such as 9 out of 10 or any other suitable number, satisfy, exceed, or fall below a flow threshold. Detected blockages may be cleared when the total flow rate falls below (or exceeds) one or more flow thresholds for a period of time, such as 5 seconds or any other suitable duration.

The threshold value can be any suitable flow threshold, such as a value selected or determined based on the negative pressure setpoint and expected flow rate in the fluid flow path, which can be determined as described herein.

In some embodiments, one or more flow sensors or flow meters can be used to directly measure the fluid flow. In some embodiments, the pump assembly can utilize one or more of the techniques described herein in parallel to control the pump and to detect various conditions. The pump assembly can be configured to suitably arbitrate between using parameters determined by different techniques. For example, the pump assembly can arbitrate between flow rates determined indirectly, such as based on the pump speed as measured by a tachometer, and directly, such as by using a flow meter. In certain embodiments, the pump assembly can indirectly determine the flow rate and resort to direct determination of the flow rate when needed, such as when indirectly determined flow rate is perceived to be inaccurate or unreliable.

In some embodiments, selecting or activating a Y- or W-connect features for treatment of multiple wounds, can alter or modify detection of one or more operating conditions, such as blockages, leaks, canister full condition, and the like. Activating the Y- or W-connect features can adjust one or more of various thresholds described herein. In some embodiments, the system automatically detects that Y- or W-connector is present. For instance, if a single wound dressing is connected having a leak rate of 1 CLP, the system can automatically detect that a Y-connector is present by detecting a leak higher than the expected 1 CLP leak. For instance, the system may prompt the user to confirm that another flow path with, for example, with a leak rate of 2 CLP is present. Once the user confirms, the system will know to detect blockage and can determine flow thresholds based at least in part of the determination of the leak rates. A similar determination can be used for W-connector with three flow paths. For instance, continuing with the previous example, if the system detects a leak higher than the expected 3 CLP leak, the system can detect that a W-connector is present and may prompt the user to confirm that another flow path with, for example, a leak rate of 4 CLP is present. In some embodiments, similar approaches can be utilized when more than 3 wounds are being treated.

Figure 13:
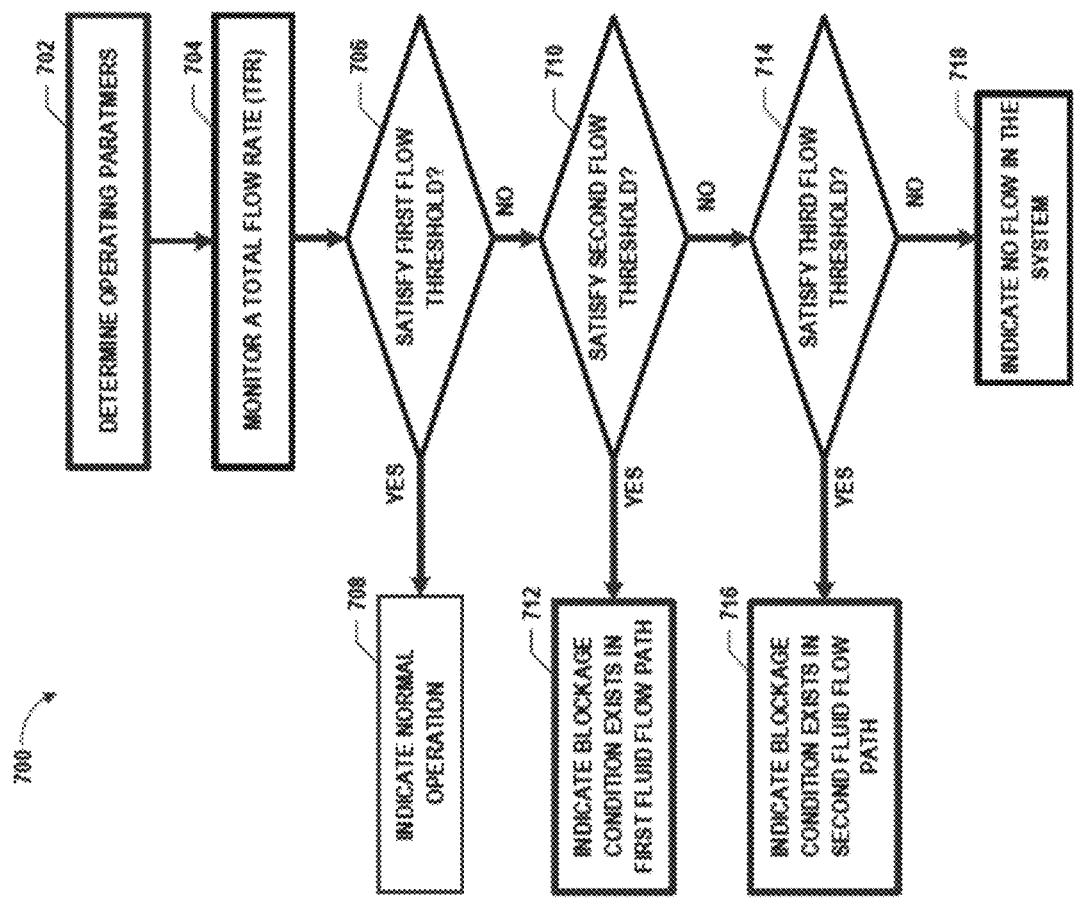
FIG. 13 illustrates a flow diagram of a process for determining and indicating one or more operating conditions according to some embodiments.

FIG. 13 illustrates a flow diagram of a process 700 for determining and indicating one or more operating conditions according to some embodiments. In some embodiments, the process 700 is implemented by reduced pressure wound therapy system 500, such as by one or more controllers of the system.

At block 702, the process 700 determines one or more operating parameters. For example, the process 700 can determine the number of attached wound dressings, whether a fluid flow path corresponding to an attached wound dressings includes an air leak, a leak rate of the one or more air leaks, an expected total flow rate (TFR) of the system, an expected flow rate of each of the fluid flow paths, one or more flow thresholds, a level of activity of the negative pressure source, etc. In some embodiments, the process 600 can perform one or more of such determinations in a calibration mode. Alternatively, some or all of these determinations can be automatically detected or received by the process upon attachment of each wound dressing. In some embodiments, a user can input some or all of the operating parameters or the process can perform internal calculations or can utilize conversion equations or tables.

As described herein, in some embodiments, the process 700 can detect the presence of one or more attached wound dressings by detecting a higher than expected leak rate. For example, the process can automatically detect that a Y-connector is present by detecting a leak higher than the expected leak rate and prompt the user to confirm that another flow path is present. Once the user confirms, the process will determine how to detect a blockage. In other embodiments, the process may detect when a wound dressing is attached and will know the specifications of as air leak based on the attached wound dressing.

The process 700 can also determine an expected flow rate of each of the fluid flow paths corresponding to each of the attached wound dressings. As described herein, each of the fluid flow paths can include one or more air leaks which can be configured to admit fluid into the fluid flow path in which the air leak is located. In addition, each of the air leaks may have a different leak rate (e.g., the rate at which fluid is admitted into the fluid flow path). Accordingly, each of the fluid flow paths can have a different expected flow rate.

Based at least in part on the number of wound dressings or the leak rate of one or more air leaks, the process 700 can determine a plurality of flow thresholds. For example, a process can have two wound dressings, each having a different flow rate. The process can determine a first flow threshold corresponds to a flow rate equal to the aggregation of the expected flow rate of the first fluid flow path and the expected flow rate of the second fluid flow path. A second flow threshold corresponds to the expected flow rate of the second fluid flow path. A third flow threshold corresponds to the expected flow rate of the first fluid flow path. Accordingly, if the monitored TFR satisfies the first flow threshold, then the system is operating normally. If the monitored TFR satisfies the second flow threshold, but not the third flow threshold, then the process can determine that the first fluid flow path is blocked. The process can make this determination because when the flow rate is equal to the expected flow rate of the second fluid flow path, the process is only detecting the flow of the second fluid flow path. As such, the process is not detecting any flow from the first fluid flow path and therefore the process can determine that the first fluid flow path is blocked. In some embodiments, one or more of the thresholds can be higher or lower to than the expected flow rates to, for example, allow for variability during operation.

In some embodiments, the flow thresholds can correspond to the leak rates of the system. For example, a system can have two wound dressings. Each wound dressing can have an associated fluid flow path. The first fluid flow path associated with the first wound dressing includes an air leak of 1 CLP. The second fluid flow path associated with the second wound dressing includes an air leak of 2 CLP. The process 700 can determine a first flow threshold corresponds to a leak rate of 3 CLP, a second flow threshold corresponds to a leak rate of 2 CLP, and a third flow threshold that corresponds to 1 CLP. Accordingly, if the process detects a TFR of 1 CLP (e.g., satisfies the third threshold but does not satisfy the second threshold or third threshold), the process can determine that the second fluid flow path is blocked. The process can make this determination because when TFR is equal to 1 CLP the system is only detecting the flow in the first fluid flow path. As such, the process is not detecting flow from the second fluid flow path and therefore the process can determine that the second fluid flow path is blocked. Similarly, if the process detects TFR of 2 CLP (e.g., TFR satisfies the second threshold and does not satisfy the third threshold), the process can determine that the first fluid flow path is blocked. Likewise, if the process detects TFR of 3 CLP (e.g., TFR satisfies the third threshold), the process can determine that neither the first nor the second fluid flow paths are blocked, and the system is operating normally. Also, if the process detects no flow, the process can determine system blockage due to, for example, all fluid flow paths being blocked or canister being full. This is summarized in the following table:

TABLE 1

| CLPs are 1 and 2 | |
| --- | --- |
| Flow rate | Determination |
| 3 CLP | Normal operation |
| 2 CLP | First fluid flow path is blocked |
| 1 CLP | Second fluid flow path is blocked |
| 0 CLP | System blocked |

In some embodiments, one or more of the thresholds can be higher or lower to account for inaccuracies. For example, although the first air leak is equal to 1 CLP, the first flow threshold provide a small buffer (e.g., 0.03, 0.05, 0.1, 0.15, 0.2, or 0.25 CLP) such that the threshold is slightly below or slightly higher than 1 CLP. Similar buffers can be used for other flow thresholds. For instance, the first and second thresholds can be 0.5 and 1 CLP respectively, and the process can make following determinations:

TABLE 2

| CLPs are 0.5 and 1 | |
| --- | --- |
| Flow rate | Determination |
| 1.5 CLP | Normal operation |
| 1 CLP | First fluid flow path is blocked |
| 0.5 CLP | Second fluid flow path is blocked |
| 0 CLP | System blocked |

At block 704, the process 700 monitors a total flow rate (TFR) utilizing one or more of the flow rate monitoring techniques described herein. The process can suitably arbitrate between flow rates determined using multiple flow rate monitoring techniques if one or more such techniques are executed in parallel. In certain embodiments, the process can execute one of the techniques, such as the flow rate determination based on the pump speed, and utilize one or more other techniques as needed. In various embodiments, the process can utilize one or more other techniques in cases the determine flow rate is perceived to be inaccurate or unreliable. In some embodiments, the total rate of flow corresponds to an aggregation of the flow of each of the flow path in the process. For example, the total rate of flow can correspond to the aggregation of a flow of the first fluid flow path and a flow of the second fluid flow path.

In some embodiments, the monitored TFR can be compared to an expected TFR to determine if the system is operating normally. Accordingly, by comparing the monitored TFR with the expected TFR (for example, by subtracting the expected TFR from the monitoring TFR), the process 700 can determine a deviation in the current flow rate from the expected flow rate. This deviation can be due to presence of one or more operating conditions.

At block 706, the process 700 determines whether the monitored TFR satisfies (for example, is substantially equal to or exceeds) the first flow threshold, which can correspond to expected TFR. If the first flow threshold is satisfied, then, at block 708, the system can indicate the system is operating normally. Indication in block 708 or in any other block of process 700 can be performed using any of the approaches described herein.

If the monitored TFR does not satisfy the first threshold, the process 700 transitions to block 710, where it determines whether the monitored TFR satisfies the second flow threshold. If the second flow threshold is satisfied (for example, TFR is substantially equal to or is above the second flow threshold), then, at block 712, the process 700 can indicate a blockage condition exists in the first fluid flow path. The process can make this determination because, based upon determining that the TFR satisfies the second threshold (and does not satisfy the first flow threshold), the process can determine it is only detecting flow from the second fluid flow path.

If the monitored TFR does not satisfy the second threshold, the process 700 transitions to block 714, where it determines whether the monitored TFR satisfies the third flow threshold. If the third flow threshold is satisfied (for example, TFR is substantially equal to or is above the third threshold), then, at block 716, the process can indicate a blockage condition exists in the second fluid flow path. The process can make this determination because, based upon determining the TFR satisfies the third threshold (and does not satisfy the first and second thresholds), the process can determine it is only detecting flow from the first fluid flow path.

If the monitored TFR does not satisfy the third threshold, the process 700 transitions to block 718, where it determines and indicate that system is blocked.

While the examples provided in conjunction with the process 700 generally relate to a system having a first and second wound dressing, it should be noted that similar techniques can be performed for a system having any number of wound dressings.

Furthermore, it will be understood that fewer, more, or different blocks can be used as part of the process 700. For example, the process 700 can include fewer blocks if, for instance, one or more leak rates are equal or approximately equal (e.g., +/−0.1 L/min or another suitable deviation). As described above, a system can have two wound dressings and each wound dressing can have an associated fluid flow path. For example, the first fluid flow path associated with the first wound dressing can include an air leak of 1 CLP, and the second fluid flow path associated with the second wound dressing can also include an air leak of 1 CLP. Accordingly, the process 700 can utilize two flow thresholds: a first flow threshold corresponding to a leak rate of 2 CLP, and a second flow threshold corresponding to a leak rate of 1 CLP. If the process 700 detects a TFR of 1 CLP (e.g., satisfies the first threshold but does not satisfy the second threshold), the process can determine that either the first or second fluid flow path is blocked. The process 700 can make this determination because when TFR is equal to 1 CLP, the process is only detecting the flow from one of the fluid flow paths. In some cases, the process can determine or indicate which fluid flow path is blocked, while in other cases, the process can determine or indicate that a blockage has occurred somewhere in one of the fluid flow paths. If the process 700 detects TFR of 2 CLP (e.g., TFR satisfies the second threshold), the process can determine that neither the first nor the second fluid flow paths are blocked, and the system is operating normally. Also, if the process detects no flow, the process can determine system blockage due to, for example, all fluid flow paths being blocked or canister being full. This is summarized in the following table:

TABLE 3

| CLPs are 1 and 1 | |
| --- | --- |
| Flow rate | Determination |
| 2 CLP | Normal operation |
| 1 CLP | Blockage occurred somewhere in the fluid flow paths |
| 0 CLP | System blocked |

Figure 14:
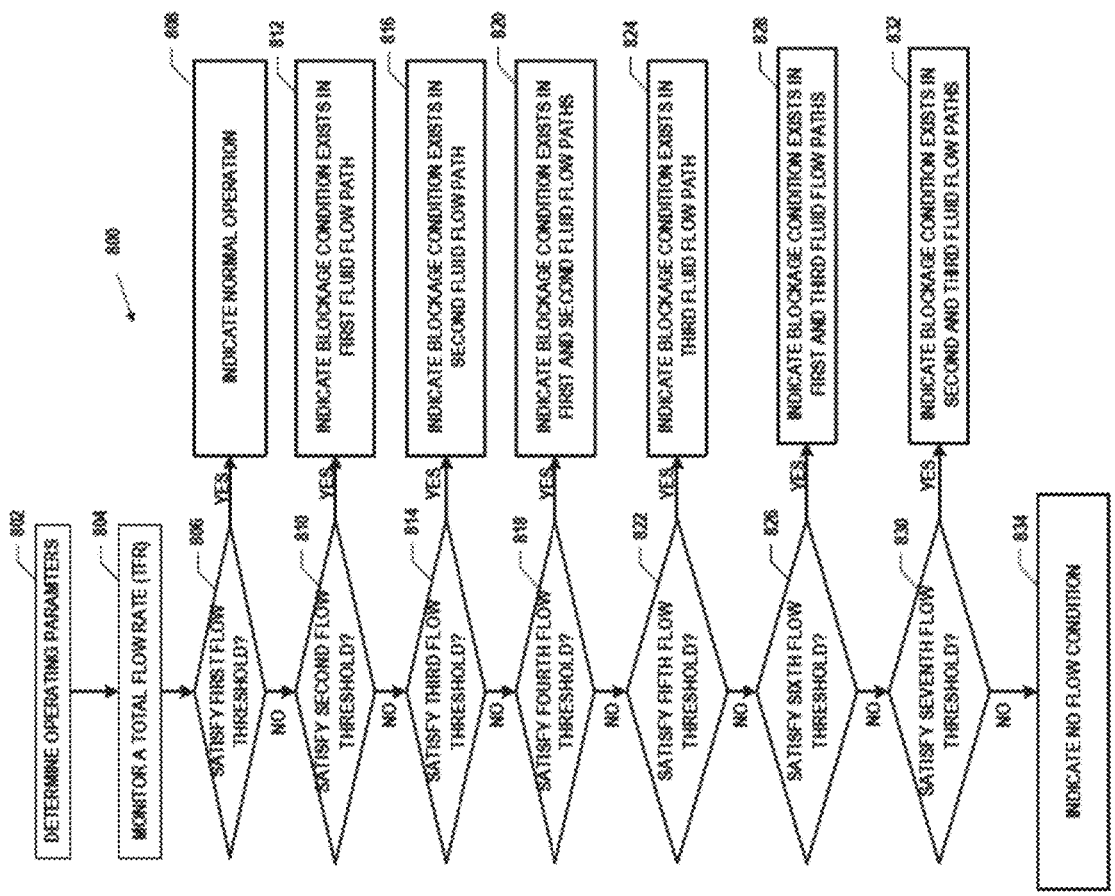
FIG. 14 illustrates a flow diagram of a process for determining and indicating one or more operating conditions according to some embodiments.

FIG. 14 illustrates a flow diagram of a process 800 for determining and indicating one or more operating conditions according to some embodiments. In some embodiments, the process 800 is implemented by reduced pressure wound therapy system 600, such as by one or more controllers of the system.

At block 802, similar to what is described with reference to block 702 of FIG. 7, the process 800 determines one or more operating parameters. For example, the process can determine the number of attached wound dressings, whether a fluid flow path corresponding to an attached wound dressings includes an air leak, a leak rate of the one or more air leaks, a total leak rate, an expected total flow rate (TFR) of the system, an expected flow rate of each of the fluid flow paths, one or more flow thresholds, a level of activity of the pump, etc. In some embodiments, the process can perform some or all of these determinations in calibration mode. Alternatively, some or all of these operating parameters can be automatically detected or received by the process upon attachment of each wound dressing. In some embodiments, a user can input some or all of the operating parameters or the process can perform internal calculations or can utilize conversion equations or tables.

As described herein, the process 800 may detect the presence of one or more attached wound dressings by detecting a higher than expected leak rate. For example, the process can automatically detect that a W-connector is present by detecting a leak higher than the expected leak rate and prompt the user to confirm that another flow path is present. Once the user confirms, the process will know how to detect a blockage. In other embodiments, the process may detect when a wound dressing is attached and will know the specifications of as air leak based on the attached wound dressing.

The process 800 can determine a plurality of flow thresholds. In this example, the process can determine at least seven flow thresholds. However, it should be noted that more or fewer flow thresholds can be determined. As described with respect to block 702 of FIG. 7, the flow thresholds can correspond to TFR of the system in presence of one or more operating conditions.

In some embodiments, a first flow threshold corresponds to a flow rate equal to the aggregation of an expected flow rate of the first fluid flow path (expected first flow rate), the expected flow rate of the second fluid flow path (expected second flow rate), and the expected flow rate of the third fluid flow path (expected third flow rate). A second flow threshold corresponds to a flow rate equal to the aggregation of the expected second flow rate and the expected third flow rate. A third flow threshold corresponds to a flow rate equal to the aggregation of the expected first flow rate and the expected third flow rate. A fourth flow threshold corresponds to a flow rate equal to the aggregation of the expected first flow rate and the expected second flow rate. A fifth flow threshold corresponds to a flow rate equal to the expected third flow rate. A sixth flow threshold corresponds to a flow rate equal to the expected second flow rate. A seventh flow threshold corresponds to a flow rate equal to the expected first flow rate.

For example, the first fluid flow path can have a leak rate of 1 CLP, the second fluid flow path can have a leak rate of 3 CLP, and the third fluid flow path can have a leak rate of 5 CLP. A first flow threshold corresponds to a leak rate equal 9 CLP (e.g., an aggregation of all of the leak rates). A second flow threshold corresponds to a leak rate equal to 8 CLP. A third flow threshold corresponds to a leak rate equal to 6 CLP. A fourth flow threshold corresponds to a leak rate equal to 5 CLP. A fifth flow threshold corresponds to a leak rate equal to 4 CLP. A sixth flow threshold corresponds to a leak rate equal to 3 CLP. A seventh flow threshold corresponds to a leak rate equal to 1 CLP. This is summarized as follows:

TABLE 4

| CLPs are 1, 3 and 5 | |
| --- | --- |
| Flow rate | Determination |
| 9 CLP | Normal operation |
| 8 CLP | First fluid flow path is blocked |
| 7 CLP | N/A or unexpected flow rate |
| 6 CLP | Second fluid flow path is blocked |
| 5 CLP | First and second fluid flow paths are blocked |
| 4 CLP | Third fluid flow path is blocked |
| 3 CLP | First and third fluid flow paths are blocked |
| 2 CLP | N/A or unexpected flow rate |
| 1 CLP | Second and third fluid flow paths are blocked |
| 0 CLP | System blocked |

In some embodiments, order of the flow thresholds may change based on the leak rate of the air leaks.

At block 804, similar to what is described with reference to block 704 of FIG. 7, the process 800 monitors a TFR utilizing one or more of the flow rate monitoring techniques described herein.

At block 806, the process 800 determines whether the monitored TFR satisfies (for example, is substantially equal to or exceeds) the first flow threshold. If the first flow threshold is satisfied, then, at block 808, the process can indicate the system is operating normally. Indication in block 808 or in any other block of process 800 can be performed using any of the approaches described herein.

If the monitored TFR does not satisfy the first flow threshold, the process transitions to block 810, it determines whether the monitored TFR satisfies (for example, is substantially equal to or exceeds) the second flow threshold. If the second flow threshold is satisfied (and the first flow threshold is not satisfied), then, at block 812, the process can indicate a blockage condition exists in the first fluid flow path. The process can make this determination because, based on the satisfied threshold, the process can determine it is only detecting flow from the second and third fluid flow paths.

If the monitored TFR does not satisfy the second flow threshold, the process transitions to block 814, where it determines whether the monitored TFR satisfies (for example, is substantially equal to or exceeds) the third flow threshold. If the third flow threshold is satisfied (and the first and second flow thresholds are not satisfied), then, at block 816, the process can indicate a blockage condition exists in the second fluid flow path. The process can make this determination because, based on the satisfied threshold, the process can determine it is only detecting flow from the first and third fluid flow paths.

If the monitored TFR does not satisfy the third flow threshold, the process transitions to block 818, where it determines whether the monitored TFR satisfies (for example, is substantially equal to or exceeds) the fourth flow threshold. If the fourth flow threshold is satisfied (and the first, second, and third flow thresholds are not satisfied), then, at block 820, the process can indicate a blockage condition exists in the first and second fluid flow paths. The process can make this determination because, based on the satisfied threshold, the process can determine it is only detecting flow from the third fluid flow path.

If the monitored TFR does not satisfy the fourth flow threshold, the process transitions to block 822, where it determines whether the monitored TFR satisfies (for example, is substantially equal to or exceeds) the fifth flow threshold. If the fifth flow threshold is satisfied (and the first through fourth flow thresholds are not satisfied), then, at block 824, the process can indicate a blockage condition exists in the third fluid flow path. The process can make this determination because, based on the satisfied threshold, the process can determine it is only detecting flow from the first and second fluid flow paths.

If the monitored TFR does not satisfy the fifth flow threshold, the process transitions to block 826, where it determines whether the monitored TFR satisfies (for example, is substantially equal to or exceeds) the sixth flow threshold. If the sixth flow threshold is satisfied (and the first through fifth flow thresholds are not satisfied), then, at block 828, the process can indicate a blockage condition exists in the first and third fluid flow paths. The process can make this determination because, based on the satisfied threshold, the process can determine it is only detecting flow from the second fluid flow path.

If the monitored TFR does not satisfy the sixth flow threshold, the process transitions to block 830, where it determines whether the monitored TFR satisfies (for example, is substantially equal to or exceeds) the seventh flow threshold. If the seventh flow threshold is satisfied (and the first through sixth flow thresholds are not satisfied), then, at block 832, the process can indicate a blockage condition exists in the second and third fluid flow paths. The process can make this determination because, based on the satisfied threshold, the process can determine it is only detecting flow from the first fluid flow path.

At block 834, the process 800 determines that no flow thresholds are satisfied, and indicates system blocked condition.

While the examples provided in conjunction with process 800 relate to a system having a first, second and third wound dressings, it should be noted that similar techniques can be performed for a system having any number of wound dressings.

Examples, embodiments, methods, processes or devices for negative pressure wound therapy system with calibrated leak paths are further provided in International Application No. PCT/EP2018/056494, titled "MULTIPLE DRESSING NEGATIVE PRESSURE WOUND THERAPY SYSTEM WITH CALIBRATED LEAK PATHS" and filed Mar. 15, 2018, which is hereby incorporated by reference in its entirety.

Terminology

Depending on the embodiment, certain operations, acts, events, or functions of any of the processes described herein can be performed in a different sequence, can be added, merged, or left out altogether (such as not all are necessary for the practice of the processes). Moreover, in certain embodiments, operations, acts, functions, or events can be performed concurrently, such as through multi-threaded processing, interrupt processing, or multiple processors or processor cores or on other parallel architectures, rather than sequentially.

The processing of the various components of the illustrated systems can be distributed across multiple machines, networks, and other computing resources. In addition, two or more components of a system can be combined into fewer components. Various components of the illustrated systems can be implemented in one or more virtual machines, rather than in dedicated computer hardware systems and/or computing devices. Likewise, the data repositories shown can represent physical and/or logical data storage, including, for example, storage area networks or other distributed storage systems. Moreover, in some embodiments the connections between the components shown represent possible paths of data flow, rather than actual connections between hardware. While some examples of possible connections are shown, any of the subset of the components shown can communicate with any other subset of components in various implementations.

Any patents and applications and other references noted above, including any that may be listed in accompanying filing papers, are incorporated herein by reference. Aspects of the disclosure can be modified, if necessary, to employ the systems, functions, and concepts of the various references described herein to provide yet further implementations.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as processors, ASICs, FPGAs, and the like, can include logic circuitry. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments or uses and obvious modifications and equivalents thereof, including embodiments which do not provide all of the features and advantages set forth herein. Accordingly, the scope of the present disclosure is not intended to be limited by the described embodiments, and may be defined by claims as presented herein or as presented in the future.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Likewise the term "and/or" in reference to a list of two or more items, covers all of the following interpretations of the word: any one of the items in the list, all of the items in the list, and any combination of the items in the list. Further, the term "each," as used herein, in addition to having its ordinary meaning, can mean any subset of a set of elements to which the term "each" is applied. Additionally, the words "herein," "above," "below," and words of similar import, when used in this application, refer to this application as a whole and not to any particular portions of this application.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

Any of the embodiments described herein can be used with a canister or without a canister. Any of the dressing embodiments described herein can absorb and store wound exudate.

The scope of the present disclosure is not intended to be limited by the description of certain embodiments and may be defined by the claims. The language of the claims is to be interpreted broadly based on the language employed in the claims and not limited to the examples described in the present specification or during the prosecution of the application, which examples are to be construed as non-exclusive.

What is claimed is:

1. An apparatus to provide negative pressure to a wound site comprising:
   a top layer, a bottom layer and an intermediate layer, wherein each layer is constructed from a flexible, liquid impermeable material, wherein each of the layers has a proximal end and a distal end;
   an upper fluid passage at least partially defined between the top layer and the intermediate layer, the upper fluid passage having a proximal end and a distal end, wherein the upper fluid passage comprises an upper channel spacer layer positioned between the top and intermediate layers, and wherein the upper fluid passage is configured to provide air from an air leak toward the distal end of the upper fluid passage;
   a lower fluid passage at least partially defined between the intermediate and bottom layers, the lower fluid passage configured to be in fluid communication with a source of negative pressure, the lower fluid passage comprising a lower channel spacer layer positioned between the intermediate and bottom layers; and
   at least two openings in the distal end of the bottom layer, wherein at least one opening of the at least two openings is fluidically connected to the lower fluid passage;
   wherein when negative pressure from the source of negative pressure is applied to the lower fluid passage to provide negative pressure to the wound site, fluid flow between the upper fluid passage and the lower fluid passage is directed to pass only through the at least two openings in the distal end of the bottom layer.

2. The apparatus according to claim 1, wherein the upper channel spacer layer comprises foam.

3. The apparatus according to claim 1, wherein the lower channel spacer layer comprises a 3D knitted or 3D fabric material.

4. The apparatus according to claim 1, wherein each of the top layer and the bottom layer has an enlarged distal end.

5. The apparatus according to claim 4, wherein the enlarged distal ends of the top and bottom layers are rectangular.

6. The apparatus according to claim 4, wherein the enlarged distal ends of the top and bottom layers form a teardrop shape.

7. The apparatus according to claim 1, wherein the bottom layer is configured to be attached to a drape.

8. The apparatus according to claim 1, wherein the bottom layer is attached to an applicator.

9. The apparatus according to claim 8, wherein the applicator comprises at least one aperture placed directly beneath at least one of the at least two openings.

10. The apparatus according to claim 1, wherein the air leak is disposed adjacent the proximal end of the upper fluid passage.

11. The apparatus according to claim 1, wherein the air leak comprises a filter.

12. The apparatus according to claim 1, wherein a distal end of the upper channel spacer layer extends farther distally than a distal end of the lower channel spacer layer.

13. The apparatus according to claim 1, further comprising a connector in fluid communication with the proximal end of the lower channel spacer layer.

14. The apparatus according to claim 1, wherein the at least two openings include a first opening and a second opening, wherein the first opening is closer to the distal end of the bottom layer than the second opening.

15. The apparatus according to claim 1, wherein the distal end of the intermediate layer is proximal to at least one of the distal end of the top layer or the distal end of the bottom layer.

16. An apparatus to provide negative pressure to a wound site comprising:
an elongate bridge having a proximal end and a distal end, the elongate bridge comprising a first fluid passage configured to provide negative pressure to the wound site and a second fluid passage configured to provide an air leak toward the wound site; and
an applicator at the distal end of the elongate bridge, the applicator comprising at least two openings;
wherein when negative pressure from a source of negative pressure is applied to the first fluid passage to provide negative pressure to the wound site, fluid flow between the second fluid passage and the first fluid passage is directed to pass only through the at least two openings in the applicator.

17. The apparatus according to claim 16, wherein each of the first fluid passage and the second fluid passage comprises a deformable spacer.

18. The apparatus according to claim 16, wherein the first fluid passage and the second fluid passage are placed side-by-side.

19. The apparatus according to claim 16, wherein the applicator is configured to be attached to a drape.

20. A method of treating a wound, the method comprising:
providing a suction adapter comprising:
an elongate bridge portion having a proximal end and a distal end, the elongate bridge comprising a first fluid passage configured to provide negative pressure to a wound site and a second fluid passage configured to provide an air leak toward the wound site;
an applicator at the distal end of the elongate bridge, the applicator comprising a first opening and a second opening spaced apart from the first opening;
wherein the first fluid passage is fluidically connected to the first opening and the second fluid passage is fluidically connected to the second opening;
situating the first opening and the second opening of the applicator over one or more apertures in a drape covering the wound;
sealing the suction adapter to the drape; and
applying negative pressure to the wound through the suction adapter, wherein air is drawn through the air leak toward the wound site, through the second opening, under the drape, and through the first opening to the first fluid passage.

* * * * *